(12) United States Patent
Zhang et al.

(10) Patent No.: US 8,546,505 B2
(45) Date of Patent: Oct. 1, 2013

(54) CARBAZOLE-BASED HOLE TRANSPORT AND/OR ELECTRON BLOCKING MATERIALS AND/OR HOST POLYMER MATERIALS

(75) Inventors: Yadong Zhang, Alpharetta, GA (US); Seth Marder, Atlanta, GA (US); Carlos Zuniga, Atlanta, GA (US); Stephen Barlow, Atlanta, GA (US); Bernard Kippelen, Decatur, GA (US); Andreas Haldi, Dresden (DE); Benoit Domerq, Waterloo (BE); Marcus Weck, New York, NY (US); Alpay Kimyonok, Besiktas Istanbul (TR)

(73) Assignee: Georgia Tech Research Corporation, Atlanta, GA (US)

( * ) Notice: Subject to any disclaimer, the term of this patent is extended or adjusted under 35 U.S.C. 154(b) by 393 days.

(21) Appl. No.: 12/808,761

(22) PCT Filed: Dec. 19, 2008

(86) PCT No.: PCT/EP2008/068124
§ 371 (c)(1),
(2), (4) Date: Aug. 16, 2010

(87) PCT Pub. No.: WO2009/080799
PCT Pub. Date: Jul. 2, 2009

(65) Prior Publication Data
US 2010/0331509 A1   Dec. 30, 2010

Related U.S. Application Data

(60) Provisional application No. 61/015,641, filed on Dec. 20, 2007.

(51) Int. Cl.
| | | |
|---|---|---|
| C08G 61/06 | (2006.01) | |
| C08F 26/06 | (2006.01) | |
| C07D 401/14 | (2006.01) | |
| C07D 403/14 | (2006.01) | |
| C07D 403/08 | (2006.01) | |
| C07D 209/82 | (2006.01) | |
| C09K 11/06 | (2006.01) | |
| C08F 4/80 | (2006.01) | |

(52) U.S. Cl.
USPC ........ 526/259; 546/276.7; 548/441; 548/434; 548/444; 252/301.35

(58) Field of Classification Search
USPC ............. 526/259; 546/276.7; 548/434, 444; 548/441; 252/301.35
See application file for complete search history.

(56) References Cited

U.S. PATENT DOCUMENTS

| | | | | |
|---|---|---|---|---|
| 6,960,398 B2 * | 11/2005 | Kido et al. | ..... | 428/690 |
| 7,504,162 B2 * | 3/2009 | Nomura et al. | ..... | 428/690 |
| 2008/0145665 A1 * | 6/2008 | Ye et al. | ..... | 428/412 |
| 2011/0196104 A1 * | 8/2011 | Kimyonok et al. | ..... | 525/274 |

FOREIGN PATENT DOCUMENTS

| | | |
|---|---|---|
| WO | WO 2006/084088 A1 | 8/2006 |
| WO | WO 2009/026235 A2 | 2/2009 |
| WO | WO 2009/080796 A1 | 7/2009 |
| WO | WO 2009/080797 A1 | 7/2009 |

OTHER PUBLICATIONS

Bloxham, et al, "Synthesis and solid state structures of N,N'-linked carbazoles and indoles," Tetrahedron 58 (2002) 3709-3720.*
Kimyonok A. et. al—"Norbornene-based copolymers with iridium complexes and bis(carbazolyl)fluorene groups in their side-chains and their use in light-emitting diodes", Chem. Mater., 2007, pp. 5602-5608, vol. 19, Issue 23; 7 pgs.
Cho J-Y. et. al—"Synthesis and characterization of polymerizable phosphorescent platinum(II) complexes for solution-processible organic light-emitting diodes", Organometallics, 2007, pp. 4816-4829, vol. 26, Issue 19; 14 pgs.
Furstner et. al—"Olefin metathesis and beyond", Angewandte Chemie International Edition, 2000, pp. 3012-3043, vol. 39, Issue 17; 32 pgs.
Trnka et. al.—"The development of L2X2RuCHR olefin metathesis catalysts: An organometallic success story", Acc. Chem. Res., 2001, pp. 18-29, vol. 34, Issue 1; 12 pgs.
Ivin, J. & Mol, I. C., Eds.,"Olefin Metathesis and Metathesis Polymerization", 2nd Ed.; book; Academic: New York, 1996 (submitted electronically via EFS in 10 parts).
Grubbs, R. H., Ed, "Handbook of Metathesis", vol. 3—Application in Polymer Synthesis; book; Wiley-VCH: Weinheim, 2003 (submitted electronically via EFS in 14 parts).
Kulkarni et. al.—"Electron transport materials for organic light-emitting diodes", Chem. Mater., 2004, pp. 4556-4573, vol. 16, Issue 23; 18 pgs.
Evans, N.R et al.—"Triplet energy back transfer in conjugated polymers with pendant phosphorescent iridium complexes"—J. Am. Chem. Soc., 2006, vol. 128, pp. 6647-6656; 10 pgs.
Lan Deng et al.—"Living radical polymerization of bipolar transport material for highly efficient light emitting diodes"—Chem Mater. 2006, vol. 18, pp. 386-395; 10 pgs.
Jiaxing Jiang et al.—"High-efficiency electrophosphorescent fluorene-alt-carbazole copolymers N-grafted with cyclometalated ir complexes"—Macromolecules 2005, vol. 38, pp. 4072-4080; 9 pgs.
Gisela Schulz—"Enhancement of phosphorescence of Ir complexes bound to conjugated polymers : increasing the triplet level of the main chain"—Macromolecules, 2006, vol. 39, pp. 9157-9165; 9 pgs.

(Continued)

Primary Examiner — Fred M Teskin
(74) Attorney, Agent, or Firm — Foley & Lardner LLP

(57) ABSTRACT

This invention relates generally to norbornene-monomer, poly(norbornene)homopolymer, and poly(norbornene)copolymer compounds containing a functionalized carbazole side chain, having desirable solution processability and host characteristics. It also relates to hole transport and/or electron blocking materials, and to organic host materials for an organic luminescence layer, an OLED device, and compositions of matter which include these compounds.

24 Claims, 7 Drawing Sheets

(56) References Cited

OTHER PUBLICATIONS

Kai Zhang et al.—"Saturated red-emitting electrophosphorescent polymers with iridium coordinating to beta-diketonate units in the main chain"—Macromol Rapid Commun, 2006, vol. 27, pp. 1926-1931; 6 pgs.

Hongyu Zhen et al.—"Synthesis and properties of electrophosphorescent chelating polymers with iridium complexes in the conjugated backbone"—Chem Eur J, 2005, vol. 11, pp. 5007-5016; 10 pgs.

Xiwen Chen et al.—"High-efficiency red-light emission from polyfluorenes grafted with cyclometalated iridium complexes and charge transport moiety"—J Am Chem Soc, 2003, vol. 125, pp. 636-637; 2 pgs.

Hongyu Zhen et al.—"White-light emission from a single polymer with singlet and triplet chromophores on the backbone"—Macromol Rapid Commun, 2006, vol. 27, pp. 2095-2100; 6 pgs.

Jiaxing Jiang et al.—"High-efficiency white-light-emitting devices form a single polymer by mixing singlet and triplet emission"—Adv Mater, 2006, vol. 18, pp. 1769-1773; 5 pgs.

Youngmin You et al.—"Blue electrophosphorescence from iridium complex covalently bonded to the poly(9-dodecyl-3-vinylcarbazole) : suppressed phase segregation and enhanced energy transfer"—Macromolecules, 2006, vol. 39, pp. 349-356 ; 8 pgs.

Hongyu Zhen et al.—"Electrophosphorescent chelating copolymers based on linkage isomers of naphthylpyridine—iridium complexes with fluorene"—Macromolecules, 2006, vol. 39, pp. 1693-1700; 8 pgs.

Frederique Loiseau et al.—"Dendrimers made of porphyrin cores and carbazole chromophores as peripheral units. Absorption spectra, luminescence properties, and oxidation behavior"—J Am Chem Soc, 2005, vol. 127, pp. 11352-11363; 12 pgs.

Evan L. Williams et al.—"Excimer-based white phosphorescent organic light emitting diodes with nearly 100% internal quantum efficiency"—Adv Mater, 2007, vol. 19, pp. 197-202; 6 pgs.

U.S. Appl. No. 60/956,492, filed Aug. 17, 2007, Alpay Kimyonok et al.

U.S. Appl. No. 61/040,212, filed Mar. 28, 2008, Alpay Kimyonok et al.

U.S. Appl. No. 61/015,650, filed Dec. 20, 2007, Ali Hayek et al.

U.S. Appl. No. 61/015,777, filed Dec. 21, 2007, Seth Marder et al.

U.S. Appl. No. 12/673,299, Alpay Kimyonok et al.

U.S. Appl. No. 12/808,739, filed Aug. 16, 2010, Ali Hayek et al.

U.S. Appl. No. 12/808,743, filed Aug. 16, 2010, Seth Marder et al.

\* cited by examiner

CARBAZOLE-BASED HOLE TRANSPORT AND/OR ELECTRON BLOCKING MATERIALS AND/OR HOST POLYMER MATERIALS

CROSS-REFERENCE TO RELATED APPLICATIONS

This application is a U.S. national stage application under 35 U.S.C. 371 of International Application No. PCT/EP2008/068124 filed Dec. 19, 2008, which claims the priority of U.S. Provisional Application No. 61/015,641 filed Dec. 20, 2007. The entire disclosure of the predecessor application is hereby incorporated herein by reference in its entirety.

STATEMENT REGARDING FEDERALLY SPONSORED RESEARCH OR DEVELOPMENT

This invention was made with government support under a grant from the Office of Naval Research, Grant No. 68A-1060806. The U.S. Government has certain rights in this invention.

FIELD OF THE INVENTION

This invention relates generally to norbornene monomers, poly(norbornene) homopolymers, and poly(norbornene)copolymer compounds containing a functionalized carbazole side chain, and to hole transport and/or electron blocking materials, and organic host materials for an organic luminescence layer, organic electronic devices, and compositions of matter which include these compounds.

BACKGROUND OF THE INVENTION

Although initial work on organic light-emitting diodes (OLEDs) has focused on fluorescence emission, this type of emission is limited by the inability to capture energy from triplet excited states. Therefore, current research has been aimed towards electrophosphorescent (EP) devices, which in principle are capable of achieving up to 100% internal emission efficiency through harvesting both singlet and triplet excitons and which is potentially a more efficient approach than a purely fluorescent device where only singlet exciton provides a radiative pathway. One way of achieving electrophosphorescence involves doping heavy metal complexes (e.g., Ir and Pt complexes) into organic host materials in a multi-layered organic light-emitting diode. These heavy metal complexes typically exhibit efficient intersystem crossing from their singlet to triplet excited states and the triplet states can then relax through phosphorescence. EP devices have been demonstrated as candidates for full-color display applications. Devices have also been developed that exhibit broadband white emission. In guest-host systems where energy transfer is the predominant mechanism for generation of luminescent species, charge carrier recombination principally occurs on the host materials, and the energy created is transferred from the singlet or triplet state of the host to the singlet or triplet excited state of the phosphorescent guest. In order to develop an effective guest-host system, the host material should fulfill energy-level matching with neighboring layers of the device for efficient charge injections and with the phosphorescent guest material for effective energy transfer of singlet and triplet excitons (in particular requiring that the singlet and triplet energies of the host should be higher in energy than the those of the guest), and for efficient triplet confinement at the guest (requiring that the host triplet energy is higher than that of the guest to avoid energy transfer back from the excited guest to the host).

The development of white polymer light-emitting devices has been aimed at their potential applications in low-cost back-lighting in liquid-crystal displays, in full-color displays, and as next generation lighting sources envisioned to replace the incandescent light bulb and fluorescent lamp in some applications. White light emission in polymer light emitting diodes, which is usually difficult to achieve from a single polymer, can be sought in polymer-blend systems with multifunctional emitting components. Based on the guest-host approach, single dopant white light-emitting diodes (WOLED) have been achieved in small molecule systems.

There is currently a need to establish more efficient and cost effective methods for OLED fabrication than the widely used high-vacuum vapor-deposition methods for devices where the host and guest are small molecules.

SUMMARY OF THE INVENTION

The present invention provides solution processable norbornene monomers, poly(norbornene)s or poly(norbornene) copolymer compounds containing a functionalized carbazole side chain, which are useful as hole transport and/or electron blocking materials, for use as organic host materials for organic luminescence layers, organic electronic devices, and compositions of matter which include these compounds.

These novel side-chain carbazole functionalized host materials can be processed using low-cost fabrication technologies, such as spin-coating and printing, described herein. The target polymers are based on a "norbornene-carbazole" monomer structure that can be readily polymerized by ring opening metathesis polymerization (ROMP) using various known metal complexes. Attaching functional groups as the side chain to a non-conjugated polynorbornenyl polymer backbone is advantageous for the transformation of crystalline electroluminescent monomeric materials to long lifetime amorphous polymeric derivatives. The phosphor guest can either be a small molecule or can be another norbornene monomer that is copolymerized with the host monomer.

In accordance with the purpose(s) of this invention, as embodied and broadly described herein, in some aspect these inventions relate to a compound within the scope of formula (I):

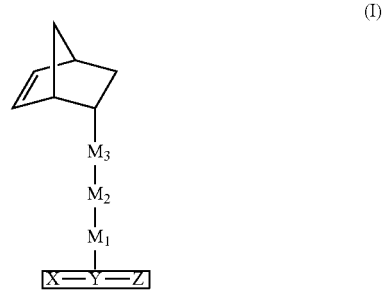

(I)

wherein:
X and Z comprise carbazole groups;
Y is a cyclic or polycyclic aromatic or heteroaromatic group;
the X—Y—Z unit taken together is linked to the norbornene monomer by $M_1$-$M_2$-$M_3$ linker groups, wherein the identities of $M_1$, $M_2$, and $M_3$ groups will be further described below.

In other aspects, the inventions relate to polymers or copolymers comprising monomeric units within the scope of formula (II):

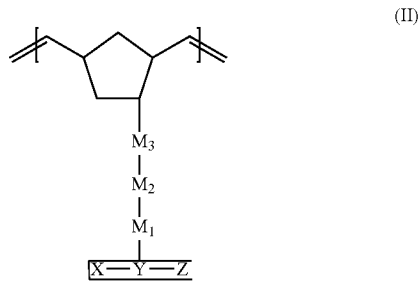

(II)

wherein X, Y, Z, $M_1$, $M_2$, and $M_3$ are described herein.

In related aspects, the invention provides hole transport and/or electron blocking materials, and organic host materials comprising the polymer and copolymers of formula (II) for use in organic electronic devices.

In related aspects, the invention provides organic host materials for an organic luminescence layer comprised of the monomer of formulas (I) or polymers of copolymers of formula (II) in combination with a phosphorescent dopant.

DETAILED DESCRIPTION OF THE INVENTION

Figure 1:
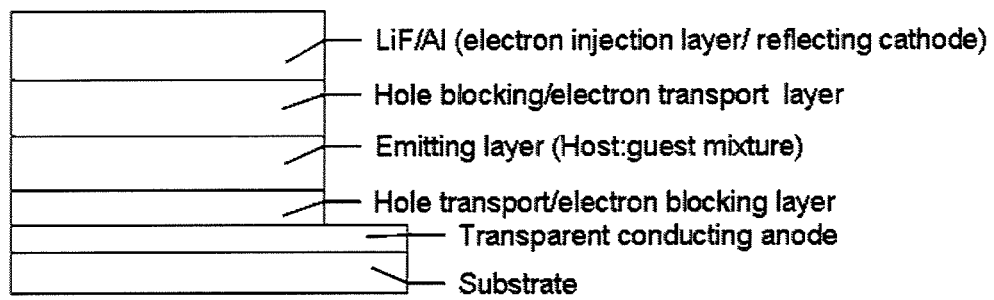
FIG. 1. Example of layer configurations in an organic electronic device.

In order to create organic polymeric host materials that can be processed using low-cost fabrication technologies, such as spin-coating from solution, we have synthesized novel side-chain carbazole functionalized monomer and polymer systems containing hole transporting carbazole groups as side-chains. The target polymers are based on "norbornene-carbazole" functionalized monomer structures that can be readily polymerized by ring opening metathesis polymerization (ROMP) using various metal catalyst complexes. Attaching functional groups as the side chain to a non-conjugated polymer transforms crystalline small molecule materials to long lifetime amorphous polymeric derivatives having improved hole-carrying properties and processing characteristics.

The carbazole functionalized amorphous polymers can serve as hosts that can incorporate high loadings of phosphor guests while minimizing interaction between the phosphors. The phosphor guests can either be a small molecule or another norbornene monomer that is copolymerized with the host monomers. Since electro-optical properties of the hole-carrying hosts can be tuned by modification of the molecular structure and by copolymerization, tailor-made host materials for electroluminescent devices are accessible by means of this novel approach.

The carbazole materials disclosed herein are hole transporting materials, and their highest-occupied molecular orbital (HOMO) energies, as well as their morphological characteristics, can be tuned by substitution of appropriate groups on the carbazole groups. Tunability is a desirable feature that permits optimization by alignment of the energy levels of the host with the guest or with the electrodes or other layers of the device for increased device efficiency. In addition, the carbazoles described herein exhibit high singlet and triplet excited state energies, with triplet energies of up to 3 eV. These energies allow for effective excitation of a phosphorescent guest by either Förster or Dexter energy transfer from the singlet or triplet state.

The present invention may be understood more easily by reference to the following detailed description of preferred embodiments of the invention and the Examples included therein.

Before the present compounds, compositions, articles, devices, and or methods are disclosed and described, it is to be understood that the terminology used herein is for the purpose of describing particular embodiments only and is not intended to be limiting.

Definitions

It must be noted that as used in the specification and the appended claims, the singular forms "a" "an" and "the" include plural referents unless the context clearly dictates otherwise. Thus, for example, reference to "a cyclic compound" includes mixtures of aromatic compounds.

In the specification and claims which follow, reference will be made to a number of terms which shall be defined to have the following meanings:

An asterisk (*) is often used in the drawings herein to denote the point of attachment of the chemical structure illustrated in the drawing to other parts of the chemical structure of a larger molecule.

Ranges are often expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment.

The term "alkoxy" refers to a straight, branched or cyclic $C_{1-20}$ alkyl-O, where the alkyl group maybe optionally substituted.

The term "alkyl" refers to a branched or straight chain saturated hydrocarbon group, having a carbon chain length of from 1 to 20 carbon atoms, such as methyl, ethyl, propyl, n-propyl, isopropyl, butyl, n-butyl, isobutyl, t-butyl, octyl, decyl, decyl, tetradecyl, hexadecyl, eicosyl, tetracosyl, cyclopentyl, cyclohexyl and the like. When substituted, alkyl groups may be substituted with at least one member selected from the group consisting of CN, $NO_2$, S, NH, OH, COO— and halogen at any available point of attachment. When the alkyl group is said to be substituted with an alkyl, this is used interchangeably with "branched" alkyl group.

The term "aryl" refers to aromatic rings used as substituents, e.g. phenyl, substituted phenyl, and the like as well as rings which are fused, e.g. naphthyl, phenanthrenyl, and the like. An aryl group thus contains at least one ring having at least 6 atoms. Substituents on the aryl group may be present on any position, i.e., ortho, meta, or para positions or fused to the aromatic ring. More particularly, aryl groups may be an unsubstituted or substituted aromatic or heteroaromatic group, and the aromatic or heteroaromatic group may be substituted with a substituent independently selected from the group consisting of a different aryl group, alkyl groups, halogens, fluoroalkyl groups; alkoxy groups, and amino groups. The term "cyclic" can refer either to an aryl group or to a cyclic alkyl group such as a cyclohexyl substituent.

The term "heteroaromatic" refers to a conjugated monocyclic aromatic hydrocarbon group having 5 or 6 ring atoms, a conjugated bicyclic aromatic group having 8 to 10 atoms, or a conjugated polycyclic aromatic group having at least 12 atoms, containing at least one heteroatom, O, S, or N, in which a C or N atom is the point of attachment, and in which 1 or 2 additional carbon atoms is optionally replaced by a heteroatom selected from O, or S, and in which from 1 to 3 additional carbon atoms are optionally replaced by nitrogen heteroatoms, said heteroaromatic group being optionally substituted as described herein. Examples of this type are pyrrole, oxazole, thiazole and oxazine. Additional nitrogen atoms may be present together with the first nitrogen and oxygen or sulfur, giving, e.g. thiadiazole. Suitable heteroaromatic compounds are carbazole, purine, indole, pyridine, pyrimidine, pyrrole, imidazole, thiazole, oxazole, furan, thiophene, triazole, pyrazole, isoxazole, isothiazole, pyrazine, pyridazine, and triazine. The term "heterocyclic" can refer to both the heteroaryl species defined above, or to saturated heterocyclic groups.

The term "diyl" refers to a group of atoms attached to two other groups of atoms in two places.

The terms "alkanediyl" or "alkane diyl" refers to a straight chain, branched chain or cyclic alpha, omega-alkanediyl having a carbon chain length of from 1 to 20 carbon atoms, such as methane diyl, ethane diyl, propane diyl and the like.

The terms "alkenediyl" or "alkene diyl" refers to a straight chain, branched chain or cyclic alpha, omega-alkenediyl having a carbon chain length of from 1 to 20 carbon atoms, such as ethene diyl, propene diyl, butane diyl and the like.

The terms "alkynediyl" or "alkyne diyl" refers to a straight chain, branched chain or cyclic alpha, omega-alkynediyl having a carbon chain length of from 1 to 20 carbon atoms, such as ethyne diyl, propyne diyl, butyne diyl and the like.

The term "arene diyl" refers to an aromatic or heteroaromatic aryl group where two the hydrogen atoms are removed allowing for a group to be substituted at the position where the two hydrogen atoms were removed, and having a chain length of from 1 to 20 carbon atoms.

The term "carbazole" as used herein is meant to describe an optionally substituted moiety comprising a carbazolyl ring sub-structure as shown and numbered below, and where $R_4'$, $R_4''$ and x will be further described herein.

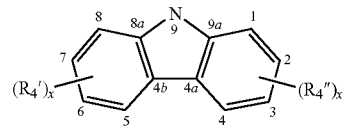

The Monomeric Carbazoles

Many embodiments of the present inventions relate to compounds represented by the formula (I):

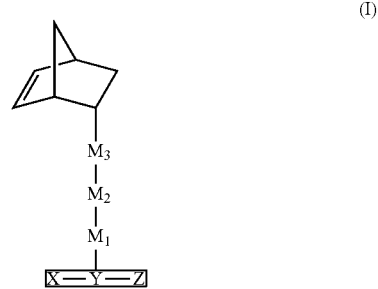

wherein:

X and Z each are carbazoles and are optionally substituted;

Y is a conjugated cyclic or polycyclic aromatic or heteroaromatic;

the X—Y—Z unit taken together is linked to the norbornene monomer by a linkage, $M_1$-$M_2$-$M_3$, wherein the linkage is attached to Y or one of X or Z;

$M_1$ and $M_3$ are independently absent or represent

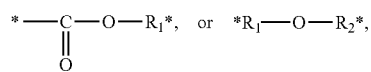

and is attached to the X—Y—Z unit through the carbon or oxygen atom on the ester, or through the ether oxygen atom, and $M_2$ is $R_3$;

$R_1$ and $R_2$ are independently absent or selected from the group consisting of alkane diyl, alkene diyl, alkyne diyl, and arene diyl, each of which are straight chain, branched chain or cyclic, having a carbon chain length of from 1 to 20 carbon atoms; and $R_3$ is absent or represents alkane diyl, alkene diyl, alkyne diyl, or arene diyl, each of which are straight chain, branched chain or cyclic, having a carbon chain length of $C_{1-20}$.

For example the carbazole monomers can be represented by the formulas Ia and Ib:

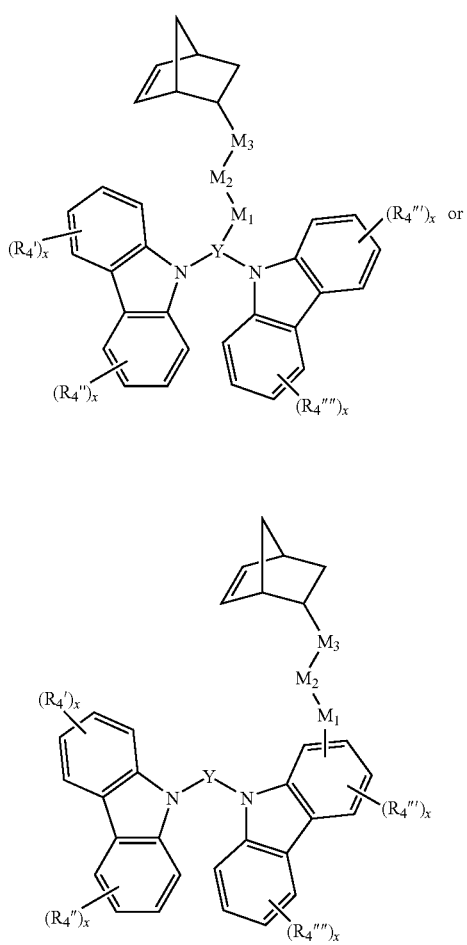

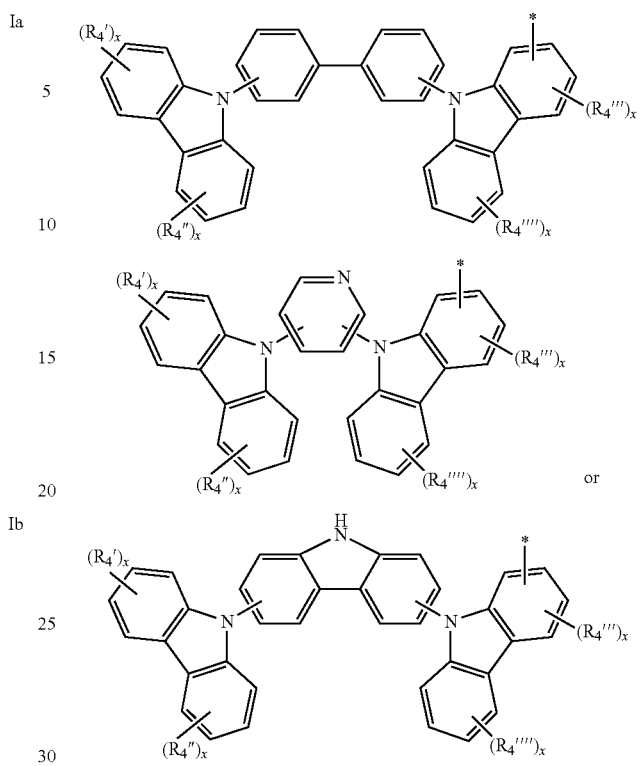

In formulas I, Ia and Ib, Y can be a $C_{1-20}$ monocyclic aromatic or a monocyclic or polycyclic heteroaromatic ring that can be optionally substituted with one or more $C_{1-20}$ alkyl, aryl, or alkoxy groups. For example, Y can be any of the following substituted or unsubstituted rings: carbazole, purine, indole, indoline, carboline, naphthalene, azulene, anthracene, phenanthrene, benzene, phenyl, pyridine, pyrrole, oxazole, thiazole, pyrrole, imidazole, furan, thiophene, triazole, pyrazole, isoxazole, pyrazine, pyridazine, or triazine ring(s). In some embodiments, the Y group of compound Ib can be fluorine or biphenyl.

Y can also be preferably a carbazole, pyridine, biphenyl or benzene, as shown below:

Y can also be a carbazole substituted with alkyl groups such as t-butyl, preferably at the 3- and 6-position on the carbazole.

In formula Ia and Ib, each x is independently selected and can be an integer 0, 1, 2, 3 or 4. Each $R_4'$, $R_4''$, $R_4'''$, or $R_4''''$ group can be independently selected and can be one or more $C_{1-20}$ alkyl, aryl, or alkoxy groups attached at any position on the carbazole ring. In another related embodiment $R_4'$, $R_4''$, $R_4'''$, and $R_4''''$ can be independently selected $C_{1-6}$ alkyl or alkoxy groups, such as methyl, ethyl, propyl, butyl, iso-propyl, iso-butyl, sec-butyl, tent-butyl, methoxy, ethoxy, propoxy, iso-propoxy, sec-butoxy, tent-butoxy or butoxy groups. In some embodiments, $R_4'$ $R_4''$, $R_4'''$, and $R_4''''$ are all tert-butyl.

In Formula I, Ia, and Ib, the combination of the X, Y, and Z hole-carrying carbazole moieties can be represented by the functional groups below, wherein they can be attached through a linker placed at any position; and the aromatic or heteroaromatic rings can be optionally substituted as already described.

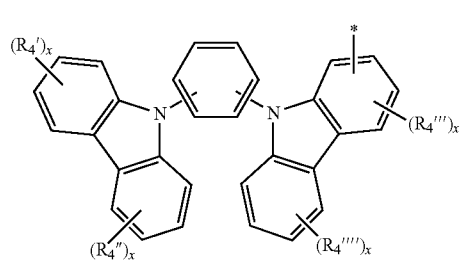

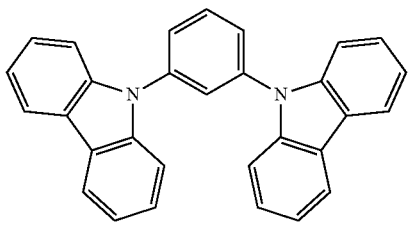

1,3-Bi(carbazol-9-yl)-benzene (mCP)

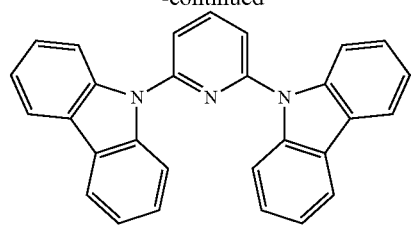

2,6-Bis(carbazol-9-yl)-pyridine
(mCPy)

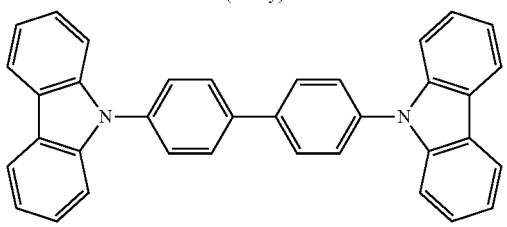

4,4'-Bis(carbazol-9-yl)biphenyl
(CBP)

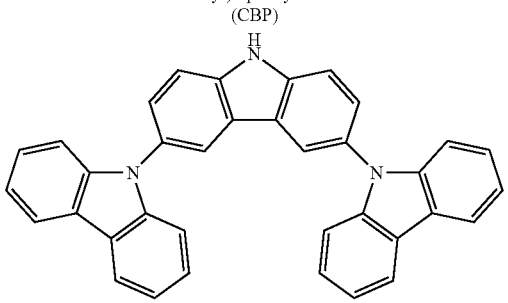

3,6-Di(carbazol-9-yl)carbazole ("tricarbazole")

$M_1$ and $M_3$ can be absent or represented by the formulas:

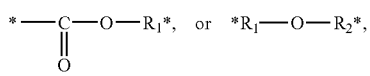

wherein $R_1$ and $K_2$ can be independently absent or selected from the group consisting of alkane diyl, alkene diyl, alkyne diyl, and arene diyl, each of which are straight chain, branched chain or cyclic, having a carbon chain length of from 1 to 20 carbon atoms.

In formula I, $M_2$ can be $R_3$. $R_3$ can be absent or represents alkane diyl, alkene diyl, alkyne diyl, or arene diyl, each of which are straight chain, branched chain or cyclic, having a carbon chain length of $C_{1-20}$.

In formula I, Ia and Ib, $M_1$ and $M_3$ are optional or can be independently selected from:

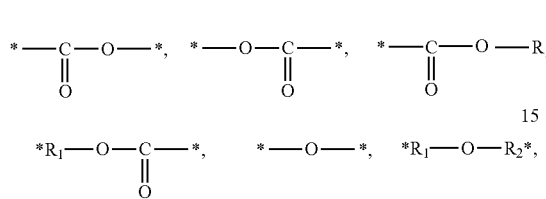

$*R_1-O-*,\quad *-O-R_1*,\quad *-O-R_2*,\quad$ or $*R_2-O-*,$ wherein $M_1$ and $M_3$ can be bound to the norbornene, Y, or carbazole groups at the positions indicated by *.

$R_1$ and $R_2$ are optional and can be independently selected $C_{1-20}$ alkane diyl, alkene diyl, alkyne diyl, or arene diyl groups. In another related embodiment $R_1$ and $R_2$ can be $C_{1-11}$ alkane diyls of the generic formula $-(CH_2)_n-$, such as methylene diyl, ethylene diyl, propylene diyl, butylene diyl, pentylene diyl, hexylene diyl, heptylene diyl, octylene diyl, nonylene diyl, decylene diyl, or dodecylene diyl $M_2$ is optional or can be a $C_{1-20}$ alkane diyl, alkene diyl, alkyne diyl, or arene diyl group are as defined above. In another related embodiment, $M_2$ is absent or can be a $C_{1-11}$ alkane diyl such as methylene diyl, ethylene diyl, propylene diyl, butylene diyl, pentylene diyl, hexylene diyl, heptylene diyl, octylene diyl, nonylene diyl, decylene diyl, or dodecylene diyl.

In many embodiments, the $M_3$-$M_2$-$M_1$ linker groups can be represented together by the formulas:

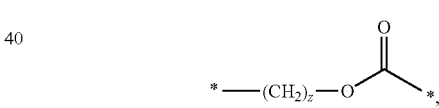

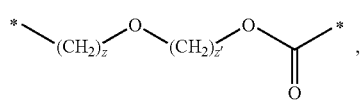

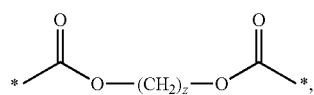

wherein z and z' are independently selected integers from 0 to about 12.

In related embodiments, the inventions relate to the following novel substituted norbornenyl monomeric compounds:

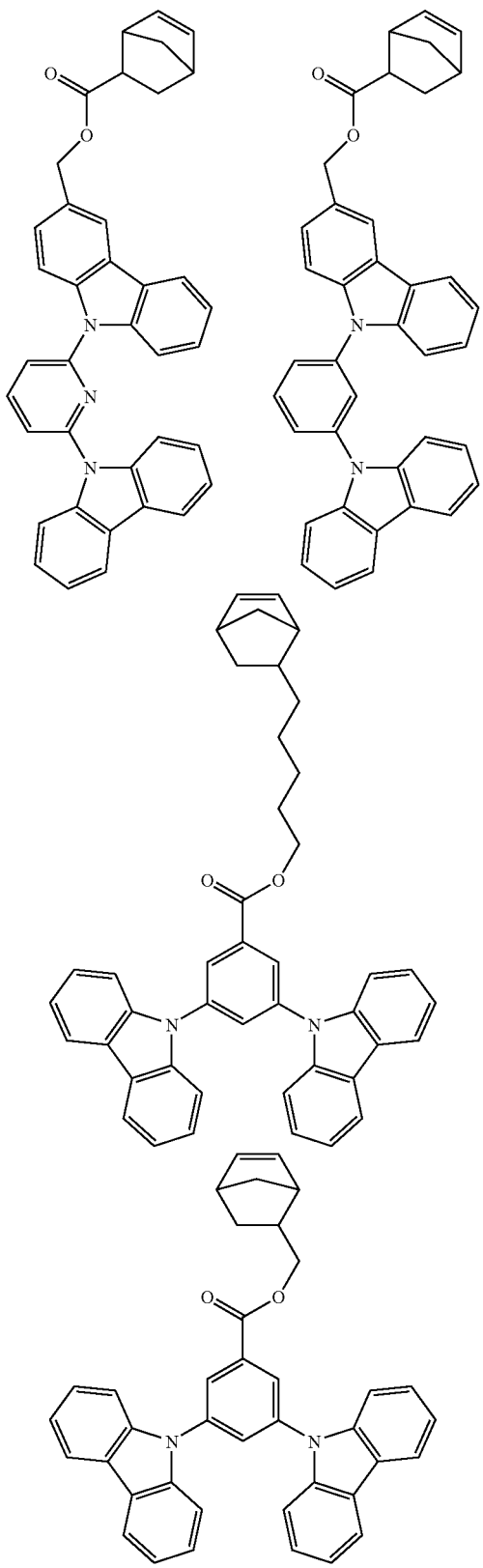

The Polymeric Carbazoles

The inventions described herein also provide polymers or copolymers that can be obtained by polymerizing the monomer I, Ia, or Ib, optionally in the presence of other norbornenyl monomers, which can be represented by the formula (II):

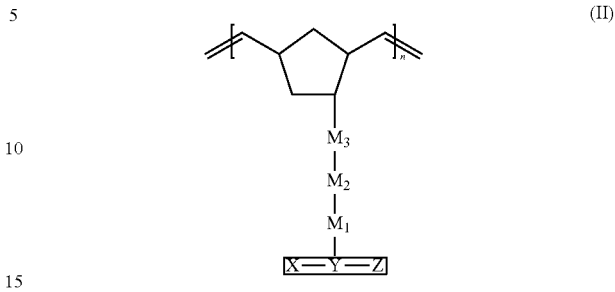

wherein:

X and Z each are carbazole and are unsubstituted or substituted with one or more straight chain or branched $C_{1-20}$ alkyl groups;

Y is a conjugated cyclic or polycyclic aromatic or heteroaromatic;

the X—Y—Z unit taken together is linked to the norbornene polymer by a linkage, $M_1$-$M_2$-$M_3$, wherein the linkage is attached to Y or one of X or Z;

$M_1$ and $M_3$ are independently absent or represent

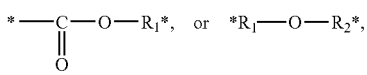

and are attached to the X—Y—Z unit through the carbon or oxygen atom on the ester, or through the ether oxygen atom, and $M_2$ is $R_3$;

$R_1$ and $R_2$ are independently absent or selected from the group consisting of alkane diyl, alkene diyl alkyne diyl, and arene diyl, each of which are straight chain, branched chain or cyclic, having a carbon chain length of from 1 to 20 carbon atoms;

$R_3$ is absent or represents alkane diyl, alkene diyl, alkyne diyl, or arene diyl, each of which are straight chain, branched chain or cyclic, having a carbon chain length of $C_{1-20}$, and n is an integer of from about 1 to about 2,000.

In related aspects the inventions provide polymers represented by the formulas:

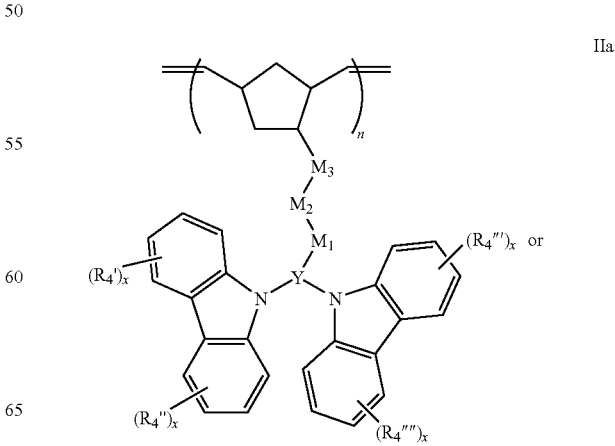

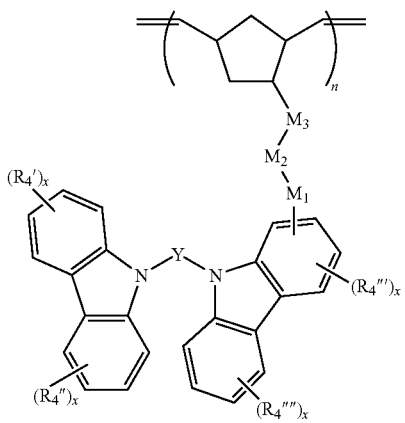
IIb

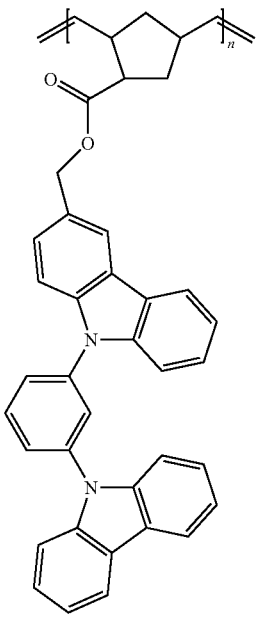
YZ-I-57 where $R_4'$, $R_4''$, $R_4'''$, $R_4''''$, X, Y, $M_1$, $M_2$, $M_3$, $R_1$, and $R_2$ are as is defined and described above for monomers I, Ia and Ib.

In polymer II, IIa and IIb, n can be an integer from about 1 to about 2000. The subscript "n" refers to the number of repeat units in the polymer. With respect to the polymers in this invention, "n" is from about 1 to about 2,000 repeat units. More preferably, "n" is from about 5 to about 2000, or 700 to about 1,500 repeat units. Most preferably, "n" is from about 20 to about 500 repeat units.

In a related embodiment, the invention relates to the following novel homo-polymers:

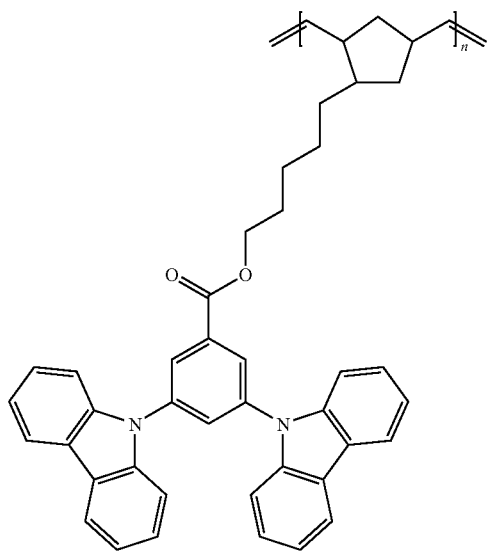
YZ-I-133

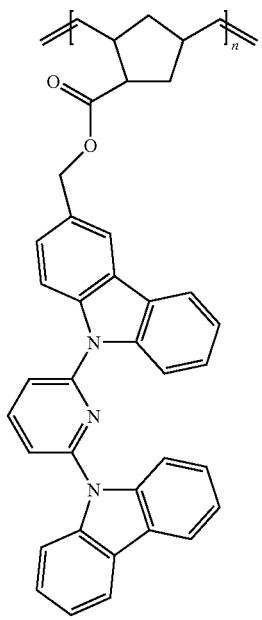
YZ-I-63

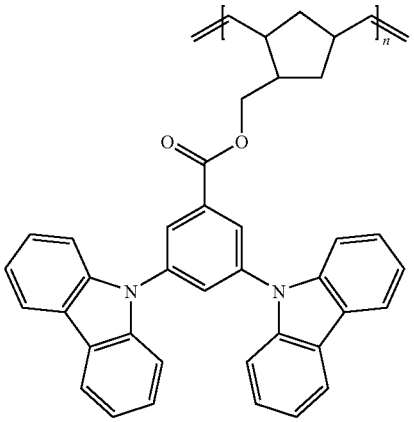
YZ-I-107

A related embodiment of the invention entails processes for preparing a polymer or copolymer where one or more monomeric compounds I, Ia or Ib is mixed with a ring opening metathesis catalyst and optionally one or more additional norbornenyl monomers, and then polymerized to form polynorbornenes II, IIa or IIb or copolymers containing the repeat units illustrated in formulas II, IIa, or IIb.

In another related embodiment, the invention relates to the polymer or copolymer product produced by polymerizing or copolymerizing a mixture containing at least one of monomers I, Ia or Ib and optionally other suitable monomers in the presence of a ring opening metathesis catalyst.

In another related embodiment the polymerization process can be carried out by mixing another optional monomer into the monomeric mixture and then copolymerizing the mixture with a suitable ROMP catalyst to form a carbazole functionalized poly(norborne).

Poly(norbornene)s can be polymerized via ring-opening metathesis polymerization (ROMP), a living polymerization method resulting in polymers with controlled molecular weights, low polydispersities, and also allows for the easy formation of block co-polymers. See, for example, Fürstner, A. *Angew. Chem., Int. Ed.* 2000, 39, 3013; T. M. Trnka, T. M.; Grubbs, R. H. *Acc. Chem. Res.* 2001, 34, 18; *Olefin Metathesis and Metathesis Polymerization, 2nd Ed.*; Ivin, J., Mol, I. C., Eds.; Academic: New York, 1996; and *Handbook of Metathesis, Vol. 3-Application in Polymer Synthesis*; Grubbs, R. H., E d.; Wiley-VCH: Weinheim, 2003, each of which is respectively incorporated herein by reference for the teachings regarding methods and catalysts for ROMP polymerizations. Catalysts commonly used by those skilled in the art include Grubb's ruthenium catalysts (below).

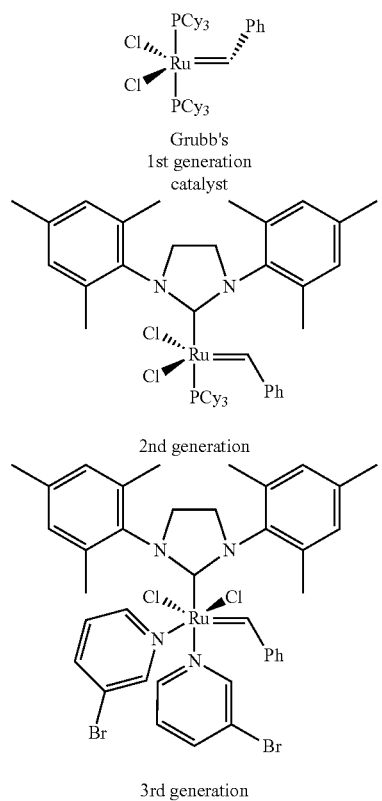

ROMP polymerizations can also be carried out with molybdenum or tungsten catalysts such as those described by Schrock (*Olefin Metathesis and Metathesis Polymerization, 2nd Ed.*; Ivin, J., Mol, I. C., Eds.; Academic: New York which is respectively incorporated herein by reference for the teachings regarding molybdenum or tungsten catalysts for ROMP polymerizations). Furthermore, ruthenium-based ROMP initiators are highly functional-group tolerant, allowing for the polymerization of norbornene monomers containing fluorescent and phosphorescent metal complexes.

The copolymers disclosed herein can include copolymerized subunits derived from optionally substituted strained ring olefins such as, but not limited to, dicyclopentadienyl, norbornenyl, cyclooctenyl and cyclobutenyl monomers. Such monomers can be copolymerized with the compounds of formulas I, Ia, or Ib via ring opening metathesis polymerization using an appropriate metal catalyst, as would be obvious to those skilled in the art.

Compounds I, Ia, Ib, II, IIa and IIb can each be used as a hole transport host component of organic electronic devices. Organic electronic devices include but are not limited to, active electronic components, passive electronic components, electroluminescent (EL) devices (e.g., organic light emitting devices (OLEDs)), photovoltaic cells, light-emitting diodes, field-effect transistors, phototransistors, radio-frequency ID tags, semiconductor devices, photoconductive diodes, metal-semiconductor junctions (e.g., Schottky barrier diodes), p-n junction diodes, p-n-p-n switching devices, photodetectors, optical sensors, phototransducers, bipolar junction transistors (BJTs), heterojunction bipolar transistors, switching transistors, charge-transfer devices, thin-film transistors, organic radiation detectors, infra-red emitters, tunable microcavities for variable output wavelength, telecommunications devices and applications, optical computing devices, optical memory devices, chemical detectors, combinations thereof, and the like.

Charge-transport molecular and polymeric materials disclosed herein are semi-conducting materials in which charges can migrate under the influence of an electric field. These charges may be present due to doping with oxidizing or reducing agents, so that some fraction of the transport molecules or polymer repeat units is present as radical cations or anions. More usually, charges are introduced by injection from another material under the influence of an electric field. Charge-transport materials may be classified into hole- and electron-transport materials. In a hole-transport material, electrons are removed, either by doping or injection, from a filled manifold of orbitals to give positively charged molecules or polymer repeat units. Transport takes place by electron-transfer between a molecule or polymer repeat unit and the corresponding radical cation; this can be regarded as movement of a positive charge (hole) in the opposite direction to this electronic motion. The monomeric compounds of Formulas I, Ia, Ib, as well as the polymeric materials II, IIa, and IIb, or similar copolymers, are hole transport materials.

In an electron-transport material, extra electrons are added, either by doping or injection; here the transport process includes electron-transfer from the radical anion of a molecule or polymer repeat unit to the corresponding neutral species.

The organic electronic devices described herein can contain the following layers: a transparent substrate, a transparent conducting anode overlying the substrate, a hole transport layer and/or an electron blocking layer over the anode, a light-emitting layer, an electron transport and/or hole-blocking layer, and a cathode layer (See FIG. 1).

A plurality of layers of charge-transport materials can be produced to form a charge-transport layer that can have a thickness of about 0.01 to 1000 µm, 0.05 to 100 µm, 0.05 to 10 µm. The length and width of the charge-transport layer can vary depending on the application, but in general, the length can be about 0.01 µm to 1000 cm, and the width can be about 0.01 µm to 1000 cm. It should also be noted that the invention could be used as mixtures with other electron transport materials including those described herein, as well as others. Likewise the charge-transport materials could be used in combination with other hole transport materials, sensitizers, emitters, chromophores, and the like, to add other functionality to devices.

In some embodiments of the inventions, the transparent substrate of the organic electronic device could be either glass or flexible plastic.

The transparent conducting anode could be a high work function metal oxide such as indium tin oxide (ITO), zinc oxide, and indium zinc oxide.

In the organic electronic device, any of monomers I, Ia, or Ib, or any of polymers II, IIa or IIb can be used as a hole transport host material in one or more layers in the device. The hole transport layer can be formed by spin coating solutions of polymer II, IIa, or IIb, preferably to an optimized thickness. In some embodiments of the inventions, the hole transport layers could contain any of CZ-I-25, YZ-I-135, CZ-I-141, YZ-I-63, and YZ-I-57. In other embodiments of the devices described herein, wherein the compounds of this invention are used in other layers, such as the emissive layer, the hole transport layer can be a cross-linked poly-TPD-F film, wherein poly-TPD-f is a known photo-cross-linkable acrylate co-polymer having the structure shown below:

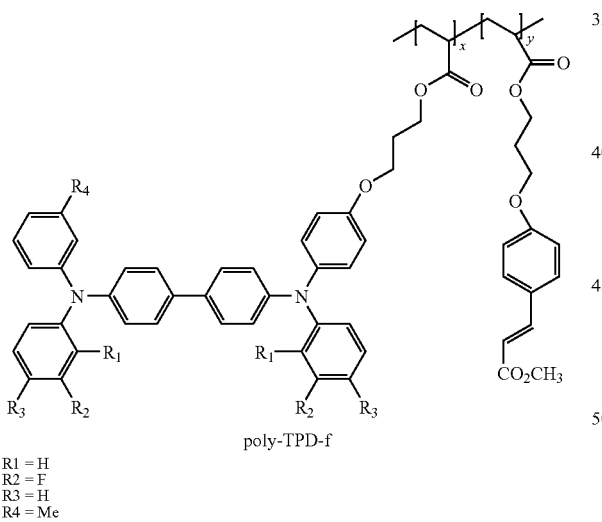

poly-TPD-f

R1 = H
R2 = F
R3 = H
R4 = Me

The hole transport layer can be formed by spin coating the poly-TPD-F from solution onto the transparent anode and cross-linking the film using a broad-band UV light source.

The optional hole transport layer could be present between the light-emitting layer and the anode layer. Alternatively, the optional electron transporting and/or hole-blocking layer could be present between the light-emitting layer and the cathode layer. In related embodiments of the devices of the inventions, the light-emitting layer of the device can comprise a poly(norbornene) homopolymer, or a poly(norbornene)co-polymer compound that can be represented by polymer II, IIa, or IIb. In some aspects, the emitting layer of the invention can be formed using the mixture of a carbazole polymer host and a guest emitter. The polymer carbazole hole could be CZ-I-25, YZ-I-135, CZ-I-141, YZ-I-57, or YZ-I-63. The guest emitter could be one or more phosphorescent metal complexes further described below.

The norbornene monomers, polymers and copolymers of the present inventions can be doped with phosphorescent metal complexes as guests or co-polymerized with metal phosphorescent complexes containing a polymerizable norbornenyl group. The phosphorescent dopant is preferably a metal complex comprising at least one metal selected from the group consisting of Ir, Rd, Pd, Pt, Os and Re, and the like. More specific examples of the phosphorescent dopants include but are not limited to metal complexes such as tris(2-phenylpyridinato-N,$C^2$) ruthenium, bis(2-phenylpyridinato-N,$C^2$) palladium, bis(2-phenylpyridinato-N,$C^2$) platinum, tris(2-phenylpyridinato-N,$C^2$) osmium, tris(2-phenylpyridinato-N,$C^2$) rhenium, octaethyl platinum porphyrin, octaphenyl platinum porphyrin, octaethyl palladium porphyrin, octaphenyl palladium porphyrin, iridium(III) bis[(4,6-difluorophenyl)-pyridinato-N,$C^{2'}$]picolinate (Firpic), tris-(2-phenylpyridinato-N,$C^2$)iridium Ir(ppy)$_3$), green material bis-(2-phenylpyridinato N,$C^2$)iridium(acetylacetonate) (Ir(ppy)$_2$(acac), and red material 2,3,7,8,12,13,17,18-octaethyl-21H,23H-porphine platinum(II) (PtOEP) as well as other known to those skilled in the art of OLEDs and metallo-organic chemistry. In one preferred embodiment, the guest emitter is Ir(ppy)$_3$ The light-emitting layer can be spin coated from solutions comprising a solvent, one or more of the monomeric or polymeric compounds having Formulas I, Ia, Ib, II, IIa, or IIb, and one or more of the phosphorescent metal complexes described on top of a cross-linked hole-transport layer. Alternatively, the emitting layer can also be formed via thermal coevaporation.

In one embodiment, there can be an evaporated hole blocking layer and/or electron injecting layer on the top of the emitting layer. In many embodiments, the hole blocking layer can be bathocuproine (2,9-dimethyl-4,7-diphenyl-1,10-phenanthroline) (BCP) (below).

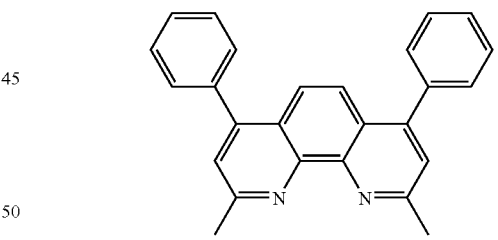

Other materials with charge carrier mobilities of >$10^{-6}$ cm$^2$V$^{-1}$ s$^{-1}$ and electron affinities comparable to BCP, ~3.2 eV and high ionization potentials (~6.5-6.7 eV) can also be used (as described in the review article by Kulkarni AP, Tonzola CJ, Babel A, et al.

Chem Mater 16 Issue: 23 Pages: 4556-4573, 2004, incorporated herein by reference. An electron injecting layer can be deposited on top of the hole blocking layer. The electron injecting layer could be an alkali metal fluoride or a metal oxide. In some embodiments, the electron injecting layer is any of LiF, CsO$_2$, MnO, or MoO$_3$. The electron injecting layer can be capped with metal cathode. In one embodiment, the metal cathode can be Al.

Polymer light-emitting diodes (PLEDs) are organic light emitting diodes wherein the organic component is an organic polymeric material. PLEDs that comprise the polymers of Formulas II, IIa, or IIb, in which the polymer can act as host to a phosphor guest, offer several advantages over small-molecule systems, some of which include the ability to tune charge transport characteristics, enhanced device stability and efficiency, and the possibility of simple deposition by solution processing methods such as spin coating.

In a related embodiment, the invention relates to the following novel compounds, whose synthesis is described in the Examples below. These compounds are used in the Examples below as synthetic intermediates for attaching desired X—Y—Z groups to the norbornenyl/M₁/M₂/M₃ groups, in order prepare the monomers and polymers described herein:

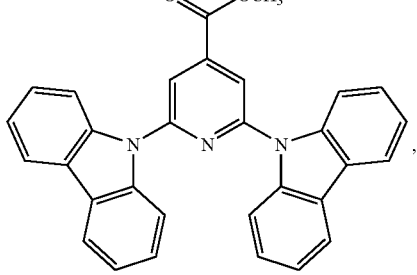

,

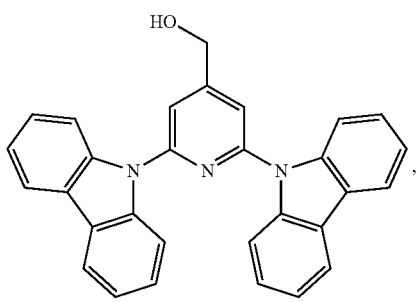

,

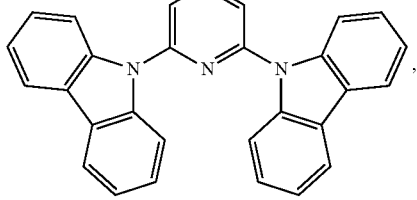

,

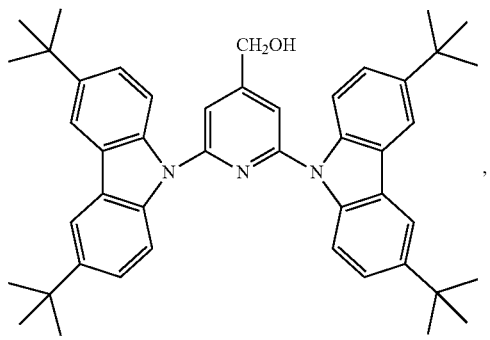

,

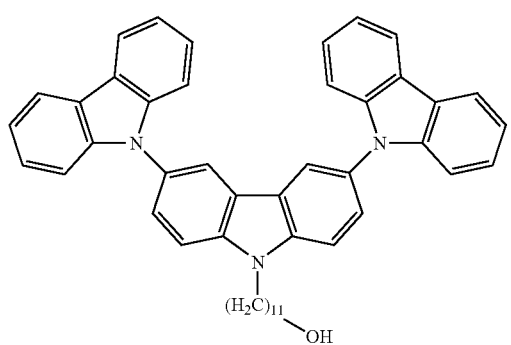

or

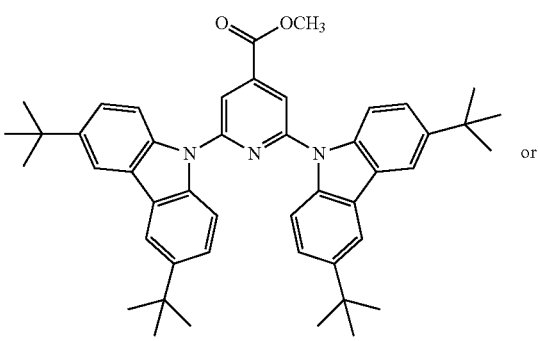

or

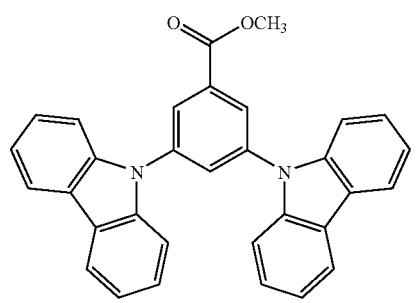

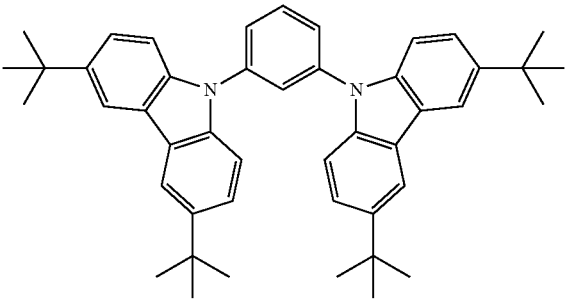

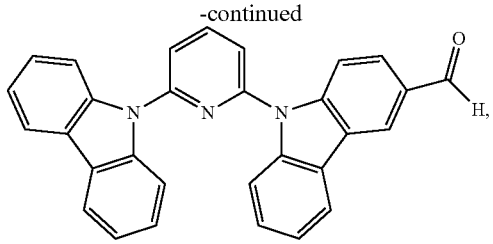

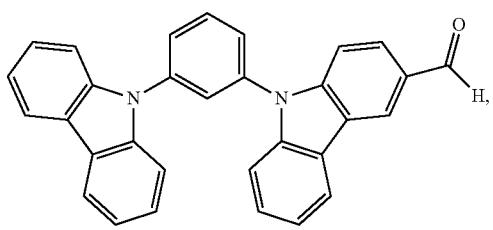

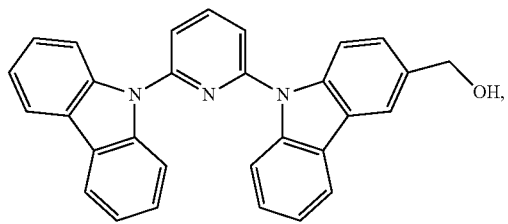

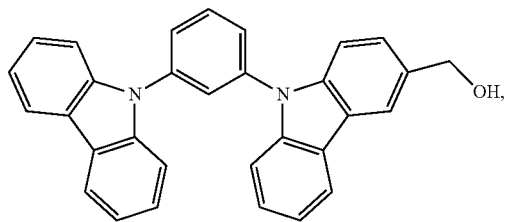

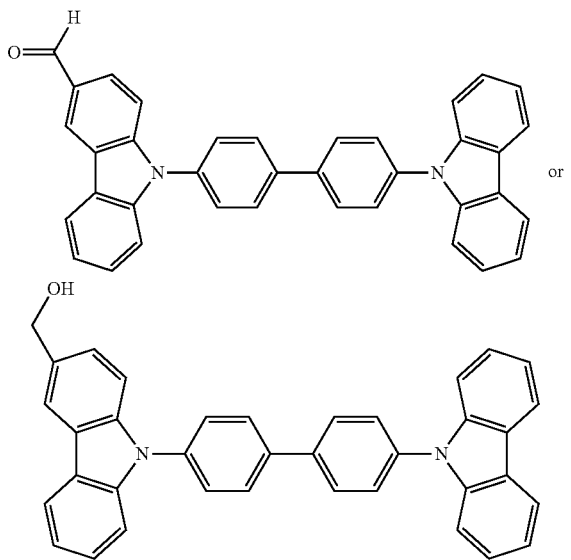

It would be obvious to one of ordinary skill in the art how to prepare many substituted variations of these same compounds by merely employing alternatively substituted aromatic starting materials in synthetic procedures analogous to those described in the Examples below.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g. amounts, temperature, etc.) but so me errors and deviations should be accounted for. Unless indicated otherwise indicated, parts are parts by weight, temperature is in ° C. or is at ambient temperature and pressure is at or near atmospheric.

Preparative Example 1

Synthesis of -3,6-di-tert-butylcarbazole (YZ-I-1)

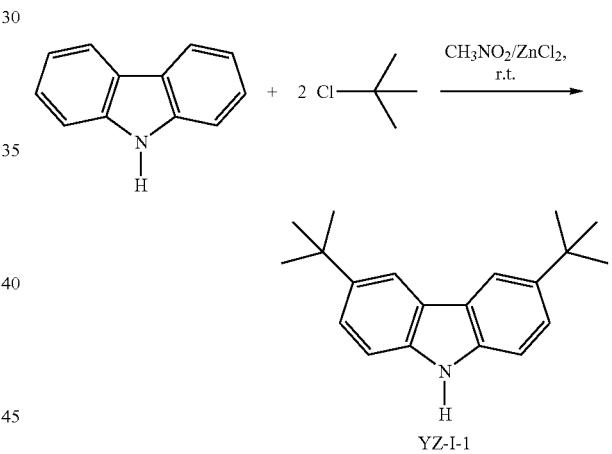

To a solution of carbazole (6.6 g, 39.5 mmol) and zinc (II) chloride (16.2 g, 118.8 mmol) in nitromethane (100.0 ml) was added dropwise 2-chloro-2-methylpropane (11.1 g, 120.0 mmol) under nitrogen atmosphere and stirring. The addition of 2-chloro-2-methylpropane was carried out over a 15 minute period. The mixture was stirred at room temperature for 24 hours. Water (100.0 ml) was then added. The product was extracted with dichloromethane (3×60.0 ml). The organic layer was washed with water (3×100.0 ml), and then dried with MgSO$_4$, and dichloromethane was evaporated under vacuum. The product was purified by recrystallization from hot hexane to afford a white product crystal in the amount of 5.0 g (in 45.0% yield).

$^1$H NMR (CDCl$_3$): δ 8.06 (d, 2H$_{Cz}$, J=1.6 Hz), 7.83 (s, br, 1H, NH), 7.45 (dd, 2H$_{Cz}$, J$_1$=8.8 Hz, J$_2$=1.6 Hz), 7.30 (d, 2H$_{Cz}$, J=8.8 Hz), 1.45 (s, 18H, 9×CH$_3$). $^{13}$C NMR (CDCl$_3$): δ 142.04, 137.84, 123.38, 123.18, 116.06, 109.88, 24.78, 32.13.

Preparative Example 2

Synthesis of 3,6-di-tert-butyl-9-(2-hydroxy ethyl) carbazole (YZ-I-69)

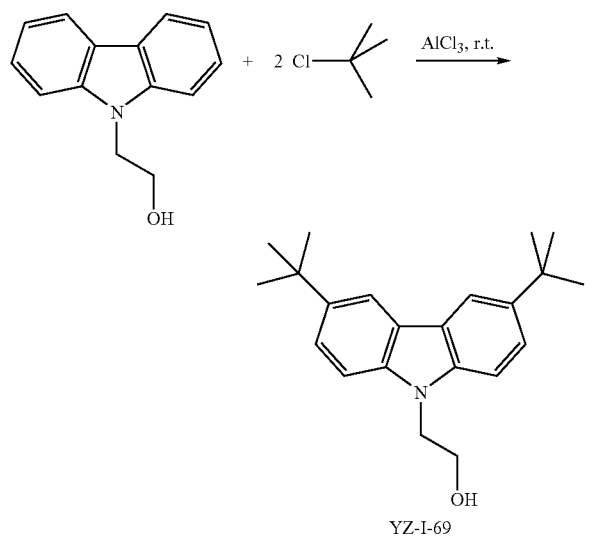

YZ-I-69

To a solution of 9-(2-hydroxy ethyl)carbazole (1.65 g, 7.81 mmol) in 2-chloro-2-methylpropane (25.0 ml) was added aluminum trichloride (0.54 g, 4.05 mmol) at room temperature under nitrogen atmosphere and stirring. After 1 minute, the addition of AlCl₃, insoluble 9-(2-hydroxyethyl)carbazole disappeared. The reaction was carried out at room temperature for 25 minutes, and water (20.0 ml) was added. The product was extracted with ethyl acetate (3×20.0 ml). The organic layer was washed with water (3×60.0 ml), and then ethyl acetate was evaporated under vacuum. The product was applied to a silica gel column [ethyl acetate/hexanes (3.5: 6.5)] to yield 2.1 g (84.0%) of a white solid after recrystallization from dichloromethane/hexanes.

$^1$H NMR (CDCl₃): δ 8.09 (d, 2H$_{Cz}$, J=2.4 Hz), 7.50 (dd, 2H$_{Cz}$, J₁=8.4 Hz, J₂=2.4 Hz), 7.35 (d, 2H$_{Cz}$, J=8.4 Hz), 4.42 (t, 2H, OCH₂, J=5.6 Hz), 4.03 (t, 2H, NCH₂, J=5.6 Hz). $^{13}$C NMR (CDCl₃): δ 141.87, 139.02, 123.38, 122.76, 116.22, 108.04, 61.74, 45.65, 34.77, 32.14. Analysis Calculated for C₂₂H₂₉NO: C, 81.69; H, 9.04; N, 4.33. Found: C, 81.55; H, 9.15; N, 4.30.

Preparative Example 3

Synthesis of 1,3-Bis(3,6-di-tert-butylcarbazol-9-yl)benzene (YZ-I-73)

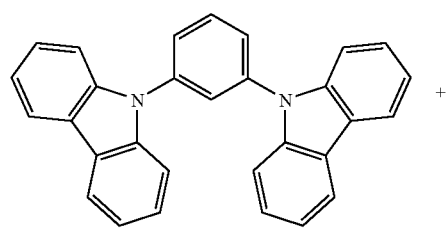 +

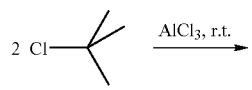

YZ-I-73

To a solution of 1,3-di(carbazol-9-yl)benzene (1.0 g, 2.45 mmol) in 2-chloro-2-methylpropane (10.0 ml) was added aluminum trichloride (0.32 g, 2.40 mmol) at room temperature under nitrogen atmosphere and stirring. After the addition of AlCl₃, insoluble 1,3-di(carbazol-9-yl)benzene disappeared within minutes. The green solid appeared after 5 minutes of reacting at room temperature. The reaction was carried out at room temperature for another 10 minutes. TLC showed that the reaction was finished. After which, water (20.0 ml) was added and the green solid became white. The solid product was collected with filtration and washed with methanol. The product was purified by recrystallization from acetone/THF/methanol to yield a white solid in the amount of 1.23 g (79.4%).

$^1$H NMR (CDCl₃): δ 8.13 (s, 4H$_{Cz}$), 7.77 (m, 2H, H$_{Bz}$), 7.63 (dd, 2H$_{Bz}$, J₁=8.0 Hz, J₂=2.0 Hz), 7.50 (m, 8H$_{Cz}$), 1.45 (s, 36H, 12×CH₃). $^{13}$C NMR (CDCl₃): δ 143.01, 139.51, 138.76, 130.77, 124.74, 124.27, 123.63, 123.42, 116.23, 109.08, 34.84, 32.10. Anal. Calcd for C₄₆H₅₂N₂: C, 87.29; H, 8.28; N, 4.43. Found: C, 87.03; H, 8.25; N, 4.41.

Preparative Example 4

Synthesis of 9-(4-(bicycle[2,2,1]hept-5-en-2-yl)butyl)-3,6-di-tert-butylcarbazole (YZ-I-79)

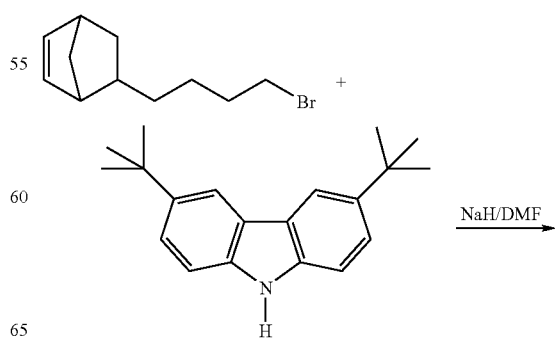

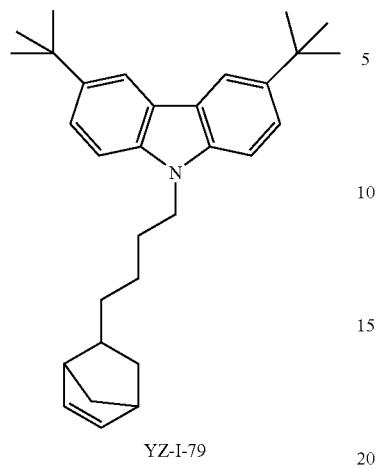

YZ-I-79

To a solution of 3,6-di-tert-butylcarbazole (1.0 g, 3.58 mmol) and 5-(4-bromobutyl)bicycle[2,2,1]hept-2-ene (0.82 g, 3.58 mmol) in DMF (16.0 ml) was slowly added NaH (0.24 g, 10.00 mmol) at room temperature under $N_2$ and stirring. The reaction was carried out at room temperature for 35 minutes. After which, water (50.0 ml) was added. The water solution was extracted with dichloromethane (3×40.0 ml). The dichloromethane solution was washed with water (4×50.0 ml). After removal of solvents, the crude product was purified by silica gel column using hexanes/ethyl acetate (9.5:0.5) as eluent. The product fraction was rotovapped to produce a viscous lightly yellow oil. The oil was dried under vacuum overnight to produce a yellowish-brown crystalline product that was subsequently isolated by vacuum filtration with water and dried overnight under vacuum. The dried product as an off-white crystalline solid was obtained in 1.25 g (81.7%) yield.

$^1$H (300 MHz, $CDCl_3$): δ8.10-8.17 (m, 2H), 7.49-7.57 (dd, J=6.58, 2.03 Hz, 2H), 7.29-7.37 (m, 2H), 5.87-6.17 (m, 2H), 4.23 (t, J=7.28 Hz, 2H), 2.71-2.83 (m, 2H), 0.44-2.04 (m, 29H).

Preparative Example 5

Synthesis of Poly[9-(6-(carbazol-9-yl)pyridine-2-yl)carbazol-3-yl)methylbicyclo[2,2,1]hept-5-ene-2-carboxylate] (YZ-I-63)

Synthesis Scheme 1(mCPy side-chain)

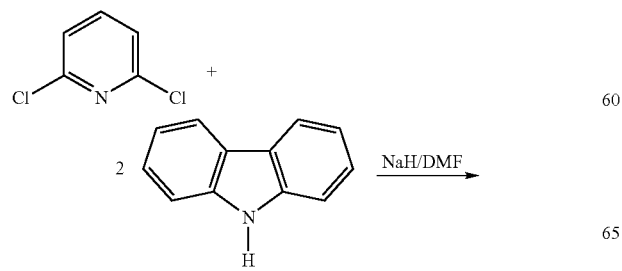

NaH/DMF

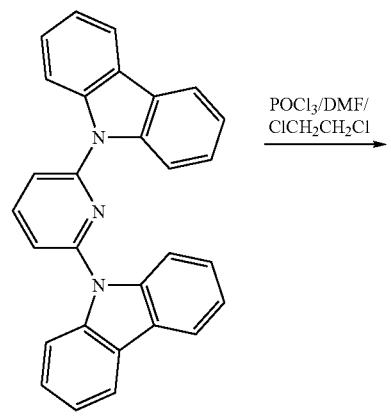

POCl$_3$/DMF/ClCH$_2$CH$_2$Cl

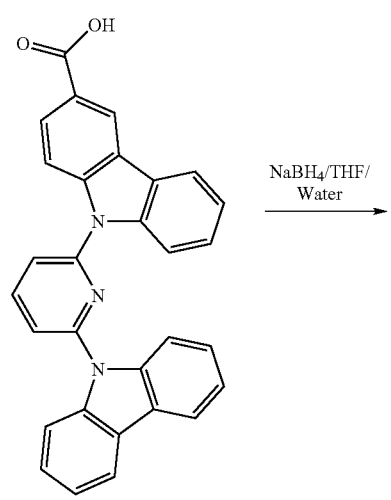

NaBH$_4$/THF/Water

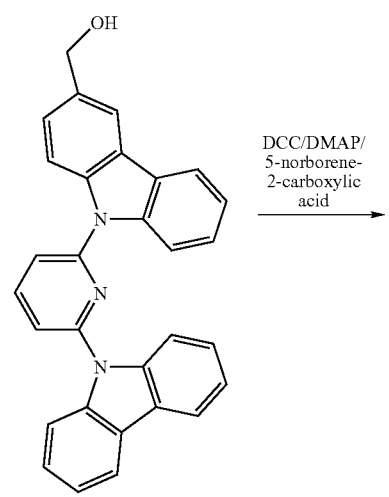

DCC/DMAP/5-norborene-2-carboxylic acid

-continued

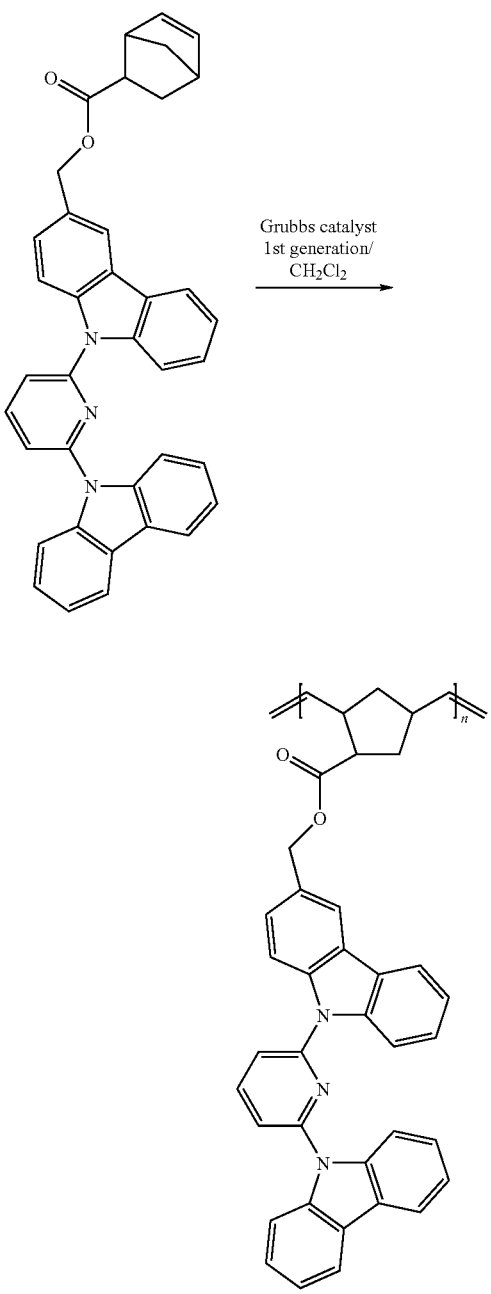

Step 1: 2,6-Di(carbazol-9-yl)pyridine (YZ-I-27)

To a solution of carbazole (97.0 g, 0.58 mol) and 2,6-dichloropyridine (41.0 g, 0.28 mol) in dry DMF (200.0 ml) was slowly added NaH (20.0 g, 0.83 mol) at room temperature under nitrogen atmosphere and stirring. The addition of NaH was taken over 60 minutes. After the addition of NaH, the mixture was heated to 160° C. and kept at this temperature for 12 hours. After cooling, water (300.0 ml) was added into the reaction mixture. The product as a brown solid was collected by filtration. The crude product was purified with recrystallization from acetone/water to give 92.2 g (81.3 g) of product.

$^1$H NMR (CDCl$_3$): δ 8.13 (m, 4H$_{Cz}$, 1 H$_{Py}$), 8.02 (d, 4H$_{Cz}$, J=8.4 Hz), 7.64 (d, 2H$_{Py}$, J=7.6 Hz), 7.42 (td, 4H$_{Cz}$, J$_1$=8.4 Hz, J$_2$=0.8 Hz), 7.30 (td, 4H$_{Cz}$, J$_1$=8.4 Hz, J$_2$=0.8 Hz), 1.45 (s, 18H, 9×CH$_3$). $^{13}$C NMR (CDCl$_3$): δ 151.34, 140.21, 139.30, 126.21, 124.41, 121.11, 120.02, 114.82, 111.84. MS-EI (m/z): [M]$^+$ calcd for C$_{29}$H$_{19}$N$_3$: 409.2. Found, 409.2.

Step 2: 9-(6-(carbazol-9-yl)pyridine-2-yl)carbazole-3-carbaldehyde (YZ-I-31)

To a solution of 2,6-di(carbazol-9-yl)pyridine, prepared above in step 1, (10.0 g, 24.4 mmol) in 1,2-dichloroethane (80.0 ml) was slowly added POCl$_3$/DMF (32.0 g/16.0 g). POCl$_3$/DMF was made by the addition of POCl$_3$ into DMF at 0° C. at room temperature under nitrogen atmosphere and stirring. After the addition of POCl$_3$/DMF, the reaction mixture was heated to 110° C. and kept at this temperature for 72 hours. After cooling, the reaction mixture was slowly added into an ice-bath cooled KOH water solution (500.0 ml of water with 100 g of KOH). After addition, the reaction mixture was stirred for 60 minutes. The water solution was extracted with ethyl acetate (3×100 ml). The organic extracted solution was washed with water until a pH=7 was obtained. The removal of solvent, crude product was purified by silica gel column with dichloromethane:hexanes:ethyl acetate (5:4.5:0.5) as the solvent mixture. After removal of the solvent mixture, the product was recrystallized from THF/water to give 4.3 g (40.3%) of pure product.

$^1$H NMR (CDCl$_3$): δ 10.11 (s, 1H, CHO), 8.65 (d, 1H$_{Cz}$, J=1.6 Hz), 8.20 (m, 3H$_{Cz}$, 1 H$_{Py}$), 8.00 (m, 5H$_{Cz}$), 7.73 (d, 1H$_{Py}$, J=8.0 Hz), 7.61 (d, 1H$_{Py}$, J=8.0 Hz), 7.48 (m, 1H$_{Cz}$), 7.41 (m, 3H$_{Cz}$), 7.33 (m, 2 HO. $^{13}$C NMR (CDCl$_3$): δ 191.45, 151.74, 150.34, 143.05, 140.60, 140.19, 139.17, 130.23, 127.84, 127.21, 126.30, 124.55, 122.99, 122.09, 121.38, 120.52, 120.12, 117.90, 115.88, 115.34, 112.05, 111.92, 111.74. MS-EI (m/z): [M]$^+$ calcd for C$_{30}$H$_{19}$N$_3$O: 437.2. Found, 437.2.

Step 3: 9-(6-(carbazol-9-yl)pyridine-2-yl)carbazol-3-yl)methanol (YZ-I-33)

To a solution of 9-(6-(carbazol-9-yl)pyridine-2-yl)carbazole-3-carbaldehyde, prepared above in step 2, (4.0 g, 9.14 mmol) in THF (150.0 ml) was slowly added NaBH4 (1.7 g, 44.94 mmol in water (4.0 ml)) at room temperature under nitrogen atmosphere and stirring. The reaction was kept at this temperature for 30 minutes. Water (150 ml) was then added. The product was extracted with ethyl acetate (3×50 ml). After removal of the ethyl acetate, the crude product was purified by silica gel column with dichloromethane/ethyl acetate (9.5:0.5) as the solvent mixture. After removal of the solvent mixture, the product was recrystallized from THF/hexanes to give 3.6 g (89.6%) pure product.

$^1$H NMR (CDCl$_3$): δ 8.12 (m, 4H$_{Cz}$, 1 H$_{Py}$), 8.01 (m, 4H$_{Cz}$), 7.62 (m, 2H$_{Py}$), 7.40 (m, 4H$_{Cz}$), 7.34 (m, 3 HO. $^{13}$C NMR (CDCl$_3$): δ 151.33, 151.22, 140.25, 139.60, 139.27, 138.92, 126.36, 126.21, 125.73, 124.59, 124.41, 124.28, 121.23, 121.14, 120.08, 120.03, 118.85, 114.85, 114.69, 112.05, 111.88, 111.81, 65.81. MS-EI (m/z): [M]$^+$ calcd for C$_{30}$H$_{21}$N$_3$O: 439.2. Found, 439.2.

Step 4: 9-(6-(carbazol-9-yl)pyridine-2-yl)carbazol-3-yl)methylbicyclo[2,2,1]hept-5-ene-2-carboxylate (YZ-I-39)

To a solution of 9-(6-(carbazol-9-yl)pyridine-2-yl)carbazol-3-yl)methanol, prepared above in step 3, (1.5 g, 3.41 mmol), DCC (1.1 g, 5.33 mmol) and 5-norbornene-2-carboxylic acid (1.0 g, 7.24 mmol) in THF (20.0 ml) was added DMAP (0.1 g, 0.82 mmol) at room temperature under nitrogen atmosphere and stirring. The reaction was carried out at this temperature for 20 hours. A white solid from DCC was filtered off and the solid was washed with THF. The THF solution was combined, after removal of THF, methanol/water (9:1 in volume) was added into glassy solid product and the mixture was stirred for overnight. A white solid product was obtained by filtration. The product was purified by silica gel column using toluene as the solvent. An exo-monomer (0.37 g), endo-monomer (1.08 g) and endo-exo mixture monomer (0.06 g) were obtained. The total yield was 79.0%.

$^1$H NMR (CDCl$_3$) for exo-monomer: δ 8.12 (m, 4H$_{Cz}$, 1 H$_{Py}$), 8.01 (m, 4H$_{Cz}$), 7.62 (m, 2 Hp), 7.40 (m, 4H$_{Cz}$), 7.34 (m, 3H$_{Cz}$), 6.12 (m, 1H, C=C—H), 6.08 (m, 1 H, C=C—H), 5.30 (s, 2H, OCH$_2$), 3.07 (s, br, 1H), 2.91 (s, br, 1H), 2.29 (m, 1H), 1.95 (m, 1H), 1.57 (m, 1H), 1.37 (m, 2H). $^{13}$C NMR (CDCl$_3$) for exo-monomer: δ 175.94, 151.37, 151.16, 140.27, 139.62, 139.27, 139.16, 137.89, 135.59, 129.02, 126.90, 126.44, 126.21, 124.51, 124.42, 124.18, 121.27, 121.15, 120.39, 120.14, 120.04, 114.94, 114.74, 111.99, 111.87, 111.81, 66.80, 46.71, 46.42, 43.29, 41.72, 30.49. $^1$H NMR (CDCl$_3$) for endo-monomer: δ 8.12 (m, 4H$_{Cz}$, 1 H$_{Py}$), 8.01 (m, 4 HO, 7.62 (m, 2H$_{Py}$), 7.40 (m, 4H$_{Cz}$), 7.34 (m, 3H$_{Cz}$), 6.18 (m, 1H, C=C—H), 5.89 (m, 1H, C=C—H), 5.25 (q, 2H, OCH$_2$), 3.24 (s, br, 1H), 2.91 3.01 (m, 1H), 2.90 (s, br, 1H), 1.91 (m, 1H), 1.48 (m, 1H), 1.42 (m, 1H), 1.26 (m, 1H). $^{13}$C NMR (CDCl$_3$) for endo-monomer: δ 174.45, 151.34, 151.16, 140.25, 139.60, 139.25, 139.09, 137.59, 132.20, 129.13, 126.85, 126.40, 126.21, 124.45, 124.41, 124.19, 121.25, 121.14, 120.28, 120.11, 120.03, 114.90, 114.72, 111.91, 111.87, 111.80, 66.52, 49.67, 45.87, 43.46, 42.64, 29.37. MS-EI (m/z): [M]$^+$ calcd for C$_{38}$H$_{29}$N$_3$O$_2$: 559.2. Found, 559.3. Anal. Calcd for C$_{38}$H$_{29}$N$_3$O$_2$: C, 81.55; H, 5.22; N, 7.51. Found: C, 81.30; H, 5.30; N, 7.50.

Step 5: Poly[9-(6-(carbazol-9-yl)pyridine-2-yl)carbazol-3-yl)methylbicyclo[2,2,1]hept-5-ene-2-carboxylate] (YZ-I-63

To a solution of 9-(6-(carbazol-9-yl)pyridine-2-yl)carbazol-3-yl)methyl-bicyclo-[2,2,1]hept-5-ene-2-carboxylate, prepared above in step 4, (0.515 g, 0.920 mmol) in dichloromethane (6.0 ml) was added a 1$^{st}$ generation Grubbs catalyst (7.5 mg, 0.0092 mmol in CH$_2$Cl$_2$ (3.0 ml)) at room temperature under stirring in a glove box. The reaction was carried out at room temperature for 24 hours. The reaction vial was taken out from the glove box. Ethyl vinyl ether (2 ml) was added to reaction mixture. The reaction mixture was stirred for 30 minutes. A polymer dichloromethane solution was added to methanol (100.0 ml) to give a white polymer solid. The white solid product was collected by filtration. The reprecipitation procedure in dichloromethane/methanol was then repeated five times. After filtration and drying in a vacuum, the final product as a white solid in the amount of 0.46 g (89.3%) was obtained.

$^1$H NMR (CDCl$_3$): δ 8.00 (m, br, 9H), 7.24 (m, br, 9H$_{Cz}$), 5.07 (m, br, 4H), 3.00 to 1.00 (m, br, 7H). Anal. Calcd for C$_{38}$H$_{29}$N$_3$O$_2$: C, 81.55; H, 5.22; N, 7.51. Found: C, 81.38; H, 5.20; N, 7.51. GPC (THF): M$_w$=48000, M$_n$=35000, PDI=1.4.

Preparative Example 6

Synthesis of Poly[(9-(3-carbazol-9-yl)phenyl)carbazol-3-yl)methyl bicyclo[2,2,1]hept-5-ene-2-carboxylate] (YZ-I-57)

Synthesis Scheme 2 (mCP side-chain)

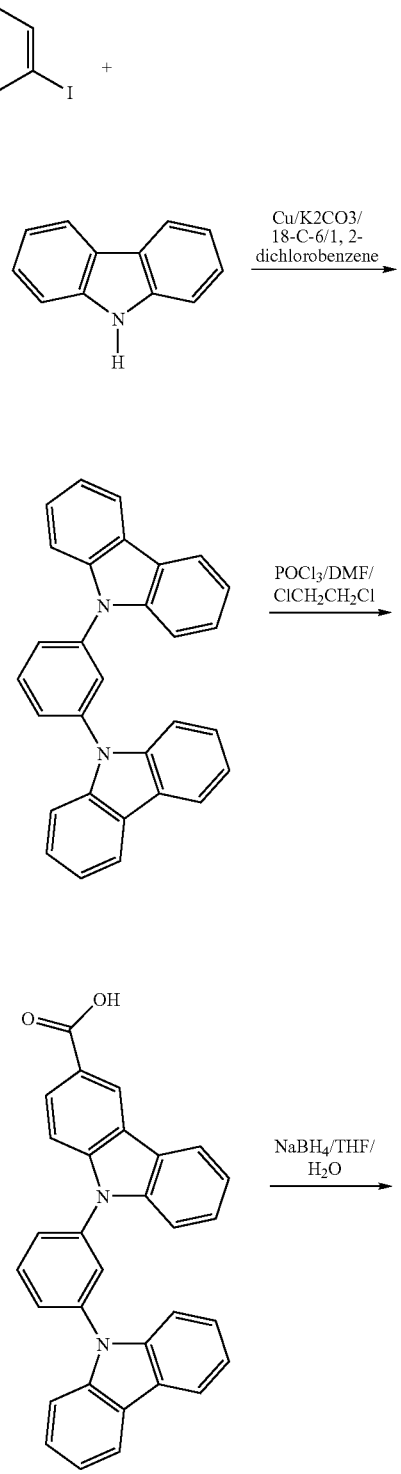

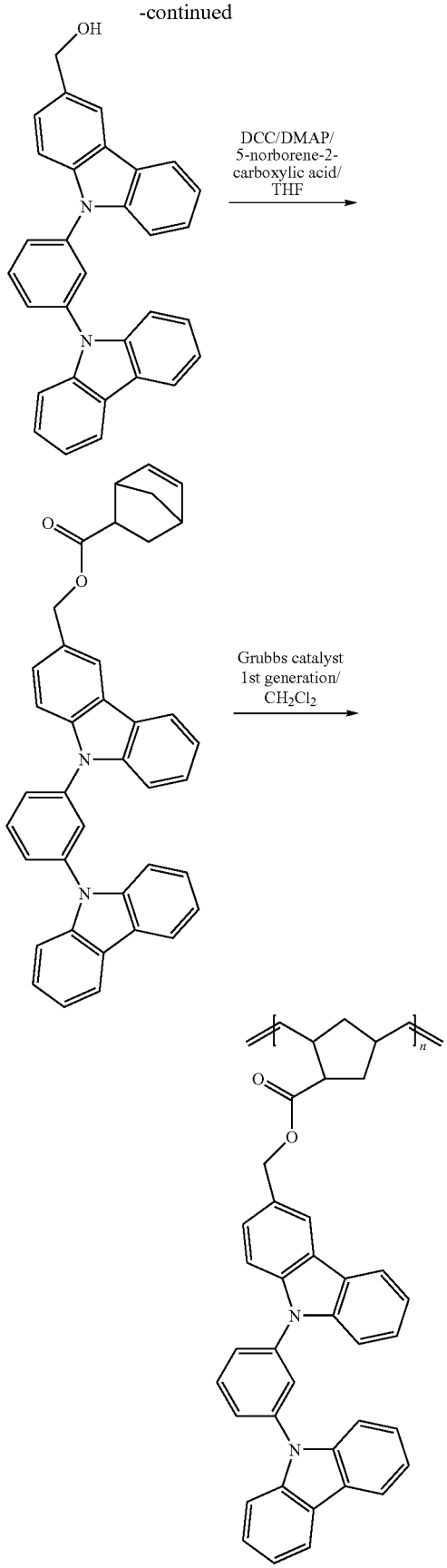

Step 1: 1,3-Di(carbazol-9-yl)benzene (YZ-I-35)

To a solution of 1,3-diiodobenzene (50.0 g, 0.152 mol), carbazole (55.0 g, 0.329 mol), Cu (40.0 g, 0.630 mol) and 18-crown-6 (0.5 g) in 1,2-dichlorobenzene (200.0 ml) was added potassium carbonate (150.0 g, 1.085 mol) under nitrogen and stirring. The reaction was carried out at 190° C. for 12 hours. After cooling, the reaction mixture was filtrated. The solid residues were carefully washed with THF. Then, THF and 1,2-dichlorobenzene were evaporated from the combined filtration solution. The crude product was purified by recrystallization from acetone/methanol to give 47.0 g (75.7%) in yield.

$^1$H NMR (CDCl$_3$): δ 8.15 (d, 4H$_{Cz}$, J=7.2 Hz), 7.83, (2H$_{Bz}$), 7.70 (m, 2H$_{Bz}$), 7.54 (d, 4H$_{Cz}$, J=7.2 Hz), 7.45 (td, 4H$_{Cz}$, J$_1$=7.2 Hz, J$_2$=1.6 Hz), 7.30 (td, 4H$_{Cz}$, J$_1$=7.2 Hz, J$_2$=1.6 Hz). $^{13}$C NMR (CDCl$_3$): δ 140.41, 139.18, 131.04, 126.01, 125.70, 125.18, 123.45, 120.32, 120.20, 109.58. MS-EI (m/z): [M]$^+$ calcd for C$_{30}$H$_{20}$N$_2$: 408.2. Found, 408.1.

Step 2: 9-(3-carbazol-9-yl)phenyl)carbazole-3-carbaldehyde (YZ-I-41)

To a solution of 1,3-Di(carbazol-9-yl)benzene (12.0 g, 29.38 mmol), prepared above in step 1, in 1,2-dichloroethane (40.0 ml) was added POCl$_3$/DMF which was prepared from POCl$_3$ (4.5 g, 29.38 mmol) and DMF (2.2 g, 29.38 mmol) at room temperature under nitrogen and stirring. The reaction was heated to 90° C. and carried out at this temperature for 12 hours. After cooling, the reaction mixture was added into ice-water (300.0 ml). The product was extracted with ethyl acetate (2×100 ml). After removal of the solvents, the product was purified by silica gel column chromatography using toluene/ethyl acetate (9.5:0.5) as the eluent. The final pure product was obtained in the amount of 5.0 g (39.2%) after it was dried.

$^1$H NMR (CDCl$_3$): δ 10.12 (s, 1H, CHO), 8.67 (m, 1H$_{Cz}$), 8.22 (m, 1H$_{Bz}$), 8.14 (m, 1H$_{Bz}$), 7.97 (dd, 1H$_{Cz}$, J$_1$=8.8 Hz, J$_2$=1.6 Hz), 7.88 (t, 1H$_{Bz}$, J=7.6 Hz) 7.78 (m, 1H$_{Bz}$, 1H$_{Cz}$), 7.68 (m, 1H$_{Cz}$), 7.58 to 7.30 (m, 11H$_{Cz}$). $^{13}$C NMR (CDCl$_3$): δ 191.68, 144.18, 141.54, 140.44, 139.63, 138.30, 131.50, 129.71, 128.21, 127.67, 126.70, 126.20, 125.85, 125.37, 123.85, 123.80, 123.64, 123.38, 121.54, 120.82, 120.51, 120.48, 110.27, 110.02, 109.52. MS-EI (m/z): [M] calcd for C$_{31}$H$_{20}$N$_2$O: 436.2. Found, 436.1.

Step 3: (9-(3-carbazol-9-yl)phenyl) carbazol-3-yl) methanol (YZ-I-43)

To a solution of 9-(3-carbazol-9-yl)phenyl)carbazole-3-carbaldehyde, prepared above in step 2, (4.0 g, 9.16 mmol) in THF (40.0 ml) was added NaBH$_4$ (1.0 g, 26.43 mmol in water (5.0 ml)) at room temperature under nitrogen and stirring. The reaction was carried out at room temperature for 30 minutes. Water (150.0 ml) was then added into the reaction mixture. The resultant product was extracted with ethyl acetate (3×50 ml). After removal of the solvents, the product was purified by recrystallization from toluene/hexanes. The final pure product was obtained in the amount of 4.0 g (100%) after it was dried.

$^1$H NMR (CDCl$_3$): δ 8.15 (m, 3H$_{Cz}$), 7.80 (m, 2H$_{Bz}$), 7.68 (m, 2H$_{Bz}$), 7.50 (t, 4H$_{Cz}$, J=8.4 Hz), 7.44 (m, 4H$_{Cz}$), 7.30 (m, 4H$_{Cz}$), 4.87 (s, 2H, OCH$_2$), 2.35 (s, 1 H, OH). $^{13}$C NMR (CDCl$_3$): δ 140.77, 140.38, 140.07, 139.21, 139.10, 132.92, 131.09, 128.89, 128.09, 126.17, 126.02, 125.75, 125.67, 125.60, 125.09, 123.60, 123.46, 123.31, 120.34, 120.22, 119.29, 109.69, 109.56, 65.92. MS-EI (m/z): [M]⁺ calcd for C₃₁H₂₂N₂O: 438.2. Found, 438.2.

Step 4: (9-(3-carbazol-9-yl)phenyl)carbazol-3-yl) methylbicycle[2,2,1]hept-5-ene-2-carboxy-late (YZ-I-45)

To a solution of (9-(3-carbazol-9-yl)phenyl)carbazol-3-yl) methanol, prepared above in step 3, (2.0 g, 4.56 mmol), 5-norborene-2-carboxylic acid (1.0 g, 7.24 mmol) and DMAP (0.1 g) in THF (20.0 ml) was added DCC (1.5 g, 7.27 mmol) at room temperature under nitrogen and stirring. The reaction was carried out at room temperature for 2 hours. The white solid from DCC was filtrated off and washed with THF. The THF was removed and methanol was added into the solid product.

The white solid product was obtained by filtration. The product was purified by silica gel column using toluene as a solvent. The exo-monomer (0.29 g), endo-monomer (0.85 g) and endo-exo mixture monomer (0.69 g) were obtained. The total yield was 71.3%. ¹H NMR (CDCl₃) for exo-monomer: δ 8.14 (m, 4H$_{Cz}$), 7.82 (m, 2H$_{Bz}$), 7.69 (m, 2H$_{Bz}$), 7.51 (m, 4H$_{Cz}$), 7.42 (m, 4H$_{Cz}$), 7.30 (m, 3H$_{Cz}$), 6.12 (m, 1H, C=C—H), 6.08 (m, 1H, C=C—H), 5.31 (s, 2H, OCH₂), 3.05 (s, br, 1H), 2.90 (s, br, 1H), 2.27 (m, 1H), 1.95 (m, 1H), 1.54 (m, 1H), 1.36 (m, 2H). ¹³C NMR (CDCl₃) for exo-monomer:

δ 175.98, 140.78, 140.38, 140.28, 139.01, 137.91, 135.60, 131.12, 128.12, 126.88, 126.28, 126.03, 125.85, 125.63, 125.12, 123.54, 123.47, 123.24, 120.89, 120.40, 120.35, 120.23, 109.72, 109.55, 66.96, 46.72, 46.44, 43.31, 41.73, 30.51. ¹H NMR (CDCl₃) for endo-monomer: δ 8.12 (m, 4H$_{Cz}$), 7.82 (m, 2H$_{Bz}$), 7.69 (m, 2H$_{Bz}$), 7.51 (m, 4H$_{Cz}$), 7.37 (m, 4H$_{Cz}$), 7.31 (m, 3H$_{Cz}$), 6.18 (m, 1H, C=C—H), 5.89 (m, 1H, C=C—H), 5.25 (q, 2H, OCH₂), 3.22 (s, br, 1H), 2.99 (m, 1H), 2.90 (s, br, 1H), 1.91 (m, 1H), 1.48 (m, 1H), 1.42 (m, 1H), 1.26 (m, 1H). ¹³C NMR (CDCl₃) for endo-monomer: δ 174.49, 140.76, 140.38, 140.21, 139.22, 139.02, 137.61, 132.20, 131.10, 128.23, 126.82, 126.24, 126.02, 125.82, 125.62, 125.11, 123.45, 123.25, 120.79, 120.42, 120.38, 120.34, 120.23, 109.70, 109.61, 109.54, 66.67, 49.67, 45.87, 43.50, 42.64, 29.38. MS-EI (m/z): [M]⁺ calcd for C₃₈H₂₉N₃O₂: 558.2. Found, 558.2. Elemental Analysis Calculated for C₃₉H₃₀N₂O₂: C, 83.85; H, 5.41; N, 5.01. Found: C, 84.12; H, 5.38; N, 5.05.

Step 5: Poly[(9-(3-carbazol-9-yl)phenyl)carbazol-3-yl)methyl bicyclo[2,2,1]hept-5-ene-2-carboxylate] (YZ-I-57)

To a solution of 9-(6-(carbazol-9-yl)pyridine-2-yl)carbazol-3-yl)methyl-bicyclo[2,2,1]hept-5-ene-2-carboxylate, prepared above in step 4, (0.515 g, 0.920 mmol) in dichloromethane (6.0 ml) was added a Grubbs catalyst 1$^{st}$ generation (7.5 mg, 0.0092 mmol in CH₂Cl₂ (3.0 ml)) at room temperature under stirring in a glove box. The reaction was carried out at room temperature for 24 hours. The reaction vial was taken out from the glove box. Ethyl vinyl ether (2 ml) was added to the reaction mixture. The reaction mixture was stirred for 30 minutes. After which a polymer dichloromethane solution was added to methanol (100.0 ml) to give a white polymer solid. The white solid product was collected by filtration. Then the reprecipitation procedure in dichloromethane/methanol was repeated five times. After filtration and drying in a vacuum, the final product was a white solid in 0.46 g (89.3%) was obtained.

¹H NMR (CDCl₃): δ 8.09 (m, br, 4H), 7.41 (m, br, 15H), 5.13 (m, br, 4H), 3.20 to 0.8 (m, br, 7H). Elemental Analysis Calculated for C₃₈H₂₉N₃O₂: C₃₉H₃₀N₂O₂: C, 83.85; H, 5.41; N, 5.01. Found: C, 83.71; H, 5.22; N, 5.03. GPC (THF): M$_w$=46000, M$_n$=35000, PDI=1.3.

Preparative Example 7

Synthesis of Compound Poly[11-(6-(9H-carbazol-9-yl)-9H-3,9'-bicarbazol-9-yl)undecyl bicyclo[2.2.1]hept-5-ene-2-carboxylate] CZ-I-25

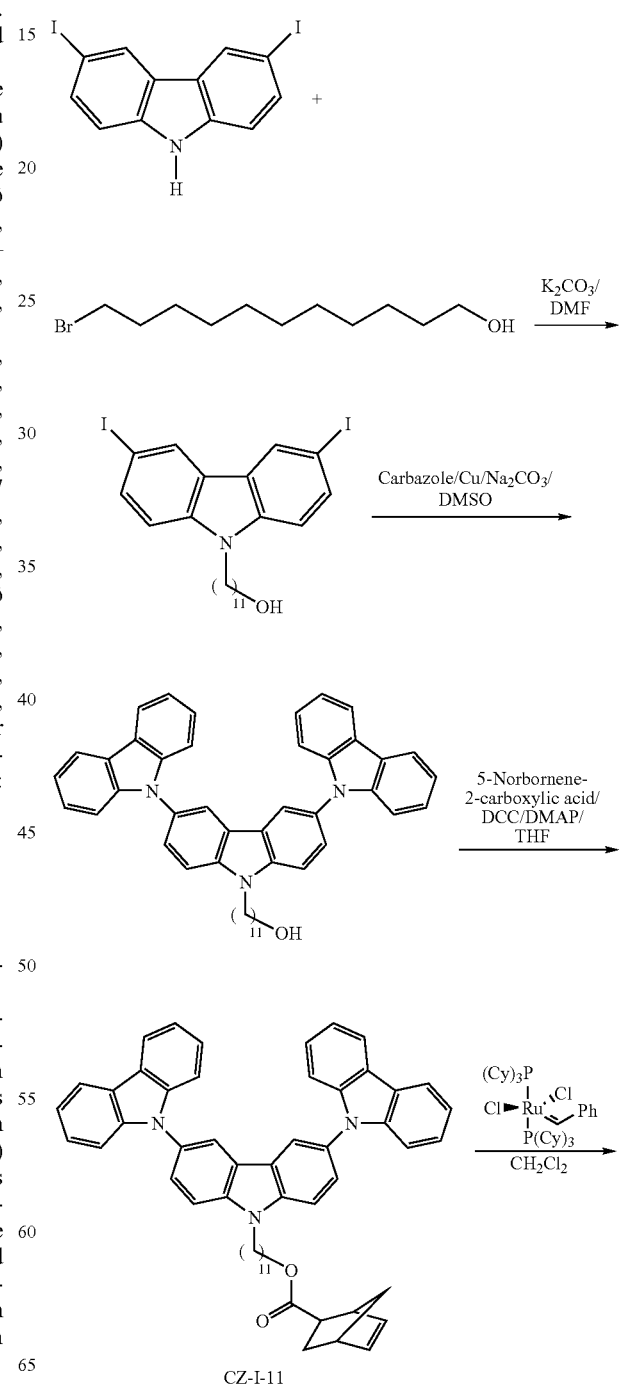

CZ-I-11

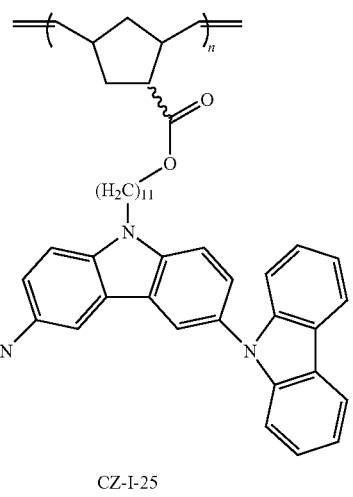

CZ-I-25

Step 1: 11-(3,6-Diiodo-9H-carbazol-9-yl)undecan-1-ol

To a solution of 3,6-diiodocarbazole (10.0 g, 23.87 mmol) and 11-bromo-1-undecanol (7.0 g, 27.87 mmol) in DMF (100.0 ml) was added $K_2CO_3$ (32.0 g, 231.33 mmol). The reaction was carried out at room temperature for 24 h. Water (300 ml) was added. The precipitate was filtered. The crude product was purified by silica gel column using Hexane/ethyl acetate (7:3) as solvent. 12.4 g (87.9%) of pure product as white solid was obtained.

$^1$H-NMR (CDCl$_3$, TMS, 500 MHZ): δ=8.32 (d, 2H$_{arom}$, J=1.5 Hz), 7.71 (dd, 2H$_{arom}$, J$_1$=1.5 Hz, J$_2$=8.5 Hz), 7.16 (dd, 2H$_{arom}$, J$_1$=1.5 Hz, J$_2$=8.5 Hz), 4.21 (t, 2H, NCH$_2$), 3.64 (m, 2H, OCH$_2$), 3.41 (t, 1H, OH), 1.81 (m, 4H, 2×CH$_2$), 1.54 (m, 4H, 2×CH$_2$), 1.30 (m, 10H, 5×CH$_2$) ppm.

Step 2: 11-(6-(9H-Carbazol-9-yl)-9H-33'-bicarbazol-9-yl)undecan-1-ol

To a solution of 11-(3,6-Diiodo-9H-carbazol-9-yl)undecan-1-ol (8.0 g, 13.6 mmol), carbazole (6.8 g, 40.7 mmol) in DMSO (50.0 ml) were added Cu (10.0 g, 157.38 mmol) and Na$_2$CO$_3$ (30.0 g, 283.05 mmol). The reaction was stirred at 180° C. for 12 h. Insoluble inorganic salts were removed by filtration and washed with THF. After removal of THF, water (250.0 ml) was added. The precipitate was collected by filtration and purified by silica gel column using toluene/ethyl acetate (7:3) as solvent. 8.1 g (91.0%) of product was obtained as white solid.

$^1$H (300 MHz, CDCl$_3$): δ8.13-8.24 (m, 5H), 7.63-7.71 (m, 4H), 7.22-7.43 (m, 13H), 4.49 (t, J=6.98 Hz, 2H), 3.62 (t, J=6.34 Hz, 2H), 2.05 (p, J=7.28 Hz, 2H), 1.23-1.77 (m, 18H), 1.18 (s, 1H). $^{13}$C{$^1$H} (75 MHz, CDCl$_3$): δ142.09, 140.42, 129.54, 126.19, 126.08, 123.62, 123.35, 123.33, 120.51, 120.07, 119.85, 110.34, 109.97, 63.31, 43.94, 33.02, 29.82, 29.79, 29.71, 29.66, 29.43, 27.66, 25.98. EI-MS (m/z): M$^+$ calcd for C$_{47}$H$_{45}$N$_3$O, 667.36. Found 667.4. Elemental Analysis Calculated for C$_{47}$H$_{45}$N$_3$O: C, 84.52; H, 6.79; N, 6.29. Found: C, 84.37; H, 6.74; N, 6.29.

Step 3: 11-(6-(9H-carbazol-9-yl)-9H-3,9'-bicarbazol-9-yl)undecyl bicyclo[2.2.1]hept-5-ene-2-carboxylate (CZ-I-11)

The purified product of prepared in step 2, (0.501 g, 0.75 mmol), 5-norbornene-2-carboxylic acid (0.235 g, 1.70 mmol) and 10 mL of dry THF were combined in a round bottom flask (with stirring) and cooled in an ice bath for 20 minutes. DCC (0.17 g, 0.82 mmol) and DMAP (0.02 g, 0.16 mmol) were weighed (on weighing paper) and added to the reaction flask. The flask was subsequently removed from the ice bath and allowed to warm to room temperature. The reaction proceeded overnight for 18 hours. The TLC showed the presence of starting material the next day, therefore more DCC (0.10 g, 0.48 mmol) was added to the reaction flask. After about 4 hours, TLC still showed the presence of the starting material. Additional 5-norbornene-2-carboxylic acid (0.02 g, 0.14 mmol) and DCC (0.04 g, 0.19 mmol) was added to the flask and the reaction was allowed to proceed overnight for 18 hours. TLC still showed the presence of starting material the next day so the reaction was stopped. The reaction mixture was filtered to remove the insoluble DCC by-product and the filtrate was rotovapped to give white precipitate. The precipitate was recrystallized (2 times) from acetone with methanol but the starting material impurity remained (as observed by TLC). Column chromatography (silica gel, hexanes:ethyl acetate=8:2) was used to purify the product followed by recrystallization from acetone with methanol and vacuum drying overnight. Solvent contamination (as observed by $^1$H NMR) required additional recrystallization from dichloromethane with methanol. The purified product was collected by vacuum filtration and dried overnight at 60° C. in a vacuum oven (for 16 hours) to give a white powder (0.42 g, 71.2%).

$^1$H (300 MHz, CDCl$_3$): δ1.22-1.69 (m, 18H), 1.83-1.96 (m, 1H), 2.05 (p, J=7.4 Hz, 2H), 2.17-2.25 (m, 1H), 2.86-2.98 (m, 1H), 3.03 (s, 1H), 3.19 (s, 1H), 5.88-5.94 (m, 1H), 6.07-6.22 (m, 1H), 7.16-7.50 (m, 13H), 7.66 (m, 4H), 8.13-8.24 (m, 5H). $^{13}$C{$^1$H} (75 MHz, CDCl$_3$): δ 175.11, 142.10, 138.29, 137.99, 132.59, 129.53, 126.20, 126.08, 126.06, 123.35, 123.33, 120.54, 120.52, 119.85, 110.34, 109.94, 64.55, 49.86, 45.96, 43.60, 42.77, 29.80, 29.76, 29.74, 29.48, 29.46, 29.44, 29.40, 28.91, 27.69, 26.19. EI-MS (m/z): M$^+$ calcd for C$_{55}$H$_{53}$N$_3$O$_2$, 787.41. Found 787.4. Elemental analysis calculated. for C$_{55}$H$_{53}$N$_3$O$_2$: C, 83.83; H, 6.78; N, 5.33. Found: C, 83.70; H, 6.72; N, 5.28.

Step 4: CZ-I-25

The purified CZ-I-11 monomer, prepared above in step 2, (0.4001 g, 0.51 mmol) was weighed into a bottle. Grubbs's first generation catalyst (0.0046 g, 5.5×10$^{-3}$ mmol) was weighed out into a separate vial. The bottle and vial were placed into a glove box. An amount of 3 mL of dry CH$_2$Cl$_2$ was added to the bottle containing monomer CZ-I-11 with stirring and then capped. Then 1 mL of dry $CH_2Cl_2$ was added to a vial containing Grubbs's first generation catalyst and shaken vigorously. Subsequently, the Grubbs's catalyst solution was quickly transferred to the bottle containing the monomer solution (while stirring) and then capped. An additional 1 mL of $CH_2Cl_2$ was added to the Grubbs's catalyst vial (for washing) and shaken. The solution was then transferred into the monomer bottle (while stirring) and then capped. The polymerization was allowed to proceed overnight for 16 hours. The reaction was quenched (outside of the glove box) with 3 mL of ethyl vinyl ether and then transferred (dropwise) into 30 mL of methanol to precipitate the polymer. The polymer was then vacuum filtered and redissolved with minimal (<3 mL) $CH_2Cl_2$ and 1 mL of ethyl vinyl ether was added. This solution was then added (dropwise) to 30 mL of methanol to precipitate the polymer. The process of isolating, dissolving, and vacuum filtering the polymer was repeated 3 more times in order to remove the Grubbs's catalyst. The final product was dried under vacuum to give a white/off-white powder (0.21 g, 52.5%).

$^1$H (300 MHz, $CDCl_3$): δ8.13-8.24 (m, 5H), 7.66 (m, 4H), 7.16-7.50 (m, 13H), 6.07-6.22 (m, 1H), 5.88-5.94 (m, 1H), 3.19 (s, 1H), 3.03 (s, 1H), 2.86-2.98 (m, 1H), 2.17-2.25 (m, 1H), 2.05 (p, J=7.4 Hz, 2H), 1.83-1.96 (m, 1H), 1.22-1.69 (m, 18H). $^{13}C\{^1H\}$ (75 MHz, $CDCl_3$): δ 175.11, 142.10, 138.29, 137.99, 132.59, 129.53, 126.20, 126.08, 126.06, 123.35, 123.33, 120.54, 120.52, 119.85, 110.34, 109.94, 64.55, 49.86, 45.96, 43.60, 42.77, 29.80, 29.76, 29.74, 29.48, 29.46, 29.44, 29.40, 28.91, 27.69, 26.19. EI-MS (m/z): $M^+$ calcd for $C_{55}H_{53}N_3O_2$, 787.41. Found 787.4. Elemental analysis calculated for $C_{55}H_{53}N_3O_2$: C, 83.83; H, 6.78; N, 5.33. Found: C, 83.70; H, 6.72; N, 5.28.

Preparative Example 8

Synthesis of Compound Poly[(1R,4R)-(2,6-bis(3,6-di-tert-butyl-9H-carbazol-9-yl)pyridin-4-yl)methyl bicyclo[2.2.1]hept-5-ene-2-carboxylate] (CZ-I-41)

Synthesis Scheme 4

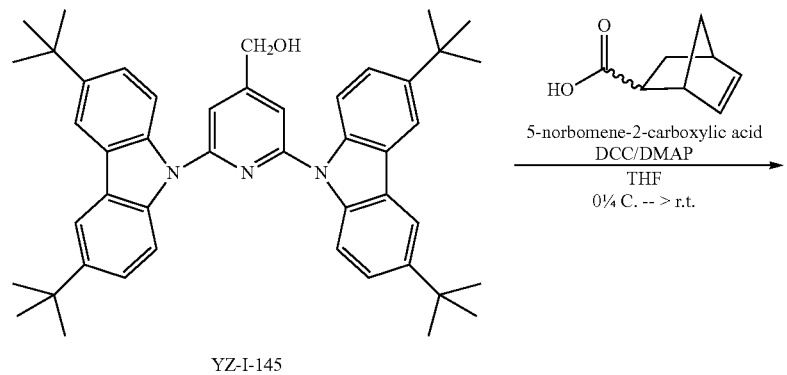

YZ-I-145

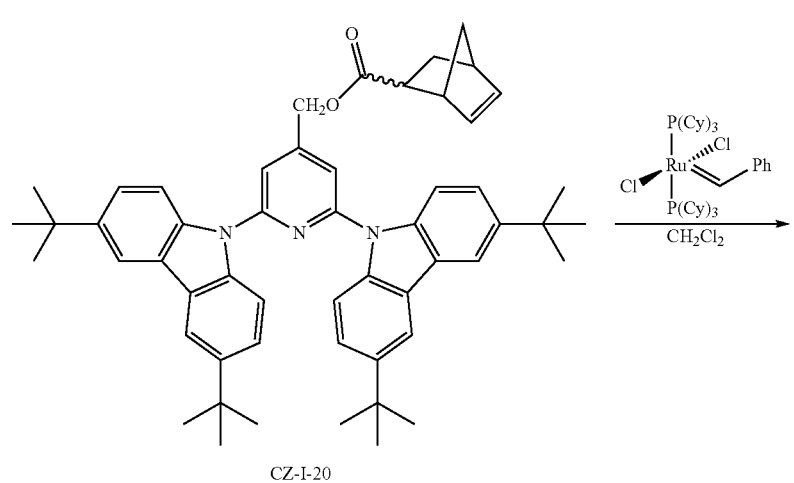

CZ-I-20

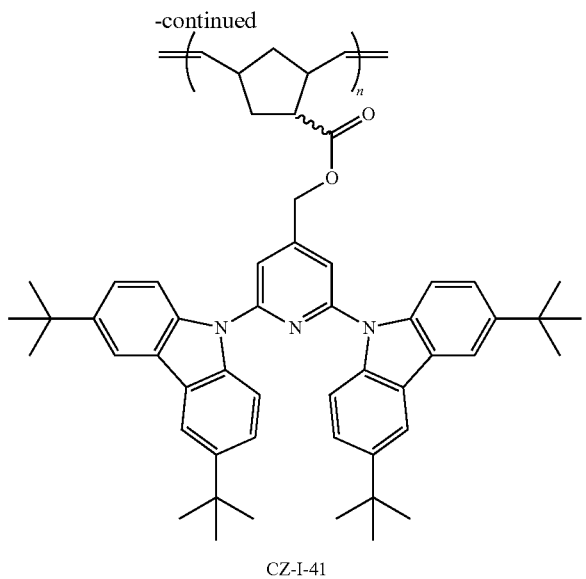

CZ-I-41

Step 1: Synthesis of (2,6-bis(3,6-di-tert-butylcarbazol-9-yl)pyridine-4-yl)methanol (YZ-I-145)

To a solution of (2,6-dibromopyridin-4-yl)methanol (1.0 g, 3.75 mmol), 3,6-di-tert-butylcarbazole (2.3 g, 8.23 mmol), Cu (2.0 g, 31.47 mmol) and 18-crown-6 (32 mg, 0.12 mmol) in 1,2-dichlorobenzene (10.0 ml), was added potassium carbonate (4.0 g, 28.94 mmol) under nitrogen and stirring. The reaction was carried out at 180° C. for 10 hours. After cooling, the reaction mixture was filtrated. The solid residues were carefully washed with THF. Then, THF and 1,2-dichlorobenzene were evaporated from the combined filtration solution. The product was purified by silica gel column chromatography using toluene as an eluent. The pure product, a yellow solid in an amount of 1.7 g (68.0%), was obtained by recrystallization from acetone/methanol/water.

$^1$H NMR (CDCl$_3$): δ 8.12 (d, 4H$_{Cz}$, J=1.2 Hz), 7.95 (d, 4H$_{Cz}$, J=8.8 Hz), 7.56 (s, 2H$_{Py}$) 7.44 (dd, 4H$_{Cz}$, J$_1$=8.8 Hz, J$_2$=1.2 Hz), 4.94 (s, 2H, OCH$_2$), 1.46 (s, 36H, 12×CH$_3$). $^{13}$C NMR (CDCl$_3$): δ 154.35, 151.82, 143.94, 137.71, 124.45, 123.84, 115.91, 111.68, 110.75, 63.76, 34.84, 32.02. EI-MS (m/z): M$^+$ calcd for C$_{46}$H$_{53}$N$_3$O, 663.4. Found 663.7. Elemental anal. calcd. for C$_{46}$H$_{53}$N$_3$O: C, 83.22; H, 8.05; N, 6.33. Found: C, 82.77; H, 8.07; N, 6.31.

Step 2: Synthesis of (1R,4R)-(2,6-bis(3,6-di-tert-butyl-9H-carbazol-9-yl)pyridin-4-yl)methyl bicyclo[2.2.1]hept-5-ene-2-carboxylate (CZ-I-20)

Purified YZ-I-145, obtained from step 1 above, (0.500 g, 0.75 mmol), 5-norbornene-2-carboxylic acid (0.235 g, 1.70 mmol) and 10 mL of dry THF were combined in a round bottom flask (with stirring) and cooled in an ice bath for 20 minutes. DCC (0.21 g, 1.01 mmol) and DMAP (0.02 g, 0.16 mmol) were weighed (on weighing paper) and added to the reaction flask. The flask was subsequently removed from the ice bath and allowed to warm to room temperature. The reaction was allowed to proceed overnight for 18 hours. The TLC showed completion of the reaction. The reaction mixture was vacuum filtered to remove the insoluble DCC byproduct and the filtrate was processed with a rotary evaporator. Methano 1 was added to the rotovapped flask to precipitate the product and the solid was isolated by vacuum filtration. The product was recrystallized from CH$_2$Cl$_2$ with methanol, isolated, and dried overnight for 16 hours under vacuum (at 60° C.). The product obtained was a white powder (0.50 g, 84.7%).

$^1$H (300 MHz, CDCl$_3$): δ8.04-8.20 (m, 4H), 7.85-8.03 (m, 4H), 7.35-7.57 (m, 6H), 6.12-6.21 (m, 1H), 5.92-5.97 (m, 1H), 5.19-5.42 (m, 2H), 3.31 (s, 1H), 3.07-3.19 (m, 1H), 2.94 (br s, 1H), 2.36-2.42 (m, 1H), 1.96-2.06 (m, 2H), 1.67 (s, 1H), 1.20-1.62 (m, 38H). $^{13}$C{$^1$H} (75 MHz, CDCl$_3$): δ 175.64, 162.61, 159.03, 152.32, 144.52, 138.41, 138.06, 124.92, 124.26, 116.29, 112.06 111.66, 64.44, 49.97, 46.04, 42.78, 35.00 32.15, 29.70. EI-MS (m/z): M$^+$ calcd for C$_{54}$H$_{61}$N$_3$O$_2$, 783.48. Found 783.6. Elemental analysis calculated. for C$_{54}$H$_{61}$N$_3$O$_2$: C, 82.72; H, 7.84; N, 5.36. Found: C, 82.51; H, 7.85; N, 5.35.

Step 3: Synthesis of (1R,4R)-(2,6-bis(3,6-di-tert-butyl-9H-carbazol-9-yl)pyridin-4-yl)methyl bicyclo[2.2.1]hept-5-ene-2-carboxylate (CZ-I-41)

The CZ-I-20 monomer, obtained from step 2 above, (0.404 g, 0.52 mmol) was weighed into a bottle. A Grubbs's first generation catalyst (0.005 g, 6.1×10$^{-3}$ mmol) was weighed out into a separate vial. The bottle and vial were placed into a glove box. Then 3 mL of dry CH$_2$Cl$_2$ was added to the bottle containing monomer CZ-I-11 with stirring and then capped. 1 mL of dry CH$_2$Cl$_2$ was added to vial containing Grubbs's first generation catalyst and shaken vigorously. Subsequently, the Grubb's catalyst solution was quickly transferred to the bottle containing the monomer solution (while stirring) and then capped. An additional 1 mL of CH$_2$Cl$_2$ was added to the Grubbs's catalyst vial (for washing) and shaken. The Grubbs's solution was then transferred into the monomer bottle (while stirring) and then capped. The polymerization was allowed to proceed overnight for 16 hours. The reaction was quenched (outside of the glove box) with 3 mL of ethyl vinyl ether and then transferred (dropwise) into 30 mL of methanol to precipitate the polymer. The polymer was then vacuum filtered and re-dissolved in minimal (<3 mL) CH$_2$Cl$_2$ and 1 mL of ethyl vinyl ether was added. This solution was then added (dropwise) to 30 mL of methanol to precipitate the polymer. The process of isolating, dissolving, re-crystallizing (from methanol) and vacuum filtering the polymer was repeated 4 more times in order to remove the Grubbs's catalyst. The final product was dried under vacuum to give a white/off-white powder (0.21 g, 52.5%).

$^1$H (300 MHz, CDCl$_3$): δ7.97-8.22 (br m, 4H), 7.69-7.97 (br m, 4H), 7.27-7.62 (br m, 6H), 4.44-5.61 (br m, 4H), 1.41-3.22 (br m, 7H), 1.35 (s, 36H). Elemental Analysis Calculated for C$_{54}$H$_{61}$N$_3$O$_2$: C, 82.72; H, 7.84; N, 5.36. Found: C, 82.35; H, 7.81; N, 5.33. Gel Permeation Chromatography (THF): M$_w$=44,000; M$_n$=22,000; PDI=1.976.

Preparative Example 9

Synthesis of Poly[9-(4-((1S,2R,4S)-bicyclo[2.2.1]hept-5-en-2-yl)butyl)-3,6-di-tert-butyl-9H-carbazole] (CZ-I-47)

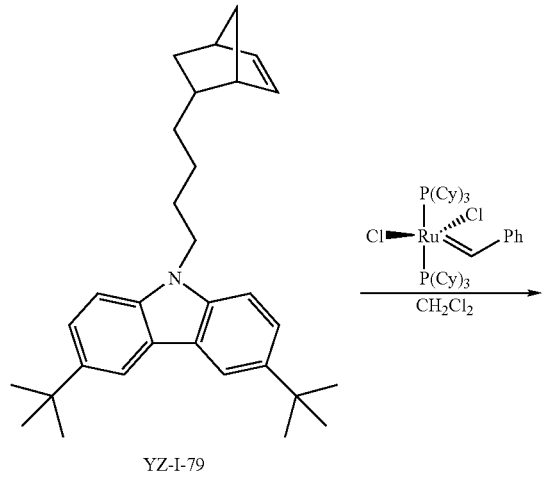

Synthesis of Poly[9-(4-((1S,2R,4S)-bicyclo[2.2.1]hept-5-en-2-yl)butyl)-3,6-di-tert-butyl-9H-carbazole] (CZ-I-47)

YZ-I-79 monomer, obtained from step 1 above, (0.5019 g, 1.17 mmol) was weighed into a bottle. A Grubbs's first generation catalyst (0.0112 g, 1.4×10$^{-2}$ mmol) was weighed out into a separate vial. The bottle and vial were placed into a glove box. 10 mL of dry CH$_2$Cl$_2$ was added to the bottle containing monomer YZ-I-79 with stirring and then capped. 1 mL of dry CH$_2$Cl$_2$ was added to vial containing the Grubb's first generation catalyst and shaken vigorously. Subsequently, the Grubbs's catalyst solution was quickly transferred to the bottle with monomer solution (while stirring) and then capped. An additional 1 mL of CH$_2$Cl$_2$ was added to the Grubbs's catalyst vial (for washing) and shaken. The Grubbs's solution was then transferred into the monomer bottle (while stirring) and then capped. The polymerization was allowed to proceed overnight for 16 hours. The reaction was quenched (outside of glove box) with 5 mL of ethyl vinyl ether, processed with a rotary evaporator to concentrate the polymer solution, and then transferred (dropwise) into 50 mL of methanol to precipitate the polymer. The polymer was then vacuum filtered and re-dissolved in minimal (<3 mL) CH$_2$Cl$_2$ and 1 mL of ethyl vinyl ether was added. This solution was then added (dropwise) to 50 mL of methanol to precipitate the polymer. The process of isolating, dissolving, re-crystallizing (from methanol) and vacuum filtering the polymer was repeated 5 more times in order to remove the Grubbs's catalyst. The final product was dried under vacuum to give a white/off-white powder (0.219 g, 43.8%).

$^1$H (300 MHz, CDCl$_3$): δ8.02-8.14 (br m, 2H), 7.31-7.53 (br m, 2H), 6.97-7.25 (br m, 2H), 5.00-5.45 (br m, 2H), 3.91-4.29 (br m, 2H), 2.59-2.99 (br m, 1H), 2.16-2.59 (br m, 2H), 1.58-2.11 (br m, 4H), 1.42 (s, 18H), 0.76-1.35 (br m, 6H). Elemental Analysis Calculated for C$_{31}$H$_{41}$N: C, 87.06; H, 9.66; N, 3.28. Found: C, 86.12; H, 9.76; N, 3.15. Gel Permeation Chromatography (THF): M$_w$=25,000; M$_n$=9,000; PDI=2.898.

Preparative Example 10

Synthesis of Compound Poly[(1S,4S)-2-(3,6-di-tert-butyl-9H-carbazol-9-yl)ethyl bicyclo[2.2.1]hept-5-ene-carboxylate] (CZ-I-56)

Synthesis Scheme 6

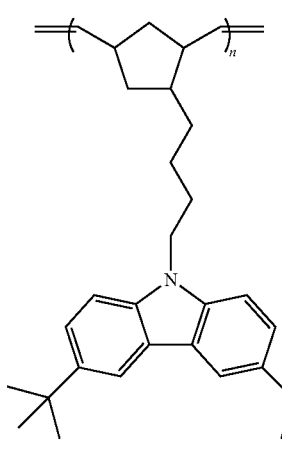

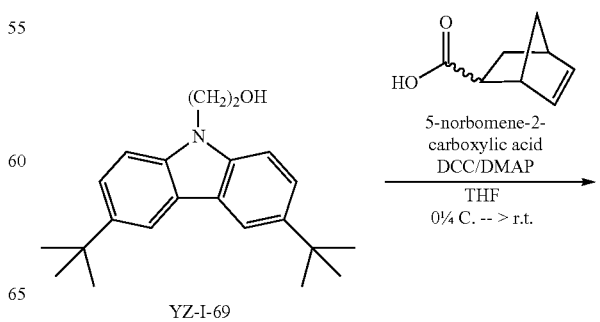

5-norbornene-2-carboxylic acid
DCC/DMAP
THF
0¼ C. → r.t.

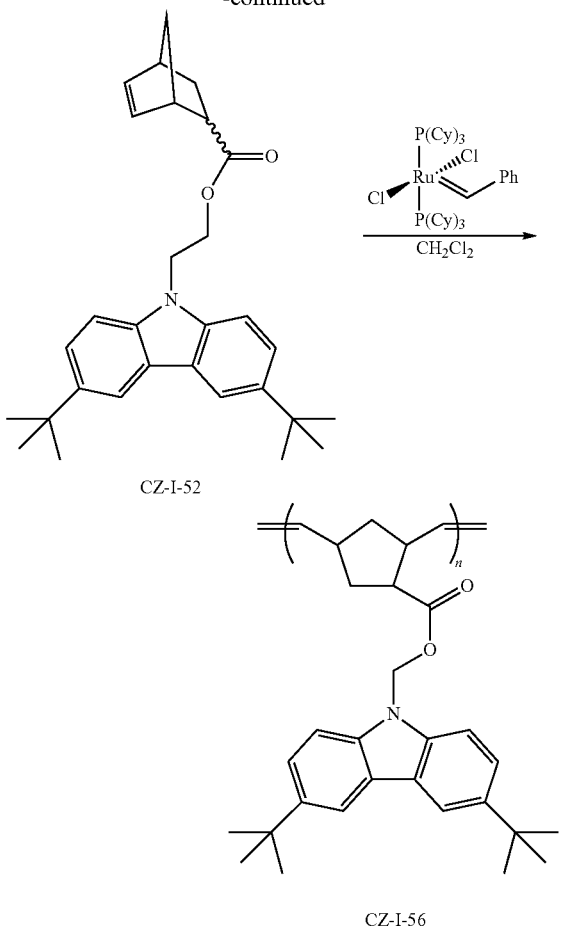

CZ-I-52

CZ-I-56

Step 1: (1S,4S)-2-(3,6-di-tert-butyl-9H-carbazol-9-yl)ethyl bicyclo[2.2.1]hept-5-ene-2-carboxylate (CZ-I-52)

YZ-I-69 (see preparative example 2) (1.462 g, 4.51 mmol), 5-norbornene-2-carboxylic acid (1.231 g, 8.91 mmol) and 10 mL of dry THF were combined in a round bottom flask (with stirring) and cooled in an ice bath for 20 minutes. DCC (1.398 g, 6.78 mmol) and DMAP (0.054 g, 0.44 mmol) were weighed (on weighing paper) and added to the reaction flask. The flask was subsequently removed from the ice bath and allowed to warm to room temperature. The reaction proceeded overnight for 18 hours. The reaction was checked by TLC. The reaction mixture was filtered to remove the insoluble DCC by-product and the filtrate was removed under vacuum to give a white precipitate. Methanol was used to isolate the precipitate by vacuum filtration. Column chromatography (silica gel, hexanes:ethyl acetate=9:1) was performed to purify the product. The purified product was isolated by vacuum filtration and dried overnight for 18 hours under vacuum to give a white powder (0.738 g, 36.9%).

$^1$H (300 MHz, CDCl$_3$): δ8.09 (d, 2H), 7.48-7.56 (m, 2H), 7.32-7.39 (m, 2H), 5.98-6.10 (m, 1H exo), 5.57-5.63 (m, 1H endo), 4.42-4.58 (m, 2H), 4.38 (m, 2H), 2.99 (s, 1H), 2.76-2.87 (m, 2H), 1.72-1.85 (m, 1H), 1.45 (s, 18H), 1.16-1.37 (m, 3H). $^{13}$C{$^1$H} (75 MHz, CDCl$_3$): δ 175.04, 142.24, 139.16, 137.96, 132.48, 123.64, 123.12, 116.53, 108.34, 62.34, 49.81, 45.74, 43.45, 42.69, 41.90, 34.91, 32.29, 32.28, 29.40

EI-MS (m/z): M$^+$ calcd for C$_{30}$H$_{37}$NO$_2$, 443.28. Found 443.3. Elemental Analysis Calculated for C$_{30}$H$_{37}$NO$_2$: C, 81.22; H, 8.41; N, 3.16. Found: C, 81.20; H, 8.50; N, 3.16.

Step 2: CZ-I-56

The CZ-I-52 monomer, prepared in step 1 above, (0.9002 g, 2.03 mmol) was weighed into a bottle. A Grubbs's first generation catalyst (0.0172 g, 2.1×10$^{-2}$ mmol) was weighed out into a separate vial. The bottle and vial were placed into a glove box. Then, 18 mL of dry CH$_2$Cl$_2$ was added to the bottle containing monomer CZ-I-11 with stirring and then capped. 1 mL of dry CH$_2$Cl$_2$ was added to a vial containing Grubbs's first generation catalyst and shaken vigorously. Subsequently, the Grubbs's catalyst solution was quickly transferred to the bottle with the monomer solution (while stirring) and then capped. An additional 1 mL of CH$_2$Cl$_2$ was added to the Grubbs's catalyst vial (for washing) and shaken. The Grubbs's solution was then transferred into the monomer bottle (while stirring) and then capped. The polymerization was allowed to proceed overnight for 16 hours. The reaction was quenched (outside of the glove box) with 5 mL of ethyl vinyl ether, rotovapped to concentrate the polymer solution, and then transferred (dropwise) into 75 mL of methanol to precipitate the polymer. The polymer was then vacuum filtered and re-dissolved in minimal (<3 mL) CH$_2$Cl$_2$ and 2 mL of ethyl vinyl ether was added. This solution was then added (dropwise) to 75 mL of methanol to precipitate the polymer. The process of isolating, dissolving, re-crystallizing (from methanol) and vacuum filtering the polymer was repeated 4 more times in order to remove the Grubbs's catalyst. The final product was dried under vacuum to give a cream colored powder (0.408 g, 45.3%).

$^1$H (300 MHz, CDCl$_3$): δ8.06 (s, 2H), 7.35-7.52 (br m, 2H), 7.26-7.35 (br m, 2H), 4.59-5.46 (br m, 2H), 3.91-4.57 (br m, 2H), 2.18-3.13 (br m, 3H), 1.69-2.03 (br m, 2H), 1.41 (s, 18H), 0.79-1.23 (br m, 2H). Elemental analysis calculated for C$_{30}$H$_{37}$NO$_2$: C, 81.22; H, 8.41; N, 3.16. Found: C, 80.44; H, 8.38; N, 3.19. Gel Permeation Chromatography (THF): M$_w$=46,000; M$_n$=21,000; PDI=2.138.

Preparative Example 11

Synthesis of Compound Poly[(1S,4S)-3,5-di(9H-carbazol-9-yl)benzyl bicyclo[2.2.1]hept-5-ene-2-carboxylate] (CZ-I-107)

Synthesis Scheme 7

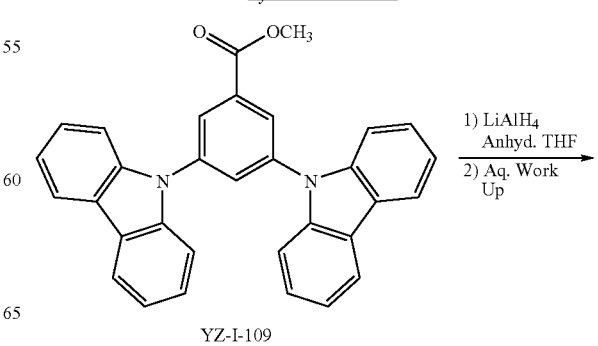

YZ-I-109

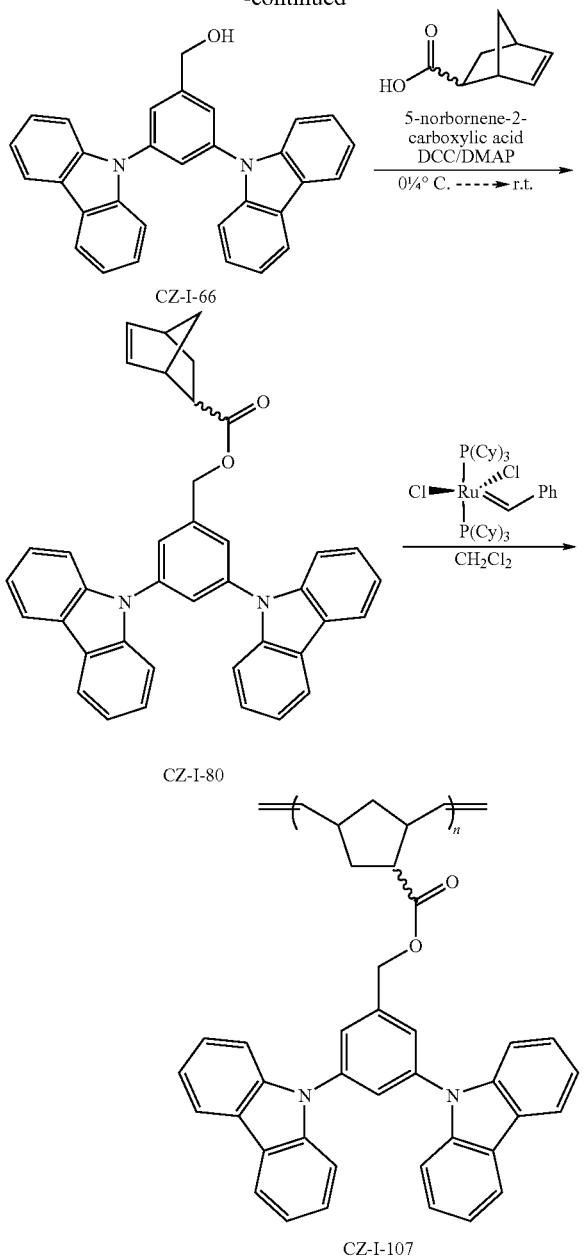

Step 1: (3,5-di(9H-carbazol-9-yl)phenyl)methanol (CZ-I-66)

Purified YZ-I-109 was synthesized according to preparative example 16 step 3. YZ-I-109 (1.002 g, 2.15 mmol) was added to a flask (under inert $N_2$ atmosphere) and ~30 mL of THF (anhydrous) was added to fully dissolve the starting material. LiAlH$_4$ (0.438 g, 11.54 mmol) was weighed out into a separate vial. Small amounts of LiAlH$_4$ were progressively added to the reaction flask. After complete addition of LiAlH$_4$, the reaction flask was refluxed overnight at 75° C. The reaction was checked by TLC for completion. The reaction was then quenched by very slow addition of deionized water (dropwise) to the flask until the reaction solution ceased bubbling. Following quenching the reaction mixture was vacuum filtered to remove insoluble Al(OH)$_3$. The filtrate was dried with a rotary evaporator (with heating) to obtain a white crystalline crude product. Column chromatography (silica gel, hexanes:ethyl acetate=7:3) performed to purify crude product. The product fractions were dried under vacuum to produce a clear oil that crystallized under high vacuum. The crystalline product was isolated by vacuum filtration using deionized water and dried under high vacuum to give a white powder (0.667 g, 71.0%).

$^1$H NMR showed residual solvent impurities. $^1$H (300 MHz, CDCl$_3$): δ8.16 (d, J=7.7 Hz, 4H), 7.50-7.58 (m, 3H), 7.45 (m, 4H), 7.32 (m, 4H), 4.96 (d, J=3.7 Hz, 2H), 1.97 (t, J=4.5 Hz, 1H).

Step 2: (1S,4S)-3,5-di(9H-carbazol-9-yl)benzyl bicyclo[2.2.1]hept-5-ene-2-carboxylate (CZ-I-80)

CZ-I-66 (0.551 g, 1.26 mmol), 5-norbornene-2-carboxylic acid (0.351 g, 2.54 mmol) and 10 mL of dry THF were combined in a round bottom flask (with stirring) and cooled in an ice bath for 20 min. DCC (0.399 g, 1.93 mmol) and DMAP (0.056 g, 0.46 mmol) were weighed (on weighing paper) and added to the reaction flask. The flask was subsequently removed from the ice bath and allowed to warm to room temperature. The reaction was allowed to proceed for ~5 h. The reaction was then checked by TLC. Reaction mixture was filtered to remove insoluble DCC by-product and filtrate was dried with a rotary evaporator to give viscous cloudy liquid. Methanol was added to precipitate the product. The white product was isolated by vacuum filtration and recrystallized from acetone using methanol:water (75:25). Following isolation (by vacuum filtration), the product was dried under high vacuum in oven (40° C.) for 16 hours to produce a white powder (0.502 g, 71.6%).

$^1$H (300 MHz, CDCl$_3$): δ8.15 (m, 4H), 7.78 (m, 1H), 7.68 (m, 2H), 7.54 (m, 4H), 7.45 (m, 4H), 7.32 (m, 4H), 6.08-6.18 (m, 1H exo), 5.90 (m, 1H endo), 5.26-5.38 (m, 2H), 3.23-3.30 (m, 1H), 3.03-3.14 (m, 1H), 2.89-2.98 (m, 1H), 1.91-2.04 (m, 1H), 1.35-1.53 (m, 2H), 1.23-1.33 (m, 1H). $^{13}$C{$^1$H} (75 MHz, CDCl$_3$): δ 174.76, 140.68, 140.54, 139.77, 138.40, 138.30, 132.50, 126.44, 124.87, 123.88, 120.72, 120.68, 109.90, 65.22, 49.93, 46.06, 43.67, 42.80, 29.64. EI-MS (m/z): M$^+$ calcd for $C_{39}H_{30}N_2O_2$, 558.23. Found 557.3. Elemental analysis calculated for $C_{39}H_{30}N_2O_2$: C, 83.85; H, 5.41; N, 5.01. Found: C, 83.59; H, 5.49; N, 5.11.

Step 3: Poly[(1S,4S)-3,5-di(9H-carbazol-9-yl)benzyl bicyclo[2.2.1]hept-5-ene-2-carboxylate] (CZ-I-107)

CZ-I-80 monomer (0.4003 g, 0.72 mmol) was weighed into a bottle. Grubbs's first generation catalyst (0.0065 g, 7.90×10$^{-3}$ mmol) was weighed out into separate vial. The bottle and vial were placed into a glovebox. 5 mL of dry CH$_2$Cl$_2$ was added to the bottle containing monomer CZ-I-80 with stirring and then capped. 1 mL of dry CH$_2$Cl$_2$ was added to vial containing Grubbs's first generation catalyst and shaken vigorously. Subsequently, the Grubbs's catalyst solution was quickly transferred to the bottle with monomer solution (while stirring) and then capped. An additional 1 mL of CH$_2$Cl$_2$ was added to the Grubbs's catalyst vial (for washing) and shaken. The Grubbs's solution was then transferred into the monomer bottle (while stirring) and then capped. The polymerization was allowed to proceed for 18 hours. The reaction was quenched (out of glovebox) with 2.5 mL of ethyl vinyl ether, processed with a rotary evaporator to concentrate the polymer solution, and then transferred (dropwise) into 30 mL of methanol to precipitate polymer. The polymer was then vacuum filtered and re-dissolved in minimal (<3 mL) CH$_2$Cl$_2$ and 2 mL of ethyl vinyl ether was added. This solution was then added (dropwise) to 30 mL of methanol to precipitate polymer. Process of isolating, dissolving, re-crystallizing (from methanol) and vacuum filtering polymer repeated 2 more times in order to remove Grubbs's catalyst. Final product was dried under vacuum (47° C.) for 16 hours to give a cream colored powder (0.240 g, 60.0%).

$^1$H (300 MHz, CDCl$_3$): δ7.90-8.17 (br m, 4H), 7.05-7.78 (br m, 15H), 4.73-5.46 (br m, 4H), 0.38-3.15 (br m, 9H). Elemental analysis calculated. for C$_{39}$H$_{30}$N$_2$O$_2$: C, 83.85; H, 5.41; N, 5.01. Found: C, 83.55; H, 5.42; N, 4.97. Gel Permeation Chromatography (THF): M$_w$=40,000; M$_n$=22,000; PDI=1.829.

Preparative Example 12

Synthesis of Compound Poly[(1S,4S)-(2,6-di(9H-carbazol-9-yl)pyridin-4-yl)methyl bicyclo[2.2.1]hept-5-ene-2-carboxylate] (CZ-I-114)

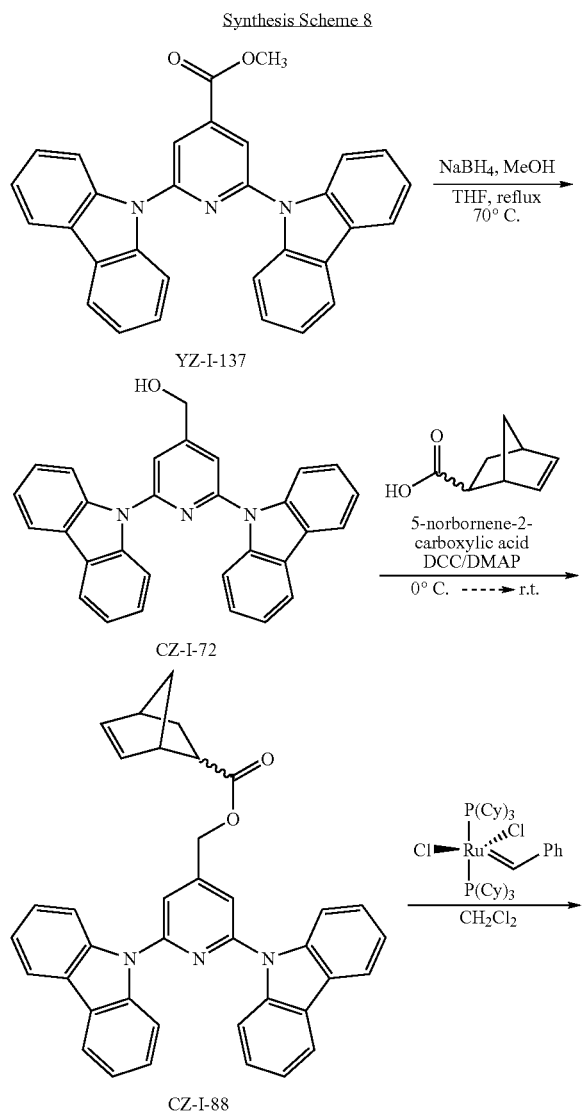

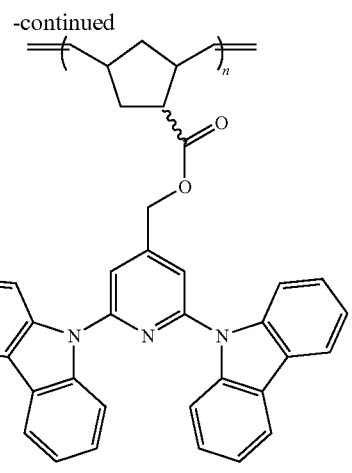

Step 1: CZ-I-72

Purified YZ-I-137 was synthesized according to preparative example 19. YZ-Cab-36 (1.002 g, 2.15 mmol) was added to a flask (under inert N$_2$ atmosphere) and ~50 mL of THF (anhydrous) was added to fully dissolve the starting material. NaBH$_4$ (0.485 g, 12.82 mmol) was weighed out into a separate vial. Small amounts of NaBH$_4$ were progressively added to the reaction flask. After complete addition of NaBH$_4$, the reaction flask was heated to 70° C. Methanol (8 mL) was added to flask (dropwise) over a 15 minute period. After 1 h the reaction was checked by TLC. If starting material was observed an additional 5 mL of methanol was added and reaction was allowed to continue. Following completion, saturated NH$_4$Cl (10 mL) was added to quench the reaction. The reaction solution was then vacuum filtered to remove insoluble precipitate(s) and Na$_2$SO$_4$ was subsequently added to the filtrate to dry the solution. The solution was proc processed with a rotary evaporator to dryness to produce a yellow crude product. Column chromatography (silica gel, toluene:ethyl acetate=8:2) performed to purify crude product due to acceptable solubility of yellow crude product in toluene. The product fractions produced a clear oil after rotovapping that crystallized upon standing. The purified product was dried under high vacuum and then isolated by vacuum filtration using deionized water. The isolated product was dried under high vacuum to produce a white powder (0.575 g, 61.0%). $^1$H NMR showed residual solvent impurities.

$^1$H (300 MHz, DMSO): δ8.25 (m, 2H), 7.93 (m, 3H), 7.76 (m, 4H), 7.42 (m, 4H), 7.32 (m, 4H), 5.77 (t, J=5.9 Hz, 1H), 4.89 (d, J=6.0 Hz, 2H).

Step 2: (1S,4S)-(2,6-di(9H-carbazol-9-yl)pyridin-4-yl)methyl bicyclo[2.2.1]hept-5-ene-2-carboxylate (CZ-I-88)

CZ-I-72 (0.402 g, 0.91 mmol), 5-norbornene-2-carboxylic acid (0.252 g, 1.82 mmol) and 10 mL of dry THF were combined in a round bottom flask (with stirring) and cooled in an ice bath for 20 min. DCC (0.297 g, 1.44 mmol) and DMAP (0.061 g, 0.50 mmol) were weighed (on weighing paper) and added to the reaction flask. The flask was subsequently removed from the ice bath and allowed to warm to room temperature. The reaction proceeded for 18 hours. The reaction was checked by TLC but reaction was stopped prior to full disappearance of starting material. Reaction mixture was filtered to remove insoluble DCC by-product and filtrate was dried with a rotary evaporator to give a cloudy white oil that crystallized upon standing. Due to solubility issues, the crude product was dissolved in a mixture of hot THF and toluene and adsorbed onto silica gel. Column chromatography (silica gel, hexanes:ethyl acetate=8:2) performed to purify product. Product fractions were dried with a rotary evaporator to produce a white crystalline solid that was isolated by vacuum filtration using methanol. The isolated product was dried in a vacuum oven (40° C.) for 16 hours to produce a white powder (0.402 g, 78.5%).

$^1$H (300 MHz, DMSO): δ8.26 (m, 4H), 7.94 (m, 4H), 7.77 (m, 2H), 7.43 (m, 4H), 7.33 (m, 4H), 6.03-6.21 (m, 1H exo), 5.88-5.95 (m, 1H endo), 5.35-5.54 (m, 2H), 3.07-3.26 (m, 2H), 2.80-2.96 (m, 1H), 1.88-2.01 (m, 1H), 1.24-1.52 (m, 3H). $^{13}$C{$^1$H} (75 MHz, DMSO): δ 175.11, 142.10, 138.29, 137.99, 132.59, 129.53, 126.20, 126.08, 126.06, 123.35, 123.33, 120.54, 120.52, 119.85, 110.34, 109.94, 64.55, 49.86, 45.96, 43.60, 42.77, 29.80, 29.76, 29.74, 29.48, 29.46, 29.44, 29.40, 28.91, 27.69, 26.19. EI-MS (m/z): M$^+$ calcd for $C_{38}H_{29}N_3O_2$, 559.23. Found 559.4. Elemental analysis calculated for $C_{38}H_{29}N_3O_2$: C, 81.55; H, 5.22; N, 7.51. Found: C, 81.40; H, 5.41; N, 7.44.

Step 3: CZ-I-114

CZ-I-88 monomer (0.3192 g, 0.57 mmol) was weighed into a bottle. Grubbs's first generation catalyst (0.0058 g, 7.04×10$^{-3}$ mmol) was weighed out into separate vial. The bottle and vial were placed into a glovebox. 4 mL of dry CH$_2$Cl$_2$ was added to the bottle containing monomer CZ-I-88 with stirring and then capped. 1 mL of dry CH$_2$Cl$_2$ was added to vial containing Grubbs's first generation catalyst and shaken vigorously. Subsequently, the Grubbs's catalyst solution was quickly transferred to the bottle with monomer solution (while stirring) and then capped. An additional 1 mL of CH$_2$Cl$_2$ was added to the Grubbs's catalyst vial (for washing) and shaken. The Grubbs's solution was then transferred into the monomer bottle (while stirring) and then capped. The polymerization was allowed to proceed for 18 hours. The reaction was quenched (out of glovebox) with 2.5 mL of ethyl vinyl ether, dried with a rotary evaporator to concentrate the polymer solution, and then transferred (dropwise) into 30 mL of methanol to precipitate polymer. The polymer was then vacuum filtered and re-dissolved in minimal (<3 mL) CH$_2$Cl$_2$ and 1 mL of ethyl vinyl ether was added. Solution precipitated requiring addition of dichloromethane to dissolve solution. This solution was then added (dropwise) to 30 mL of methanol to precipitate polymer. Process of isolating, dissolving, re-crystallizing (from methanol) and vacuum filtering polymer repeated 2 more times in order to remove Grubbs's catalyst. Final product was dried under vacuum (47° C.) for 16 hours to give a white colored powder (0.177 g, 55.3%).

$^1$H (300 MHz, CDCl$_3$): δ7.74-8.04 (br m, 6H), 7.09-7.37 (br m, 12H), 4.49-5.46 (br m, 4H), 0.39-3.17 (br m, 9H). Elemental analysis calculated. for $C_{38}H_{29}N_3O_2$: C, 81.55; H, 5.22; N, 7.51. Found: C, 81.28; H, 5.25; N, 7.39. Gel Permeation Chromatography (THF): $M_w$=27,000; $M_n$=16,000; PDI=1.689.

Preparative Example 13

Synthesis of Compound Poly[(1S,4S)-(9-(4'-(9H-carbazol-9-yl)biphenyl-4-yl)-9H-carbazol-3-yl)methyl bicyclo[2.2.1]hept-5-ene-2-carboxylate] (CZ-I-154)

Synthesis Scheme 9

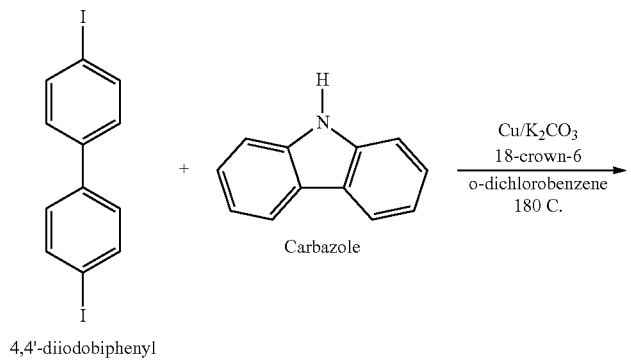

4,4'-diiodobiphenyl

Carbazole

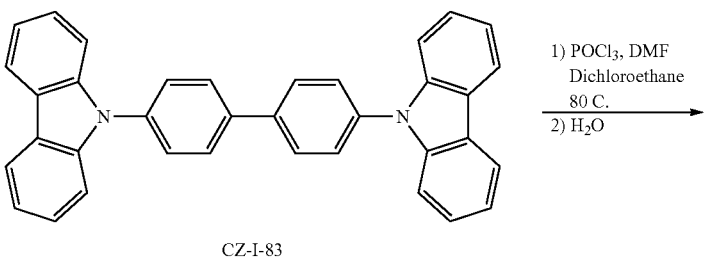

CZ-I-83

-continued
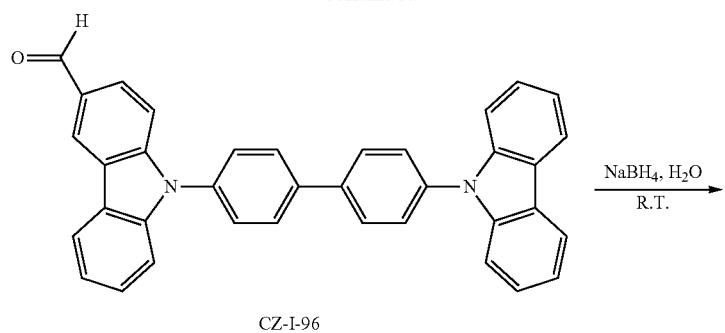
CZ-I-96
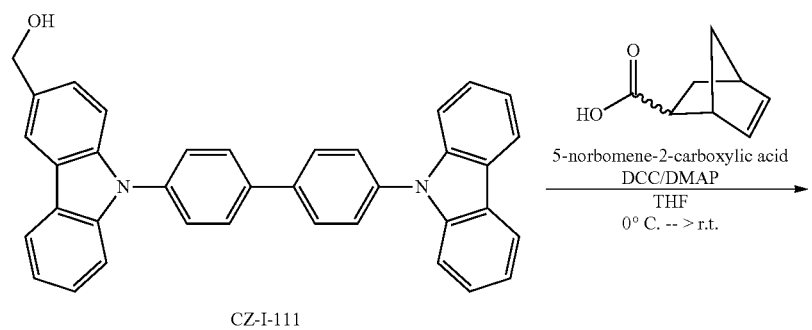
CZ-I-111
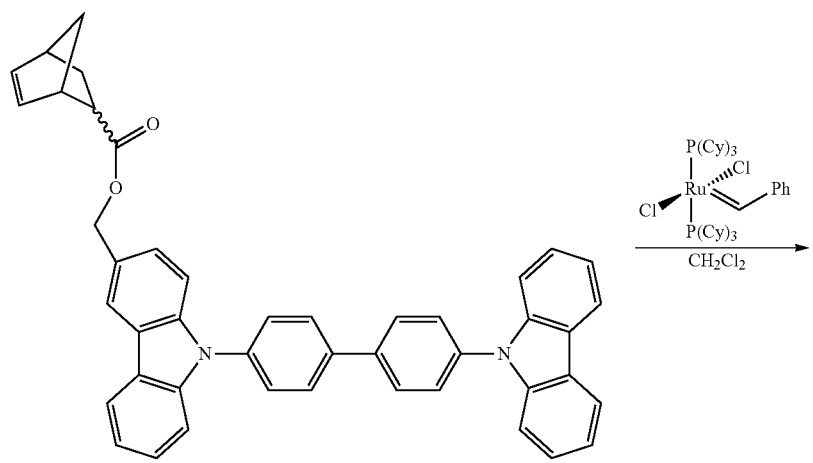
CZ-I-127
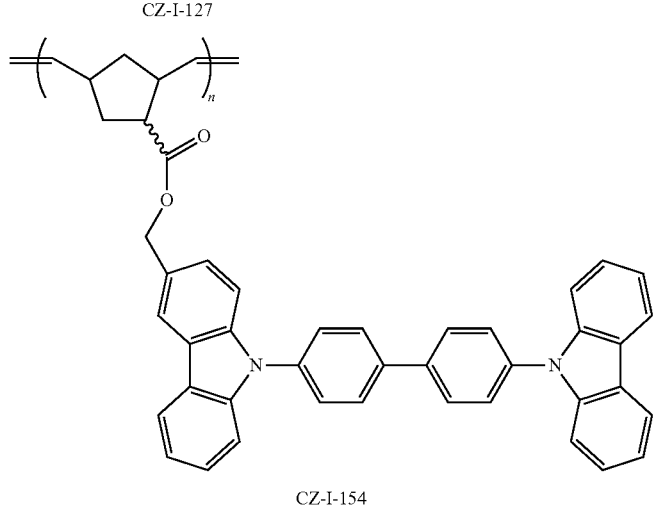
CZ-I-154

Step 1: 4,4'-di(9H-carbazol-9-yl)biphenyl (CZ-I-83)

4,4'-Diiodobiphenyl (10.001 g, 24.63 mmol), carbazole (9.078 g, 54.29 mmol), $K_2CO_3$ (20.087 g, 145.34 mmol), 18-crown-6 (0.100 g, 0.34 mmol), and copper powder (10.051 g, 158.16 mmol) were combined in reaction flask. To the flask, o-dichlorobenzene (50 mL) was added. The reaction was heated under inert N2 atmosphere at 180° C. overnight. TLC showed evidence of limited di-substitution product which necessitated the addition of $K_2CO_3$ (4.994 g, 36.13 mmol) and Cu powder (5.223 g, 82.19 mmol) to the reaction flask to promote di-substitution. The reaction was allowed to proceed overnight. Additional reagents had no noticeable effect on the reaction so the reaction was stopped. Insoluble material was removed by vacuum filtration and washed with several portions of THF. On standing, a crystalline product crashed out of the filtrate. Further crystallization was promoted by the addition of a large amount of methanol. The precipitate was vacuum filtered to isolate. TLC (hexanes: DCM=8:2) confirmed precipitate was product with minor impurity. Purification was accomplished by dissolving the precipitate in hot boiling THF followed by filtration to obtain a green insoluble impurity. The product began to precipitate on standing and cooling. The filtrate/product mixture was dried under vacuum until the product started crashing out of solution and methanol was added to promote full precipitation. The product was isolated by vacuum filtration and air dried (24 hours). A cream colored flaky product was obtained (7.660 g, 64.2%).

$^1$H (300 MHz, DMSO): δ8.27 (d, J=7.7 Hz, 4H), 8.04-8.16 (m, 4H), 7.74-7.83 (m, 4H), 7.33 (d, J=2.0 Hz, 1H), 7.31 (t, J=1.7 Hz, 2H), 7.29 (d, J=1.8 Hz 1H).

Step 2: 9-(4'-(9H-carbazol-9-yl)biphenyl-4-yl)-9H-carbazole-3-carbaldehyde (CZ-I-96)

A round bottom flask was set-up in an ice bath under nitrogen flow. DMF (7.2 mL, 93.39 mmol) was added to the flask while stirring. $POCl_3$ (8.5 mL, 92.86 mmol) was slowly added to the flask to give the white Vilsmeier-Haack reagent as a solid that was set aside on ice. CZ-I-83 (7.60 g, 15.68 mmol) was weighed into a separate flask set-up for reflux and under nitrogen flow. To this second flask dichloroethane (~180 mL) was added and the flask was heated (80° C.) to give a brownish-yellow solution. The Vilsmeier-Haack reagent was added to the second flask and the reaction was allowed to proceed under reflux. The reaction was monitored by TLC. A small sample of the mixture was removed and added to vial. Deionized water and Ethyl Acetate were added to the vial and shaken vigorously. The organic layer was spotted against starting material and eluted (toluene:dichloromethane=1:1). After several days the reaction still had a minor amount of starting material but was stopped. The reaction mixture was slowly added into a beaker half filled with ice to give a precipitate in a dark greenish liquid. Flask washed with ice water and subsequently dichloromethane to fully extract organic components and added to beaker. After melting, solution from the beaker was dried with a rotary evaporator to remove organic solvents (water remains). Vacuum filtration of solids was attempted but filtering was not possible due to filter clogging. Instead, the reaction mixture was extracted with dichloromethane (3×) using a separatory funnel and all fractions were combined. Organic solvents were then removed under high vacuum with heating until a small amount of solution was present. This solution was purified by column chromatography (silica gel, dichloromethane: toluene=3:2) but solubility issues resulted inadequate separation of starting material from monosubstituted product. A second column was required to purify the product. The isolated crude product from the first column was dissolved in hot dichloromethane and toluene and processed with a rotary evaporator to minimal solvents while heating to ensure good solubility. The product fractions were dried on a rotary evaporator. The product (mono-substituted) was isolated by vacuum filtration with deionized water for washing and air dried (24 hours) to give a yellow powder (2.078 g, 27.44%).

$^1$H (300 MHz, $CDCl_3$): δ10.15 (s, 1H), 8.71 (d, J=1.1 Hz, 1H), 8.12-8.29 (m, 3H), 7.86-8.05 (m, 5H), 7.72 (t, J=8.8 Hz, 4H), 7.11-7.60 (m, 11H). $^{13}C\{^1H\}$(75 MHz, $CDCl_3$): δ192.03, 144.69, 142.05, 141.00, 140.52, 139.20, 136.40, 129.29, 128.83, 127.78, 127.35, 124.18, 123.97, 123.76, 123.59, 121.61, 121.01, 120.66, 120.39, 110.72, 110.44, 110.04.

Step 3: (9-(4'-(9H-carbazol-9-yl)biphenyl-4-yl)-9H-carbazol-3-yl)methanol (CZ-I-111)

CZ-I-96 (2.071 g, 4.04 mmol) was added to a flask with a stir bar. The flask was placed under nitrogen flow and tetrahydrofuran (~175 mL) was added to dissolve CZ-I-96 resulting in a semi-opaque solution. $NaBH_4$ (0.903 g, 23.87 mmol) was weighed into a separate bottle and deionized water (~2 mL) was added to the same bottle. The $NaBH_4$ solution was added dropwise to the flask and an additional 1 mL of deionized water was used to wash the $NaBH_4$ bottle. The reaction was monitored by TLC (100% dichloromethane). After completion the reaction mixture was processed with a rotary evaporator to minimal solvents followed by addition of excess deionized water to yield a white precipitate. The precipitate was vacuum filtered and TLC of the precipitate showed a minor impurity (purification is not necessary). Precipitate was vacuum dried (47° C.) for 16 hours to give a white powder (1.914 g, 95.3%).

$^1$H (300 MHz, DMSO): 8.15-8.30 (m, 4H), 8.01-8.13 (m, 4H), 7.67-7.81 (m, 4H), 7.37-7.53 (m, 8H), 7.24-7.35 (m, 3H), 5.23 (t, J=5.6 Hz, 1H), 4.68 (d, J=5.6 Hz, 2H). $^{13}C\{^1H\}$ (75 MHz, DMSO): 140.95, 140.74, 13989, 139.03, 129.20, 129.17, 127.88, 127.04, 123.63, 123.55, 121.31, 120.90, 110.50, 110.46, 64.05.

Step 4: (1S,4S)-(9-(4'-(9H-carbazol-9-yl)biphenyl-4-yl)-9H-carbazol-3-yl)-methyl bicyclo 2.2.1 hept-5-ene-2-carboxylate (CZ 4-127)

CZ-I-111 (0.382 g, 0.74 mmol), 5-norbornene-2-carboxylic acid (0.395 g, 2.86 mmol) and 35 mL of dry THF were combined in a round bottom flask (with stirring). DCC (0.385 g, 1.87 mmol) and DMAP (0.114 g, 0.93 mmol) were weighed (on weighing paper) and added to the reaction flask slowly. The reaction proceeded overnight for 18 hours. The reaction was checked by TLC (Hexanes:Ethyl Acetate=8:2) until complete disappearance of starting material. Reaction mixture was filtered to remove insoluble DCC by-product and filtrate was dried on a rotary evaporator. Methanol was added to the flask to give a white precipitate that was isolated by vacuum filtration. Due to a minor impurity, the crude product required column chromatography (silica gel, hexanes:ethyl acetate=8:2) to be performed to purify product. Product fractions were dried under vacuum and then precipitated with methanol and then product was isolated by vacuum filtration. The isolated product was dried in a vacuum over (60° C.) for 16 hours to produce a white powder (0.324 g, 69.2%).

$^1$H (300 MHz, $CDCl_3$): δ8.18 (d, J=7.9 Hz, 4H), 7.93 (d, J=8.2 Hz, 4H), 7.66-7.76 (m, 4H), 7.39-7.56 (m, 8H), 7.27-

7.39 (m, 4H), 6.07-6.23 (m, 1H exo), 5.88-5.94 (m, 1H endo), 5.22-5.39 (m, 2H), 3.25 (s, 1H), 2.99-3.12 (m, 1H), 2.92 (s, 1H), 2.27-2.35 (m, 1H), 1.88-2.02 (m, 1H), 1.34-1.53 (m, 2H). $^{13}C\{^1H\}$ (75 MHz, $CDCl_3$): δ 174.85, 141.03, 140.87, 139.46, 138.34, 138.04, 137.53, 136.02, 132.61, 128.81, 128.77, 128.34, 127.74, 127.68, 127.12, 126.27, 123.73, 120.33, 110.06, 67.01, 49.89, 46.63, 46.09, 46.08, 43.70, 43.51, 42.84, 29.54. EI-MS (m/z): M+ calcd for $C_{45}H_{34}N_2O_2$, 634.7. Found 634.5. Elemental analysis calculated for $C_{45}H_{34}N_2O_2$: C, 85.15; H, 5.40; N, 4.41. Found: C, 84.93; H, 5.35; N, 4.40.

Step 5: (1S,4S)-(9-(4'-(9H-carbazol-9-yl)biphenyl-4-yl)-9H-carbazol-3-yl)methyl bicyclo 2.2.1 hept-5-ene-2-carboxylate (CZ-I-154)

CZ-I-127 monomer (0.407 g, 0.64 mmol) was weighed into a bottle. Grubbs's first generation catalyst (0.0058 g, 7.04×10⁻³ mmol) was weighed out into separate vial. The bottle and vial were placed into a glovebox. 5 mL of dry $CH_2Cl_2$ was added to the bottle containing monomer CZ-I-88 with stirring and then capped. 1 mL of dry $CH_2Cl_2$ was added to vial containing Grubbs's first generation catalyst and shaken vigorously. Subsequently, the Grubbs's catalyst solution was quickly transferred to the bottle with monomer solution (while stirring) and then capped. An additional 1 mL of $CH_2Cl_2$ was added to the Grubbs's catalyst vial (for washing) and shaken. The Grubbs's solution was then transferred into the monomer bottle (while stirring) and then capped. The polymerization was allowed to proceed overnight for 18 hours. The reaction was quenched (out of glovebox) with 3 mL of ethyl vinyl ether, processed with a rotary evaporator to concentrate the polymer solution, and then transferred (dropwise) into 30 mL of methanol to precipitate polymer. The polymer was then vacuum filtered and re-dissolved in minimal (<3 mL) $CH_2Cl_2$ and 1 mL of ethyl vinyl ether was added. Solution precipitated requiring addition of dichloromethane to dissolve solution. This solution was then added (dropwise) to 30 mL of methanol to precipitate polymer. Process of isolating, dissolving, re-crystallizing (from methanol) and vacuum filtering polymer repeated 2 more times in order to remove Grubbs's catalyst. Final product was dried under vacuum (47° C.) for 16 hours to give a white colored powder (0.179 g, 44.8%).

$^1H$ (300 MHz, $CDCl_3$): δ7.94-8.23 (br m, 4H), 7.09-7.88 (br m, 20H), 4.94-5.46 (br m, 4H), 1.02-3.07 (br m, 9H). Elemental analysis calculated for $C_{45}H_{34}N_2O_2$: C, 85.15; H, 5.40; N, 4.41. Found: C, 84.62; H, 5.38; N, 4.53. Gel Permeation Chromatography (THF): $M_w$=39,000; $M_n$=24,000; PDI=1.632.

Preparative Example 14

Synthesis of Poly(5-(Bicyclo[2,21]hept-5-en-2-yl) pentyl 3,5-di(carbazol-9-yl)benzoate) (YZ-I-133)

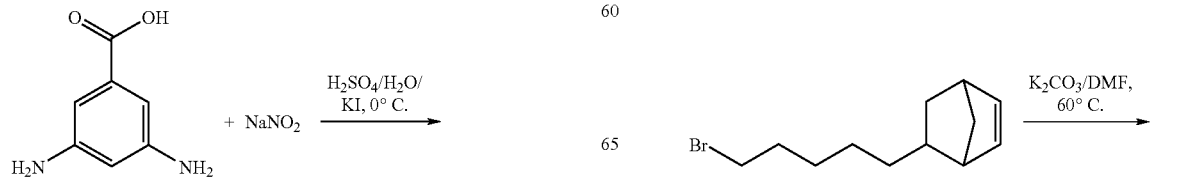

-continued

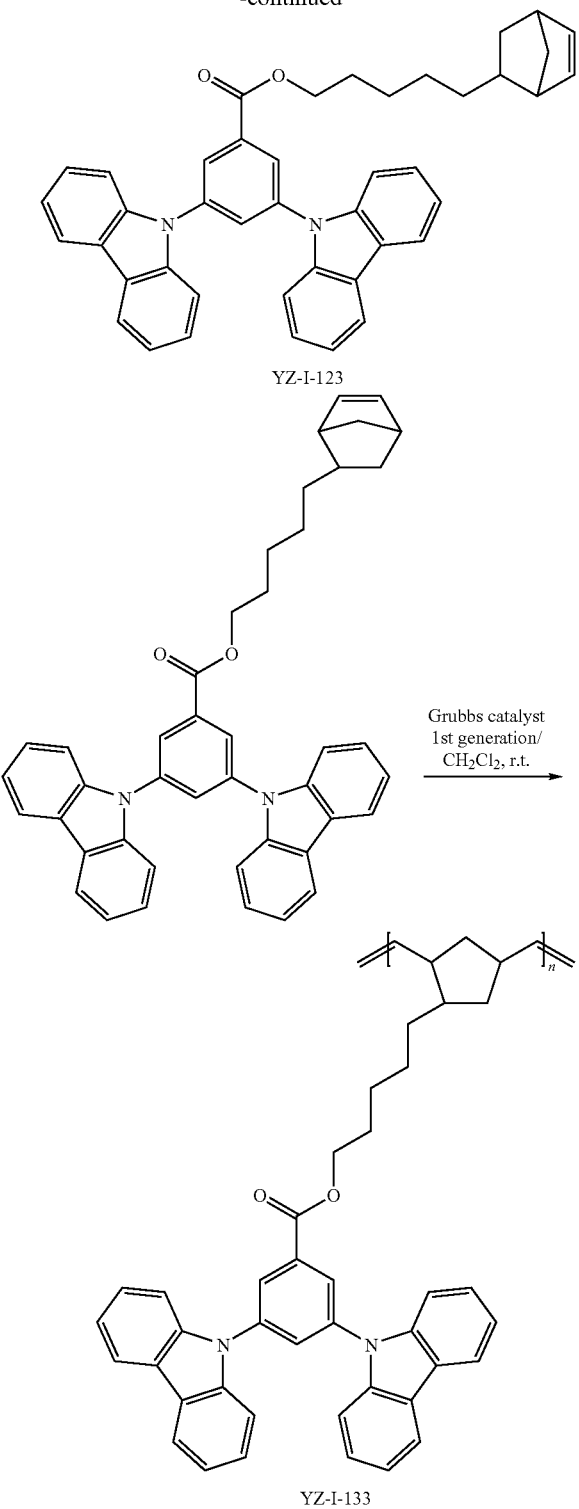

YZ-I-123

YZ-I-133

Grubbs catalyst 1st generation/ CH₂Cl₂, r.t.

Step 1: 3,5-Diiodobenzoic acid (YZ-I-89)

To an ice-cooled stirred suspension of 3,5-diaminobenzoic acid (6.0 g, 39.5 mmol) in concentrated sulfuric acid (60.0 ml) mixed with water (30.0 ml), sodium nitrite (6.5 g, 94.00 mmol) was slowly added. The color of the originally red suspension changed to orange. After 2 hours, urea (6.0 g, 100.00 mmol) was added, and then the solution was added slowly to an ice cooled solution of potassium iodide (40.0 g) in water (40.0 ml). After 3 hours at room temperature, water (300.0 ml) was added, and a black-brown solid was collected by filtration. This solid was dissolved in ethyl acetate, and the solution was washed with aqueous $NaS_2O_3$ until the $I_2$ had disappeared. Ethyl acetate was removed to give a brown solid in the amount of 7.1 g. This product was used for the next step without any further purification.

Step 2: Methyl 3,5-diiodobenzoate (YZ-I-93)

To a solution of 3,5-diiodobenzoic acid (6.8 g, 18.18 mmol) in methanol (200.0 ml) was added $CH_3SO_3H$ (0.5 ml). The reaction mixture was heated to reflux. After refluxing for 7.5 hours, most of the methanol was removed. Then, water (200.0 ml) was added and a dark-brown solid was collected by filtration. The product was purified by silica gel column chromatography using hexanes/ethyl acetate (8:2) as eluent. The final pure white product was obtained in the amount of 4.2 g (59.2%) by recrystallization from methanol/water:
$^1$H NMR (CDCl₃): δ 8.29 (d, 2H$_{Bz}$, J=1.6 Hz), 8.20 (t, 1H$_{Bz}$, J=1.6 Hz), 3.90 (s, 3H, OCH₃). $^{13}$C NMR (CDCl₃): δ 163.97, 148.99, 137.56, 133.08, 94.32, 52.73.

Step 3: Methyl 3,5-di(carbazol-9-yl)benzoate (YZ-I-109)

To a solution of methyl 3,5-diiodobenzoate (3.0 g, 7.73 mmol), carbazole (3.0 g, 17.94 mmol), Cu (6.4 g, 100.71 mmol) and 18-crown-6 (65 mg, 0.25 mmol) in 1,2-dichlorobenzene (30.0 ml) was added potassium carbonate (12.6 g, 91.17 mmol) under nitrogen and stirring. The reaction was carried out at 180° C. for 10.5 hours. After cooling, the reaction mixture was filtrated. Then, the solid residues were carefully washed with THF. The THF and 1,2-dichlorobenzene were evaporated from the combined filtration solution. The product was purified by silica gel column chromatography using toluene as eluent. The final pure white product was obtained in 2.6 g (71.7%) by recrystallization from acetone/methanol.
$^1$H NMR (CDCl₃): δ 8.37 (d, 1H$_{Bz}$, J=1.6 Hz), 8.15 (dd, 4H$_{Cz}$, J₁=7.2 Hz, J₂=0.8 Hz), 8.02 (t, 1H$_{Bz}$, J=1.6 Hz), 7.52 (dd, 4H$_{Cz}$, J₁=7.2 Hz, J₂=0.8 Hz), 7.45 (td, 4H$_{Cz}$, J₁=7.2 Hz, J₂=1.6 Hz), 7.32 (td, 4H$_{Cz}$, J₁=7.2 Hz, J₂=1.2 Hz), 3.99 (s, 3H, OCH₃). $^{13}$C NMR (CDCl₃): δ 165.39, 140.18, 139.54, 133.63, 129.09, 126.45, 126.20, 123.62, 120.55, 120.43, 109.42, 52.82. MS (EI) m/z (%): 466.0 (100%) [M⁺]. Anal. Calcd for $C_{32}H_{22}N_2O_2$: C, 82.38; H, 4.75; N, 6.00. Found: C, 82.34; H, 4.66; N, 6.03.

Step 4: 3,5-Di(carbazol-9-yl)benzoic acid (YZ-I-119)

To a solution of methyl 3,5-di(carbazol-9-yl)benzoate (1.0 g, 2.14 mmol) in THF/methanol (25.0 ml, 15:10) was added KOH (0.6 g, 10.69 mmol) in water (2.0 ml) at room temperature under stirring. The reaction was carried out at room temperature for 4.5 hours. The THF was evaporated. Next, methanol (20.0 ml) was added and then HCl water solution (80.0 ml; 15.0 ml of 36-38% HCl in 65.0 ml of water) was added. The mixture was stirred for 1 hour and a pale yellow solid product was obtained by filtration. The product was purified by recrystallization from acetone/water: 0.95 g (97.9%).
$^1$H NMR (CDCl₃): δ 8.37 (d, 2H$_{Bz}$, J=2.4 Hz), 8.21 (dt, 4H$_{Cz}$, J₁=7.2 Hz, J₂=0.8 Hz), 8.19 (t, 1H$_{Bz}$, J=2.4 Hz), 7.63

(dd, 4H$_{Cz}$, J$_1$=7.2 Hz, J$_2$=0.8 Hz), 7.47 (td, 4H$_{Cz}$, J$_1$=7.2 Hz, J$_2$=1.2 Hz), 7.30 (td, 4H$_{Cz}$, J$_1$=7.2 Hz, J$_2$=1.2 Hz). $^{13}$C NMR (CDCl$_3$): δ 166.04, 141.19, 140.34, 135.14, 130.08, 127.31, 127.11, 124.38, 121.32, 121.17, 110.42. MS (EI) m/z (%): 452.1 (100%) [M$^+$].

Step 5: 5-(Bicyclo[2,21]hept-5-en-2-yl)pentyl 3,5-di (carbazol-9-yl)benzoate (YZ-I-123)

To a solution of 3,5-di(carbazol-9-yl)benzoic acid (0.5 g, 1.10 mmol) and 5-(5-bromopentyl)bicycle[2,2,1]hept-2-ene (0.32 g, 1.32 mmol) in DMF (6.0 ml) was added K$_2$CO$_3$ (4.0 g, 28.94 mmol) at room temperature under stirring. The reaction was carried out at room temperature for 26.5 hours. Then water (50.0 ml) was added, and a white solid product was obtained by filtration. The product was purified by silica gel column chromatography using toluene/hexanes (6:4) as eluent. After the removal of solvents, a glass-like solid was dissolved in acetone (3.0 ml). The acetone solution was dropped into methanol/water (20.0 ml, 75:25) to give a white powder solid. After filtration and drying of the product, a white solid in the amount of 0.64 g (94.3%) was obtained.

$^1$H NMR (CDCl$_3$): δ 8.37 (d, 2H$_{Bz}$, J=1.6 Hz), 8.16 (dd, 4H$_{Cz}$, J1=7.2 Hz, J2=1.2 Hz), 8.02 (t, 1H$_{Bz}$, J=1.6 Hz), 7.53 (dd, 4H$_{Cz}$, J1=7.2 Hz, J2=1.2 Hz), 7.46 (td, 4H$_{Cz}$, J1=7.2 Hz, J2=1.2 Hz), 7.33 (td, 4H$_{Cz}$, J1=7.2 Hz, J2=1.2 Hz), 6.03 (dd, 1H, C=C—H, J1=5.6 Hz, J2=3.2 Hz, EX), 5.96 (dd, 1H, C=C—H, J1=5.6 Hz, J2=2.8 Hz, EX), 4.40 (t, 2H, OCH$_2$, J=7.2 Hz), 2.73 (s, br, 1H), 2.46 (m, 1H), 1.78 (m, 2H), 1.44-1.21 (m, 10H), 1.04 (m, 1H). $^{13}$C NMR (CDCl$_3$): δ 164.95, 140.19, 139.49, 136.67, 136.01, 134.03, 129.03, 126.43, 126.20, 123.61, 120.54, 120.43, 109.42, 65.99, 46.37, 45.25, 41.90, 38, 72, 36.50, 33.10, 28.78, 28.57, 26.37. MS (EI) m/z (%): 614.2 (100%) [M$^+$]. Anal. Calcd for C$_{43}$H$_{38}$N$_2$O$_2$: C, 84.01; H, 6.23; N, 4.56. Found: C, 84.03; H, 6.17; N, 4.45.

Step 6: Poly(5-(Bicyclo[2,21]hept-5-en-2-yl)pentyl 3,5-di(carbazol-9-yl)benzoate) (YZ-I-133)

To a solution of 5-(bicyclo[2,2,1]hept-5-en-2-yl)pentyl 3,5-di(carbazol-9-yl)-benzoate (0.5 g, 0.813 mmol) in dichloromethane (6.0 ml) was added Grubbs catalyst 1$^{st}$ generation (6.67 mg, 0.00813 mmol) in dichloromethane (2.0 ml) at room temperature under stirring in a glove box. The polymerization was carried out at room temperature for 15 hours. Ethyl vinyl ether (2.0 ml) was then added. After stirring for 55 minutes, the polymer and dichloromethane solution was dropped into methanol (60.0 ml) to give a white polymer solid. After which, the white solid product was collected by filtration. The reprecipitation procedure in dichloromethane/methanol was then repeated five times. After filtration and drying in a vacuum, the final product, a white solid in the amount of 0.41 g (82.0%), was obtained.

$^1$H NMR (CDCl$_3$): δ 8.31 (s, br, 2H$_{Bz}$), 8.06 (s, br, 4H$_{Cz}$), 7.93 (s, br, 1H$_{Bz}$), 7.45 (s, br, 4H$_{Cz}$), 7.37 (s, br, 4H$_{Cz}$), 7.25 (s, br, 4H$_{Cz}$), 5.19 (s, br, 1H, C=C—H), 5.08 (s, br, 1H, C=C—H), 4.28 (s, br, 2H, OCH$_2$), 2.30 (m, br, 1H), 1.72 (s, br, 4H), 1.30 (s, br, 8H), 0.88 (s, br, 2H). Anal. Calcd for C$_{43}$H$_{38}$N$_2$O$_2$: C, 84.01; H, 6.23; N, 4.56. Found: C, 83.72; H, 6.17; N, 4.53. GPC (THF): M$_w$=49000, M$_n$=13600, PDI=3.58.

Preparative Example 15

Synthesis of Compound YZ-I-135: Poly(bicyclo[2,2,1]hept-5-en-2-ylmethyl 3,5-di(carbazol-9-yl)benzoate)

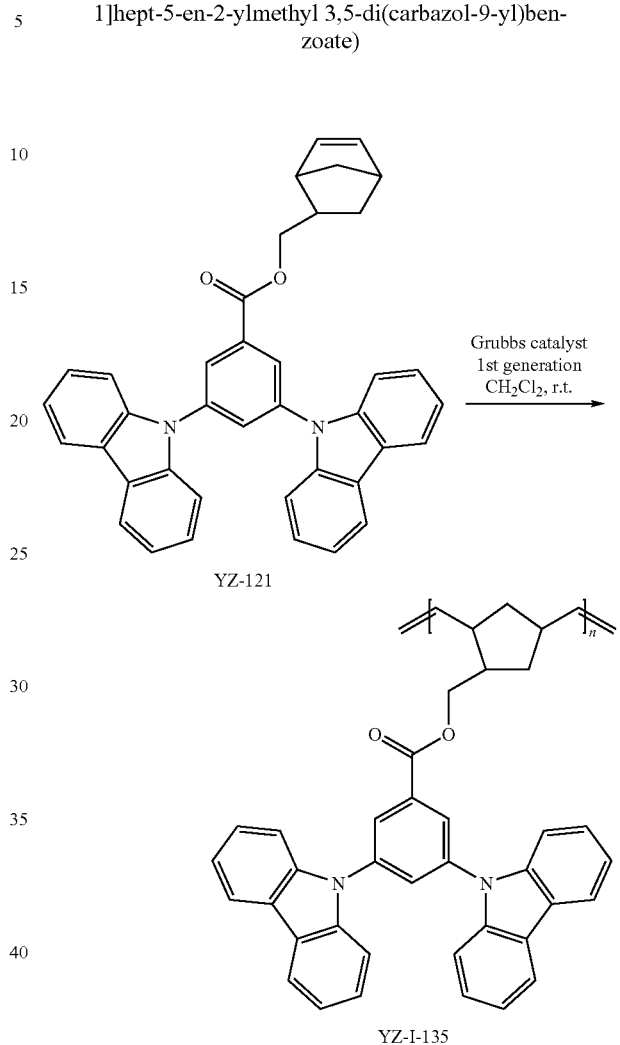

YZ-121

Grubbs catalyst
1st generation
CH$_2$Cl$_2$, r.t.

YZ-I-135

Step 1: Bicyclo[2,2,1]hept-5-en-2-ylmethyl 3,5-di (carbazol-9-yl)benzoate (YZ-I-121)

In the same method employed in steps 1-4 above in synthesis scheme 7, YZ-I-121 was prepared. To a solution of 3,5-di(carbazol-9-yl)benzoic acid (0.5 g, 1.1 mmol) and 5-(bromomethyl)bicycle[2,2,1]hept-2-ene (0.3 g, 1.6 mmol) in DMF (6.0 ml) was added K$_2$CO$_3$ (4.0 g, 28.94 mmol) at room temperature under stirring. The reaction was carried out at 60° C. for 26 hours. After cooling to room temperature, water (40.0 ml) was added. A white solid product was obtained by filtration. The product was purified by silica gel column chromatography using toluene/hexanes (6:4) as an eluent. After removal of the solvents, a glass-like solid was dissolved in acetone (2.0 ml). The acetone solution was dropped into methanol/water (20.0 ml, 8:2) to give a white powder solid. After filtration and drying, the product as white solid in 0.48 g (77.8%) was obtained.

$^1$H NMR (CDCl$_3$): δ 8.38 (m, 2H$_{Bz}$, EX:EN), 8.16 (d, 4H$_{Cz}$, J=7.2 Hz), 8.19 (m, 1H$_{Bz}$, EX:EN), 7.53 (d, 4H$_{Cz}$, J=7.2

Hz), 7.46 (t, 4H$_{Cz}$, J=7.2 Hz), 7.33 (t, 4 H$_{Cz}$, J=7.2 Hz), 6.19 (dd, 0.63H, C=C—H, J1=5.6 Hz, J2=2.4 Hz, EX), 6.09 (m, 0.66H, 2×C=C—H, EN), 6.00 (dd, 0.63H, C=C—H, J1=5.6 Hz, J2=1.4 Hz, EX), 4.49 (dd, 0.35H, OCH2, J1=10.4 Hz, J2=6.8 Hz, EN), 4.33 (dd, 0.35H, OCH2, J1=9.2 Hz, J2=9.2 Hz, EN), 4.18 (dd, 0.71H, OCH2, J1=10.4 Hz, J2=6.8 Hz, EX), 4.00 (dd, 0.71H, OCH2, J1=10.8 Hz, J2=9.2 Hz, EX), 2.87 (m, 2H), 2.53 (m, 1H), 1.88 (m, 1H), 1.45 (m, 2H), 0.67 (m, 1H). $^{13}$C NMR (CDCl$_3$): δ 164.77, 140.19, 139.50, 137.69, 136.85, 135.99, 134.06, 131.95, 129.00, 126.43, 126.20, 123.61, 120.54, 120.44, 109.42, 69.85, 69.21, 49.49, 45.08, 44.04, 43.76, 42.27, 41.68, 38.11, 37.90, 29.70, 29.07. MS (EI) m/z (%): 558.2 (100%) [M$^+$]. Anal. Calcd for C$_{39}$H$_{30}$N$_2$O$_2$: C, 83.85; H, 5.41; N, 5.01. Found: C, 83.89; H, 5.35; N, 4.98.

Step 2: Poly(bicyclo[2,2,1]hept-5-en-2-ylmethyl 3,5-di(carbazol-9-yl)benzoate) (YZ-I-135)

To a solution of bicyclo[2,2,1]hept-5-en-2-ylmethyl 3,5-di (carbazol-9-yl)benzoate (0.4 g, 0.716 mmol) in dichloromethane (5.0 ml) was added a 1st generation Grubbs catalyst (4.00 mg, 0.00716 mmol) in dichloromethane (2.0 ml) at room temperature under stirring in a glove box. The polymerization was carried out at room temperature for 15 hours. Ethyl vinyl ether (2.0 ml) was then added. After stirring for 30 minutes, the polymer dichloromethane solution was added to methanol (50 ml) to give a white polymer solid. The white solid product was collected by filtration. The reprecipitation procedure in dichloromethane/methanol was then repeated five times. After filtration and drying in a vacuum, the final product as white solid in 0.34 g (85.0%) was obtained.

$^1$H NMR (CDCl$_3$): δ 8.24 (s, br, 2H$_{Bz}$), 8.01 (s, br, 4H$_{Cz}$), 7.89 (s, br, 1H$_{Bz}$), 7.42 (s, br, 4H$_{Cz}$), 7.31 (s, br, 4H$_{Cz}$), 7.20 (s, br, 4H$_{Cz}$), 5.11 (s, br, 2H, C=C—H), 4.06 (s, br, 2H, OCH$_2$), 2.17-1.01 (m, 7H). Elemental Analysis Calculated for C$_{39}$H$_{30}$N$_2$O$_2$: C, 83.85; H, 5.41; N, 5.01. Found: C, 83.62; H, 5.35; N, 4.94. GPC (THF): M$_w$=47000, M$_n$=17000, PDI=2.78.

Preparative Example 16

Synthesis of Compound YZ-I-131: Methyl 2,6-dibromoisonicotinate

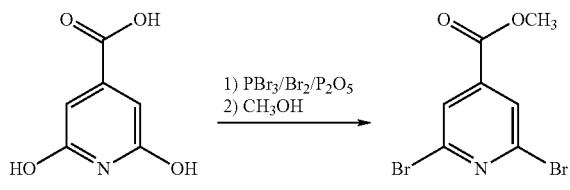

YZ-I-131

Synthesis of Methyl 2,6-dibromoisonicotinate (YZ-I-131)

The compound PBr$_3$ (21.8 ml, 0.232 mol) was loaded into a 250 ml three-neck flask cooled in a room temperature water bath under a flow of nitrogen. Br$_2$ (11.9 ml, 0.231 mol) was then added dropwise with stirring to PBr$_3$ to yield a yellow solid (PBr$_5$). 30 minutes was taken for addition of Br$_2$. P$_2$O$_5$ (12.0 g, 0.083 mol) was then added and the solid mixture was mixed well with a spatula under a flow of nitrogen. A reflux condenser was added via a connection to a water-filled bubbler, to trap evolved HBr. The mixture was heated to 98° C. for 2 hours and then cooled to room temperature. Citrazinic acid (20.0 g, 0.128 mol) was then added and the solid was mixed thoroughly with a spatula under a flow of nitrogen. The mixture was heated at 185° C. for 8 hours. The mixture was cooled back to room temperature. Methanol (150 ml) was slowly added (the reaction with methanol was exothermic, causing the solution to reflux). After the addition of methanol, the mixture was stirred until room temperature. Solid NaHCO$_3$ was added slowly until bubbling stopped. After which, water (300 ml) was added and then additional NaHCO$_3$ was added until the bubbling stopped. A brown solid product was collected with filtration. The solid was washed with water and dried at room temperature under air. The product was purified by silica gel column using hexanes/ethyl acetate (9:1) as a solvent. The final pure white product was obtained by recrystallization from methanol/water: 19.02 g (50.0%).

$^1$H NMR (CDCl$_3$): δ 8.00 (s, 2H), 3.97 (s, 3H). $^{13}$C NMR (CDCl$_3$): δ 162.74, 141.35, 141.25, 126.56, 53.38. MS (EI) m/z (%): 294.8 (100%) [M$^+$].

Preparative Example 17

Synthesis of Compound YZ-I-137: Methyl 2,6-di(carbazol-9-yl)isonicotinate

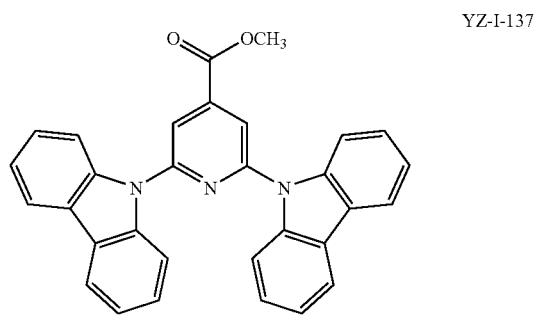 [SMILES: COC(=O)c1cc(-n2c3ccccc3c3ccccc32)nc(-n2c3ccccc3c3ccccc32)c1]

Synthesis of Methyl 2,6-di(carbazol-9-yl)isonicotinate (YZ-I-137)

To a solution of methyl 2,6-dibromo-isonicotinate (5.0 g, 16.95 mmol) (YZ_I-131), carbazole (6.0 g, 35.88 mmol) Cu (15.0 g, 236.04 mmol) and 18-crown-6 (0.1 g, 0.38 mmol) in 1,2-dichlorobenzene (50.0 ml) was added potassium carbonate (20.0 g, 144.71 mmol) under nitrogen and stirring. The reaction was carried out at 180° C. for 9 hours. After cooling, the reaction mixture was filtrated. Then, the solid residues were carefully washed with dichloromethane. Dichloromethane and 1,2-dichlorobenzene were evaporated from the combined filtration solution. After which, methanol (100 ml) was added to a dark brown solid. After stirring for 30 minutes, a yellow solid product was collected by filtration. The pure product was obtained in the amount of 6.4 g (81.4%) by recrystallization from acetone/methanol.

$^1$H NMR (CDCl$_3$): δ 8.17 (s, 2 Hp), 8.13 (dd, 4H$_{Cz}$, J=7.2 Hz), 8.06 (dd, 4 H$_{Cz}$, J=7.2 Hz), 7.42 (td, 4H$_{Cz}$, J$_1$=7.2 Hz, J$_2$=1.2 Hz), 7.35 (td, 4H$_{Cz}$, J$_1$=7.2 Hz, J$_2$=1.2 Hz), 4.04 (s, 3H, OCH$_3$). $^{13}$C NMR (CDCl$_3$): δ 164.67, 152.06, 141.89, 139.06, 126.44, 124.66, 121.55, 120.07, 113.47, 111.99, 53.24. MS (EI) m/z (%): 467.2 (100%) [M$^+$].

Preparative Example 18

Synthesis of Compound YZ-I-139: Methyl 2,6-bis(3,6-tert-butylcarbazol-9-yl)isonicotinate

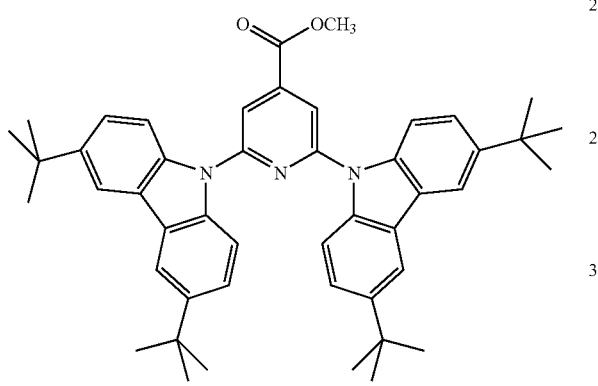

Synthesis of Methyl 2,6-bis(3,6-tert-butylcarbazol-9-yl)isonicotinate (YZ-I-139)

To a solution of methyl 2,6-dibromo-isonicotinate (2.0 g, 6.78 mmol) (YZ_I-131), 3,6-di-tert-butylcarbazole (4.0 g, 14.32 mmol), Cu (6.0 g, 94.42 mmol) and 18-crown-6 (0.05 g, 0.19 mmol) in 1,2-dichlorobenzene (30.0 ml) was added potassium carbonate (8.0 g, 57.88 mmol) under nitrogen and stirring. The reaction was carried out at 180° C. for 8 hours. After cooling, the reaction mixture was filtrated. Then, the solid residues were carefully washed with dichloromethane. Dichloromethane and 1,2-dichlorobenzene were evaporated from the combined filtration solution. Methanol (100.0 ml) was added to the dark brown solid. After stirring for 30 minutes, a yellow solid product was collected by filtration. The product was purified by silica gel column chromatography using toluene/hexanes (6:4) as an eluent. A pure product as a yellow solid in the amount of 3.5 g (74.4%) was obtained by recrystallization from acetone/methanol.

$^1$H NMR (CDCl$_3$): δ 8.12 (d, 4H$_{Cz}$, J=1.2 Hz) 8.10 (s, 2 Hp), 8.00 (dd, 4H$_{Cz}$, J$_1$=8.8 Hz, J$_2$=0.8 Hz), 7.45 (dd, 4H$_{Cz}$, J$_1$=8.8 Hz, J$_2$=1.2 Hz), 4.03 (s, 3H, OCH$_3$), 1.46 (s, 36H, 12×CH$_3$). $^{13}$C NMR (CDCl$_3$): δ 164.95, 152.29, 144.43, 141.55, 137.48, 124.72, 124.04, 116.00, 112.20, 111.75, 53.11, 34.87, 32.00. MS (EI) m/z (%): 691.4 (100%) [M$^+$].

Preparative Example 19

Synthesis of Compound YZ-I-141: (2,6-Dibromopyridin-4-yl)methanol

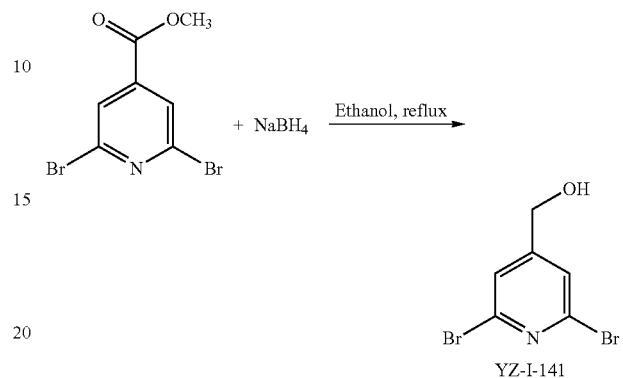

Synthesis of (2,6-Dibromopyridin-4-yl)methanol (YZ-I-141)

To a solution of methyl 2,6-dibromoisonicotinate (10.0 g, 33.91 mmol) in ethanol (200.0 ml) was slowly added NaBH$_4$ (6.4 g, 169.18 mmol) at room temperature under stirring. The reaction was heated to reflux and kept at reflux for 2 hours. The reaction solution was cooled to room temperature, and 2 M HCl (35.0 ml) was added slowly with stirring until the bubbling stopped. The ethanol was removed by rotary evaporation. Solid NaOH was added under stirring until the solution became basic. The solution continued to be stirred, and during stirring the product was precipitated. A white solid product was collected by filtration. After drying, the product was obtained in an amount of 5.0 g (55.6%).

$^1$H NMR (CDCl$_3$): δ 7.44 (s, 2H, Hp), 4.70 (s, 2H, OCH$_2$). $^{13}$C NMR (CDCl$_3$): δ 155.05, 140.70, 124.15, 62.22. MS (EI) m/z (%): 266.8 (100%) [M$^+$].

Preparative Example 20

Synthesis of YZ-I-145: (2,6-bis(3,6-di-tert-butylcarbazol-9-yl)pyridine-4-yl)methanol

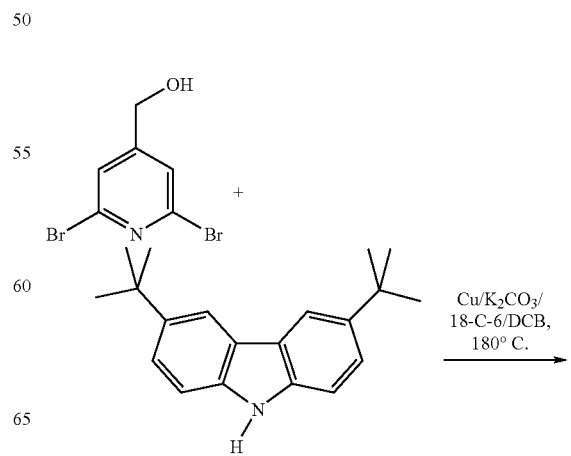

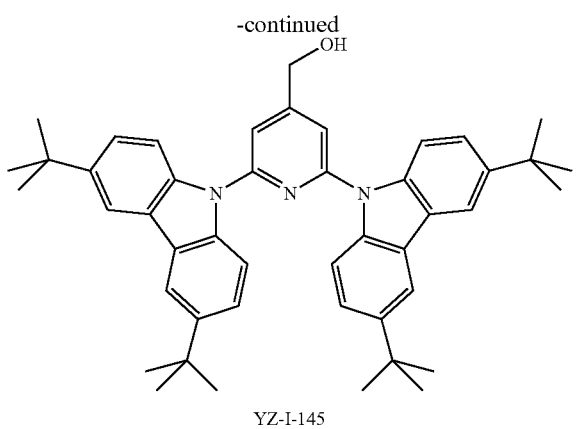

YZ-I-145

Synthesis of (2,6-bis(3,6-di-tert-butylcarbazol-9-yl)pyridine-4-yl)methanol (YZ-I-145)

To a solution of (2,6-dibromopyridin-4-yl)methanol (1.0 g, 3.75 mmol), 3,6-di-tert-butylcarbazole (2.3 g, 8.23 mmol), Cu (2.0 g, 31.47 mmol) and 18-crown-6 (32 mg, 0.12 mmol) in 1,2-dichlorobenzene (10.0 ml), was added potassium carbonate (4.0 g, 28.94 mmol) under nitrogen and stirring. The reaction was carried out at 180° C. for 10 hours. After cooling, the reaction mixture was filtrated. The solid residues were carefully washed with THF. Then, THF and 1,2-dichlorobenzene were evaporated from the combined filtration solution. The product was purified by silica gel column chromatography using toluene as an eluent. The pure product as a yellow solid in 1.7 g (68.0%) was obtained by recrystallization from acetone/methanol/water.

$^1$H NMR (CDCl$_3$): δ 8.12 (d, 4H$_{Cz}$, J=1.2 Hz), 7.95 (d, 4H$_{Cz}$, J=8.8 Hz), 7.56 (s, 2 Hp), 7.44 (dd, 4H$_{Cz}$, J$_1$=8.8 Hz, J$_2$=1.2 Hz), 4.94 (s, 2H, OCH$_2$), 1.46 (s, 36H, 12×CH$_3$). $^{13}$C NMR (CDCl$_3$): δ 154.35, 151.82, 143.94, 137.71, 124.45, 123.84, 115.91, 111.68, 110.75, 63.76, 34.84, 32.02.

Device Example 21

This example illustrates the formation of an OLED device using the polymer CZ-I-25 (of example 7) as a hole transport layer.

Under inert atmosphere, 10 mg of CZ-I-25 was dissolved in 1 ml of distilled and degassed chlorobenzene and stirred overnight. Optimized thickness of 30 nm-thick films of CZ-I-25 were fabricated by spin coating from the chlorobenzene solution (60 s@1500 rpm, acceleration 10,000) onto air plasma treated (2 min) indium tin oxide (ITO) coated glass substrates (20Ω/, Colorado Concept Coatings, L.L.C.). Subsequently, a 20 nm thick film of 4,4'-di(carbazol-9-yl)-biphenyl (CBP) was thermally co-evaporated with 6 wt-% fac tris(2-phenylpyridinato N,C$^2$) iridium [Ir(ppy)$_3$] at a rate of 1 Å/s. For the hole-blocking layer, a 40 nm-thick film of bathocuproine (2,9-dimethyl-4,7-diphenyl-1,10-phenanthroline, BCP) was thermally evaporated at a rate of 0.4 Å/s on top of the emissive layer. All evaporated small molecules had previously been purified using gradient zone sublimation. Organic materials were thermally evaporated at a pressure below 1×10$^{-7}$ Torr. Finally, 2.5 nm of lithium fluoride (LiF) as an electron-injection layer and a 200 nm-thick aluminum cathode were vacuum deposited at a pressure below 1×10$^{-6}$ Torr and at rates of 0.1 Å/s and 2 Å/s, respectively. A shadow mask was used for the evaporation of the metal to form five devices with an area of 0.1 cm$^2$ per substrate. At no point during fabrication, the devices were exposed to atmospheric conditions. The configuration of the device is ITO/CZ-I-25 (30 nm)/CPB:Ir(ppy)$_3$ (20 nm)/BCP (40 nm)/LiF (2.5 nm):Al (200 nm). The testing was done right after the deposition of the metal cathode in inert atmosphere without exposing the devices to air.

The performance of the above-referenced device is shown below in Table 1.

TABLE 1

The external quantum efficiency (%) and efficacy (cd/A) (at 1,000 cd/m$^2$) of electroluminescence devices using CZ-I-25 as a hole transport layer (thickness, 30 nm). Average values are averaged over 5 devices.

| | CZ-I-25 |
|---|---|
| Average EL efficiency (%) | 18.5 ± 0.9 |
| Average EL efficacy (cd/A) | 64 ± 3 |
| Maximum EL efficiency (%) | 19.5 |
| Maximum EL efficacy (cd/A) | 100 |

Device Example 22

This example illustrates the formation of an OLED device using one of each of the following carbazole compounds as a hole transport layer: YZ-I-135 (example 15), CZ-I-41 (example 8), YZ-I-57 (example 6), YZ-I-63 (example 5).

Under inert atmosphere, 4 individual solutions of the different carbazole polymers were prepared by dissolving 10 mg of the carbazole polymers in 1 ml of distilled and degassed toluene (resp. chlorobenzene for YZ-I-63) and stirring overnight. 30 nm thick films of the solutions were spin coated from their chlorobenzene solution (60 s@1500 rpm, acceleration 10,000) onto air plasma treated indium tin oxide (ITO) coated glass substrates with a sheet resistance of 20 Ω/(square) (Colorado Concept Coatings, L.L.C.). Subsequently, a 20 nm thick film of 4,4'-di(carbazol-9-yl)-biphenyl (CBP) was thermally co-evaporated with 6 wt-% fac tris(2-phenylpyridinato N,C$^2$)iridium[Ir(ppy)$_3$] at a rate of 1 Å/s. For the hole-blocking layer, a 40 nm-thick film of bathocuproine (2,9-dimethyl-4,7-diphenyl-1,10-phenanthroline, BCP) was thermally evaporated at a rate of 0.4 Å/s on top of the emissive layer. All evaporated small molecules had previously been purified using gradient zone sublimation. Organic materials were thermally evaporated at a pressure below 1×10$^{-7}$ Torr.

Finally, 2.5 nm of lithium fluoride (LiF) as an electron-injection layer and a 200 nm-thick aluminum cathode were vacuum deposited at a pressure below 1×10$^{-6}$ Torr and at rates of 0.1 Å/s and 2 Å/s, respectively. A shadow mask was used for the evaporation of the metal to form five devices with an area of 0.1 cm$^2$ per substrate. At no point during fabrication, the devices were exposed to atmospheric conditions. The testing was done right after the deposition of the metal cathode in inert atmosphere without exposing the devices to air.

Figure 2:
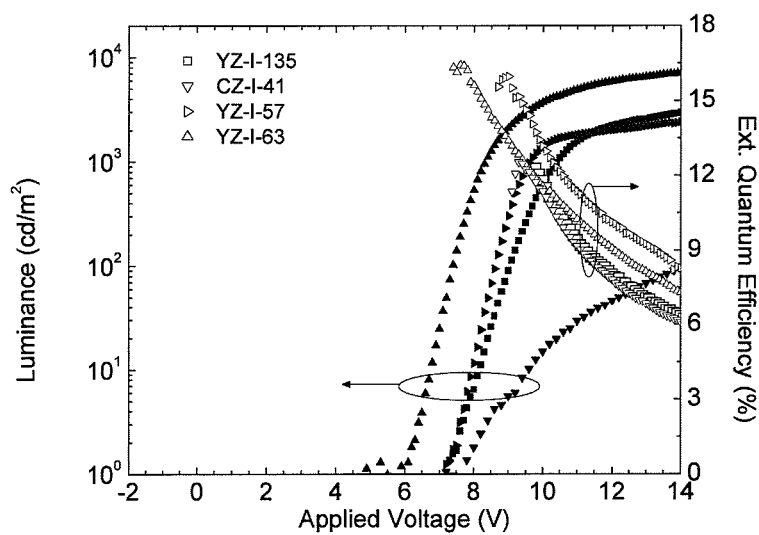
FIG. 2. Luminance and the external quantum efficiency (EQE) curves for the devices of Example 22, using either YZ-I-135, CZ-I-41, YZ-I-57, or YZ-I-63 as the hole transport layer.

The configuration of the device is ITO/carbazole compound (YZ-I-135 CZ-I-41, YZ-I-57 or YZ-I-63) (30 nm)/CBP:Ir(ppy)$_3$ (20 nm)/BCP (40 nm)/LiF (2.5 nm):Al (200 nm). FIG. 2 shows the luminance and the external quantum efficiency (EQE) curves for the devices. The performances of the above-referenced compounds are shown below in Table 2.

TABLE 2

The external quantum efficiency (%) and efficacy (cd/A) (at 1,000 cd/m²) of electroluminescence devices using different carbazole (YZ-I-135, CZ-I-41, YZ-I-57, and YZ-I-63) as hole transport layer (thickness, 30 nm).

|  | YZ-I-135 | CZ-I-41 | YZ-I-57 | YZ-I-63 |
|---|---|---|---|---|
| EL efficiency (%) | 10.3 ± 1.1 | 9.4 ± 0.3 | 13.9 ± 1.0 | 14.1 ± 1.1 |
| EL efficacy (cd/A) | 11 ± 2 | 32 ± 3 | 4 ± 1 | 18 ± 2 |

Device Example 23

This example illustrates the formation of an OLED device using one of each of the following carbazole compounds as a host in the emissive layer: YZ-I-133 (example 14), YZ-I-135 (example 15) and YZ-I-57 (example 6). The configuration of the device is ITO/Poly-TPD-f (35 nm)/carbazole host: Ir(ppy)$_3$ (30 nm)/BCP (40 NM)/LiF (2.5 nm): Al (200 nm).

Where poly-TPD-f is:

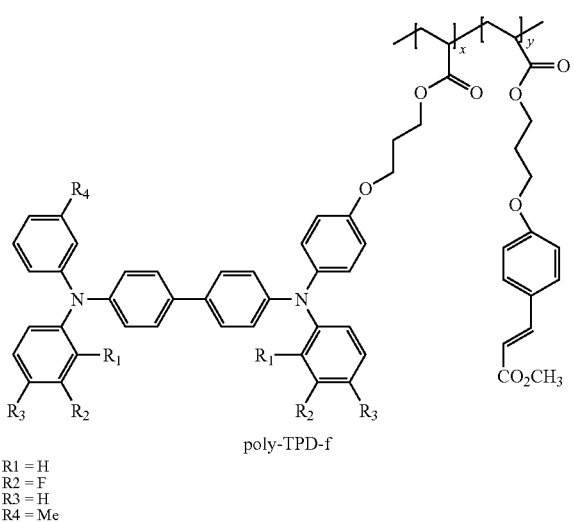

poly-TPD-f

R1 = H
R2 = F
R3 = H
R4 = Me

For the hole-transport layer, 10 mg of Poly-TPD-F were dissolved in 1 ml of distilled and degassed toluene. For the emissive layer, a solution of either of YZ-I-133 and YZ-I-135 was prepared by dissolving 9.5 mg of the carbazole polymers and 0.6 mg of fac tris(2-phenylpyridinato N,C$^{2'}$) iridium[Ir(ppy)$_3$] in 1 ml of distilled and degassed chlorobenzene. Alternatively, 4.5 mg YZ-I-57 and 0.3 mg of fac tris(2-phenylpyridinato N,C$^{2'}$) iridium[Ir(ppy)$_3$] were dissolved in 1 ml of distilled and degassed chloroform. All solutions were made under inert atmosphere and were stirred overnight.

35 nm thick films of the hole-transport poly-TPD-F were spin coated (60 s@1500 rpm, acceleration 10,000) onto air plasma treated indium tin oxide (ITO) coated glass substrates with a sheet resistance of 20 Ω/square (Colorado Concept Coatings, L.L.C.). Films were cross-linked using a standard broad-band UV light with a 0.7 mW/cm² power density for 1 min. Subsequently, a 30 nm film of the emitting layer from the solution containing one of the carbazole polymer hosts and Ir(ppy)$_3$ was spin coated on top of the cross-linked hole-transport layer (60 s@1500 rpm, acceleration 10,000). For the hole-blocking layer, bathocuproine (2,9-dimethyl-4,7-diphenyl-1,10-phenanthroline, BCP) which was purified using gradient zone sublimation was then thermally evaporated on top of the emissive layer at a rate of 0.4 Å/s and at a pressure below 1×10$^{-7}$ Torr.

Finally, 2.5 nm of lithium fluoride (LiF) as an electron-injection layer and a 200 nm-thick aluminum cathode were vacuum deposited at a pressure below 1×10$^{-6}$ Torr and at rates of 0.1 Å/s and 2 Å/s, respectively. A shadow mask was used for the evaporation of the metal to form five devices with an area of 0.1 cm² per substrate. At no point during fabrication, were the devices exposed to atmospheric conditions. The testing was done right after the deposition of the metal cathode in inert atmosphere without exposing the devices to air.

Figure 3:
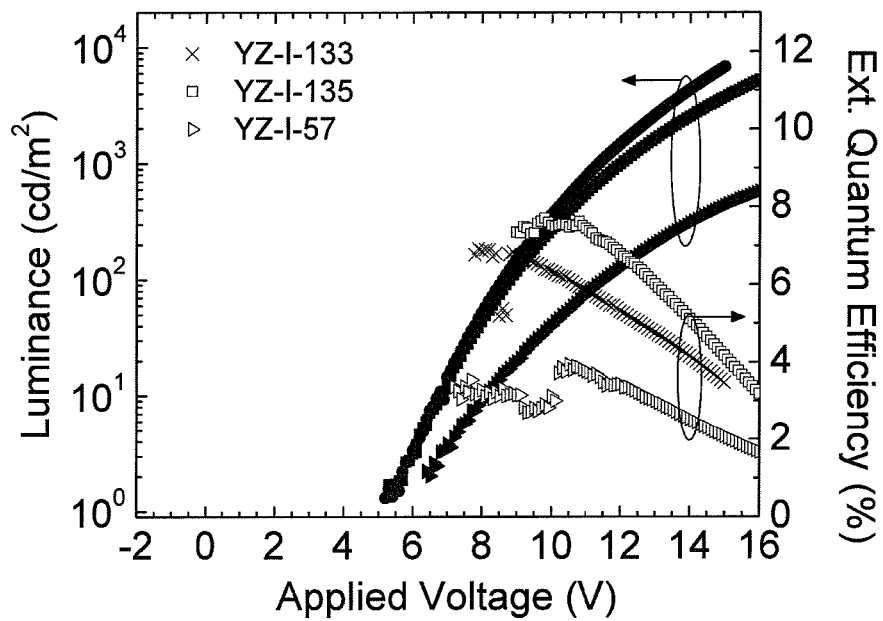
FIG. 3. Luminance and the external quantum efficiency (EQE) curves for the devices of Example 23, using either YZ-I-133, YZ-I-135 or YZ-I-57 as hosts in the emissive layer.

FIG. 3 shows the luminance and the external quantum efficiency (EQE) curves for the devices. The performance of the above-reference compounds are shown below in Table 3.

TABLE 3

The external quantum efficiency (%) and efficacy (cd/A) (at 100 cd/m²) of electroluminescence devices using carbazole (YZ-I-133, YZ-I-135, and YZ-I-57) as host material in the emissive layer (thickness, 30 nm). Values are averaged over 5 devices.

|  | YZ-I-133 | YZ-I-135 | YZ-I-57 |
|---|---|---|---|
| EL efficiency (%) | 6.3 ± 0.5 | 6.0 ± 0.9 | 3.2 ± 0.4 |
| EL efficacy (cd/A) | 21 ± 2 | 20 ± 3 | 11 ± 2 |

Device Example 24

This example illustrates the formation of an OLED device using the following carbazole compounds as a host in the emissive layer: YZ-I-135 (example 15), YZ-I-63 (example 5), CZ-I-25 (example 7) and CZ-I-41 (example 8).

For the hole-transport layer, 10 mg of Poly-TPD-F were dissolved in 1 ml of distilled and degassed toluene. For the emissive layer, a solution of either CZ-I-25 or CZ-I-41 were prepared by dissolving 9.5 mg of the carbazole polymers and 0.6 mg of fac tris(2-phenylpyridinato N,C$^{2'}$) iridium[Ir(ppy)$_3$] in 1 ml of distilled and degassed chlorobenzene. Alternatively, 4.5 mg of YZ-I-63 and 0.3 mg of fac tris(2-phenylpyridinato N,C$^{2'}$) iridium[Ir(ppy)$_3$] were dissolved in 1 ml of distilled and degassed chloroform. All solutions were made under inert atmosphere and were stirred overnight.

35 nm thick films of the hole-transport material were spin coated (60 s@1500 rpm, acceleration 10,000) onto air plasma treated indium tin oxide (ITO) coated glass substrates with a sheet resistance of 20Ω/ (Colorado Concept Coatings, L.L.C.). Films were cross-linked using a standard broad-band UV light with a 0.7 mW/cm² power density for 1 minute. Subsequently, a 30 nm film of the emitting layer was spin coated, from one of the three Carbazole polymer: Ir(ppy)$_3$) solutions, on top of the cross-linked hole-transport layer (60 s@1500 rpm, acceleration 10,000). For the hole-blocking layer, bathocuproine (2,9-dimethyl-4,7-diphenyl-1,10-phenanthroline, BCP) was first purified using gradient zone sublimation, and a film of 40 nm was then thermally evaporated at a rate of 0.4 Å/s and at a pressure below 1×10$^{-7}$ Torr on top of the emissive layer.

Finally, 2.5 nm of lithium fluoride (LiF) as an electron-injection layer and a 200 nm-thick aluminum cathode were vacuum deposited at a pressure below 1×10$^{-6}$ Torr and at rates of 0.1 Å/s and 2 Å/s, respectively. A shadow mask was used for the evaporation of the metal to form five devices with an area of 0.1 cm² per substrate. At no point during fabrication were the devices exposed to atmospheric conditions. The testing was done right after the deposition of the metal cathode in inert atmosphere without exposing the devices to air. The configuration of the device is ITO/Poly-TPD-F/(35 nm)/carbazole host:Ir(ppy)$_3$ (30 nm)/BCP (40)/LiF (2.5 nm):Al (200 nm).

Figure 4:
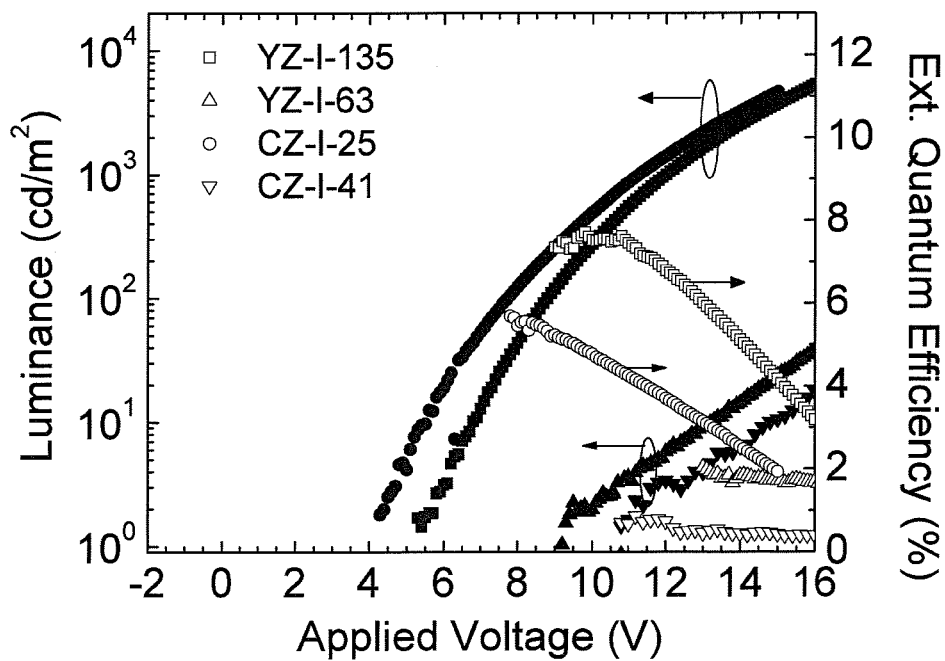
FIG. 4. Luminance and the external quantum efficiency (EQE) curves for the devices of Example 24 using YZ-I-135, YZ-I-63, CZ-I-25 or CZ-I-41 as hosts in the emissive layer.

FIG. 4 shows the luminance and the external quantum efficiency (EQE) curves for the devices. The performances of the above-referenced compounds are shown below in Table 4.

TABLE 4

The external quantum efficiency (%) and efficacy (cd/A) (100 cd/m²) of electroluminescence devices using carbazole (YZ-I-135, YZ-I-63, CZ-I-25, and CZ-I-41) as host material in the emissive layer (thickness, 30 nm).

|  | YZ-I-135 | YZ-I-63 | CZ-I-25 | CZ-I-41 |
|---|---|---|---|---|
| EL efficiency (%) | 6.0 ± 0.9 | 1.4.0 ± 0.1 | 5.2 ± 0.6 | 0.3 ± 0.1 |
| EL efficiency (cd/A) | 2o ± 2 | 4 ± 1 | 18 ± 2 | 1 ± 1 |

Device Example 25

This example illustrates the OLED device fabrication and characterization using either CZ-I-25 (example 7) or YZ-I-133 (example 14) as the polymer host and the FPt emitter. Where FPt:

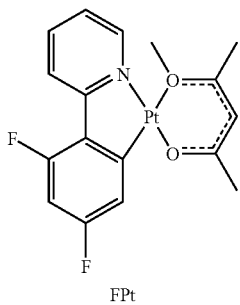

FPt

Figure 5:
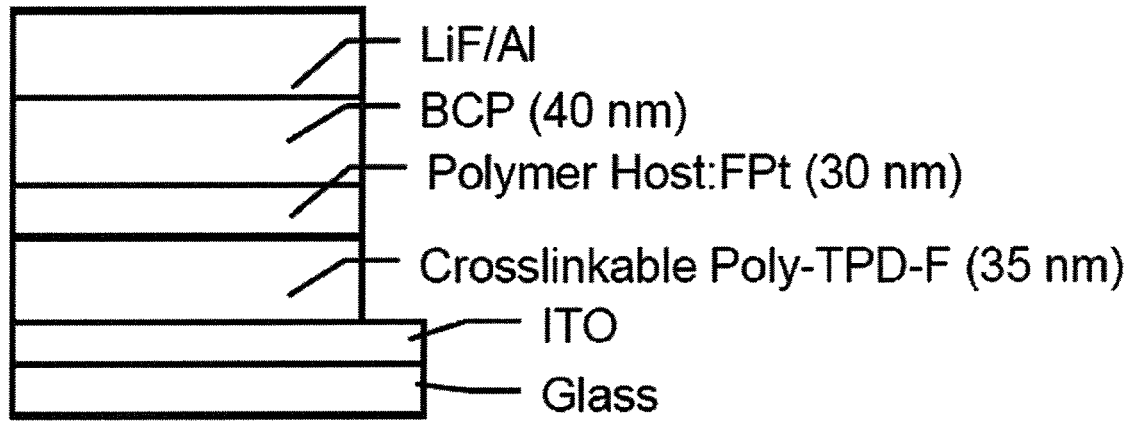
FIG. 5. W(OLED) Device architecture of the W(OLED) for testing the CZ-1-25 and YZ-I-133 polymer hosts (See Example 25). Where Al is the aluminum cathode, LiF is a lithium fluoride electron injecting layer, BCP is a hole blocking layer, Cross-linkable Poly-TPD-f is the hole transport layer and ITO is an indium tin oxide anode.

The device architecture of the W(OLED) for testing the CZ-I-25 and YZ-I-133 polymer hosts is depicted in FIG. 5. First a hole transport layer of cross-linkable poly-TPD-F was spin coated (10 mg/ml in toluene) at 1500 RPM (60 s) onto air plasma treated (2 min) indium tin oxide (ITO) glass substrates (20Ω/, Colorado Concept Coatings, L.L.C.). The Poly-TPD-f films were then cross-linked for 1 min under 0.7 mW/cm² of a broad band UV light source. Then on the top of hole transport layer, 30 nm of the emissive was spin coated (1000 RPM, 60 s) from the mixture of CZ-I-25 or YZ-I-133 polymer host and the FPt emitter using 18 wt % and 15 wt % concentration for CZ-I-25 and YZ-I-133, respectively using a chlorobenzene solution (10 mg/ml). A hole-blocking layer of bathocuproine (2,9-dimethyl-4,7-diphenyl-1,10-phenanthroline, BCP) (40 nm) was then thermally evaporated at a rate of 0.4 Å/s and at a pressure below 1×10⁻⁷ Torr on top of the emissive layer. Finally, 2.5 nm of lithium fluoride (LiF) as an electron-injection layer and a 200 nm thick aluminum cathode were vacuum deposited at a pressure below 1×10⁻⁶ Torr and at rates of 0.1 Å/s and 2 Å/s, respectively. A shadow mask was used for the evaporation of the metal to form five devices with an area of 0.1 cm² per substrate. All the fabrication steps were carrier out in a nitrogen filled glove box. The testing was done right after the deposition of the metal cathode without exposing the devices to air.

Figure 6:
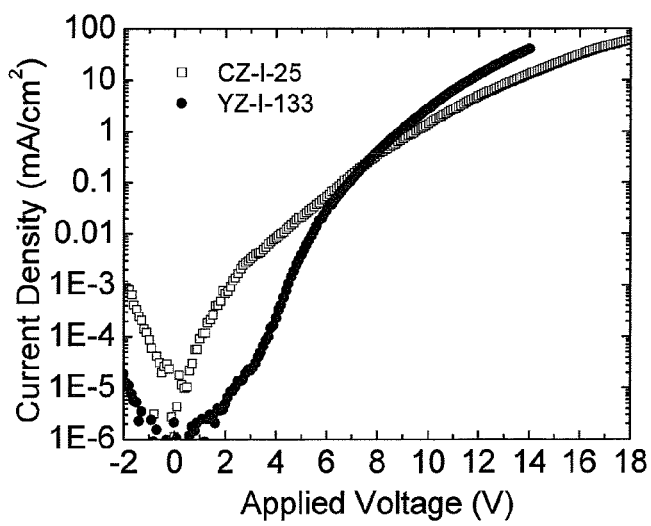
FIG. 6. Current density-voltage vs. Applied Voltage for devices utilizing either CZ-I-25 or YZ-I-133 polymer host materials doped with the F—Pt emitter (See example 25)
Figure 7:
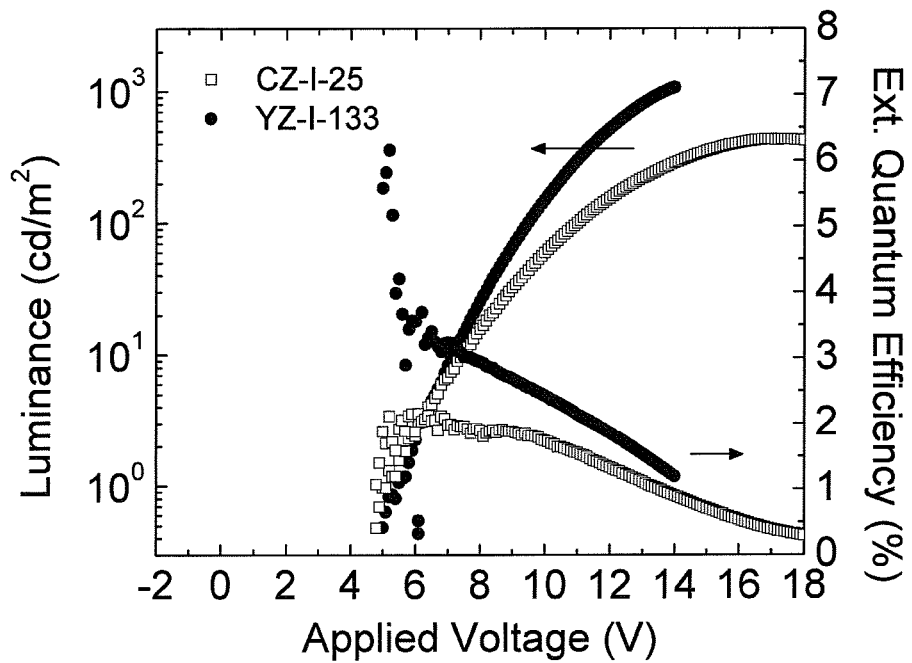
FIG. 7. Luminance-Voltage-External Quantum Efficiency for devices using either CZ-I-25 or YZ-I-133 as the polymer host and the F—Pt emitter (See example 25)
Figure 8:
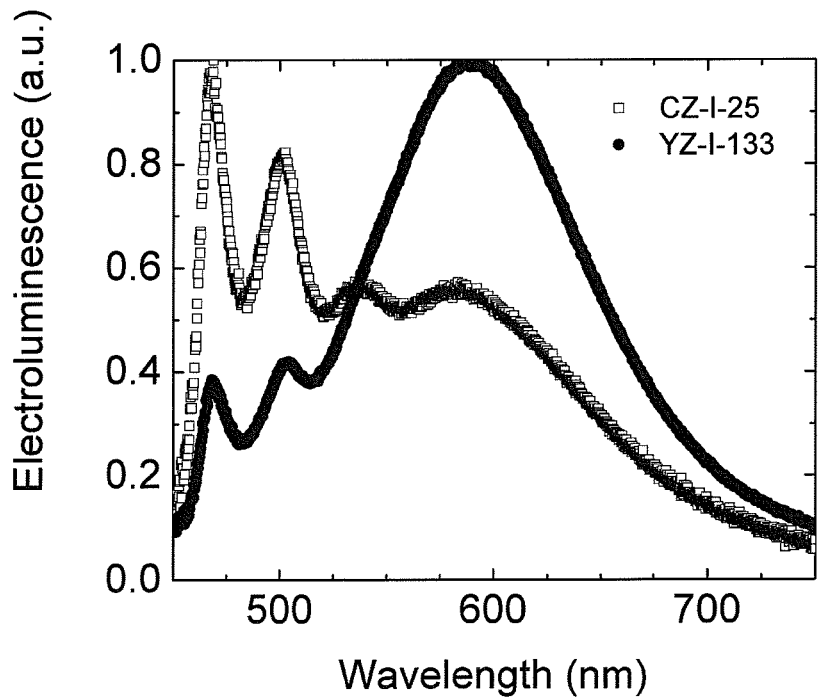
FIG. 8. Electroluminescence spectra of the W(OLED) devices using either CZ-I-25 or YZ-I-133 as host polymers (See example 25)

FIG. 6 shows the current density-voltage (J-V) characteristics for the two devices utilizing CZ-I-25 and YZ-I-133 polymer host materials doped with the FPt emitter. The luminance and the external quantum efficiency (EQE) curves for the respective devices are shown in FIG. 7. It can be seen that a higher luminance and EQE was observed for YZ-I-133 (15 wt % F—Pt doped) in comparison to the CZ-I-25 (18 wt % F—Pt doped) based WOLED. The external quantum efficiency of 2.3+0.2% (5±1 cd/A), and 1.5+0.1% (3±1 cd/A) was observed for the case of CZ-I-25 and YZ-1-133 host, respectively. Further, the electroluminescence (EL) spectra of these WOLED devices were measured to extract the Commission Internationale de l'Eclairage (CIE) coordinate, and the color rendering index (CRI) to see the prospects of these devices in W(OLED) applications. The EL spectra of the devices using CZ-I-25 and YZ-I-133 hosts based devices are compared in FIG. 8. The extracted CIE and the CRI values from these spectra are summarized in Table 5. It can be seen that the a CIE coordinate (0.34, 0.35) which is close to the white point is realized in the WOLED device using the CZ-I-25 host doped with 18 wt % of F—Pt emitter. However, the WOLED based on YZ-I-133 host with 15 wt % FPt emitter resulted into a strong orange-red emission. These prior results show that the newly synthesized polymer hosts could be the potential hosts for the solution processable WOLEDs.

TABLE 5

The electroluminescent properties of the W (OLED) device using CZ-I-25 host doped with 18 wt % FPt, and the YZ-I-133 host doped 15 wt % FPt.

| Host | FPt-content | CIE 1931 | | CRI |
|---|---|---|---|---|
| | | X | Y | |
| CZ-I-25 | 18 wt % | 0.34 | 0.42 | 72 |
| YZ-I-133 | 15 wt % | 0.45 | 0.44 | 74 |

Device Example 26

This example illustrates the polymer host CZ-I-154 and poly-CBP-fluorene in green OLEDs.

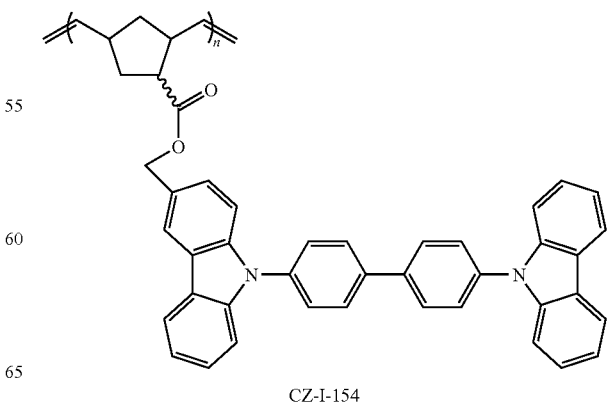

CZ-I-154

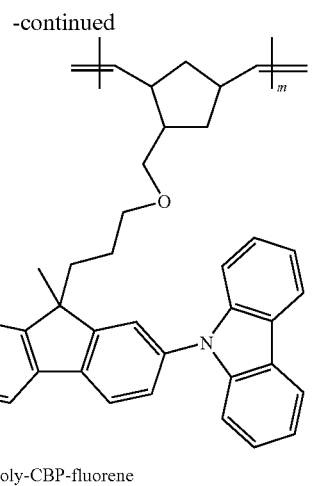

Poly-CBP-fluorene

Figure 9:
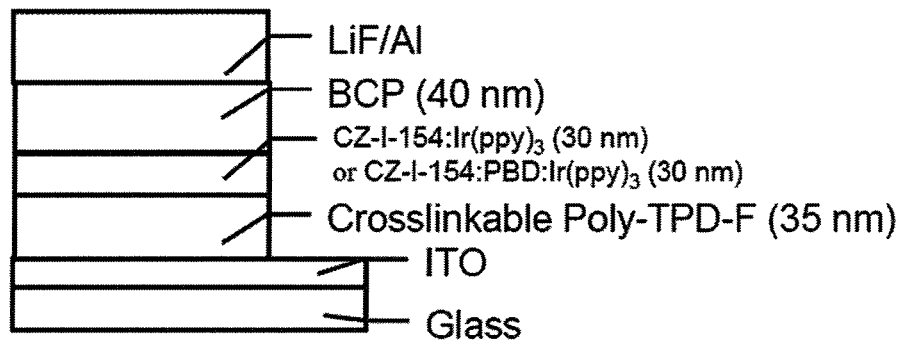
FIG. 9. Device structure of the green OLED using poly-CBP (CZ-I-154) or poly-CBP: PBD hosts (See example 26)

The structure of the OLED device for testing the polymer hosts CZ-I-154 and poly-CBP-fluorene for the green emitter Ir(ppy)$_3$ is shown in FIG. 9. The hole transport layer of crosslinkable poly-TPD-F, hole blocking layer of BCP, the injection layer LiF and the Al cathode were deposited as described earlier in example 23 for the WOLEDs. For the emitting layer, the host CZ-I-154 and the green emitter Ir(ppy$_3$) (6 wt %) were dissolved in a chlorobenzene (10 mg/ml) and stirred overnight. The emitting layer was spin coated on the top of the hole transport layer at 1000 RPM to form a 30 nm layer.

Figure 10:
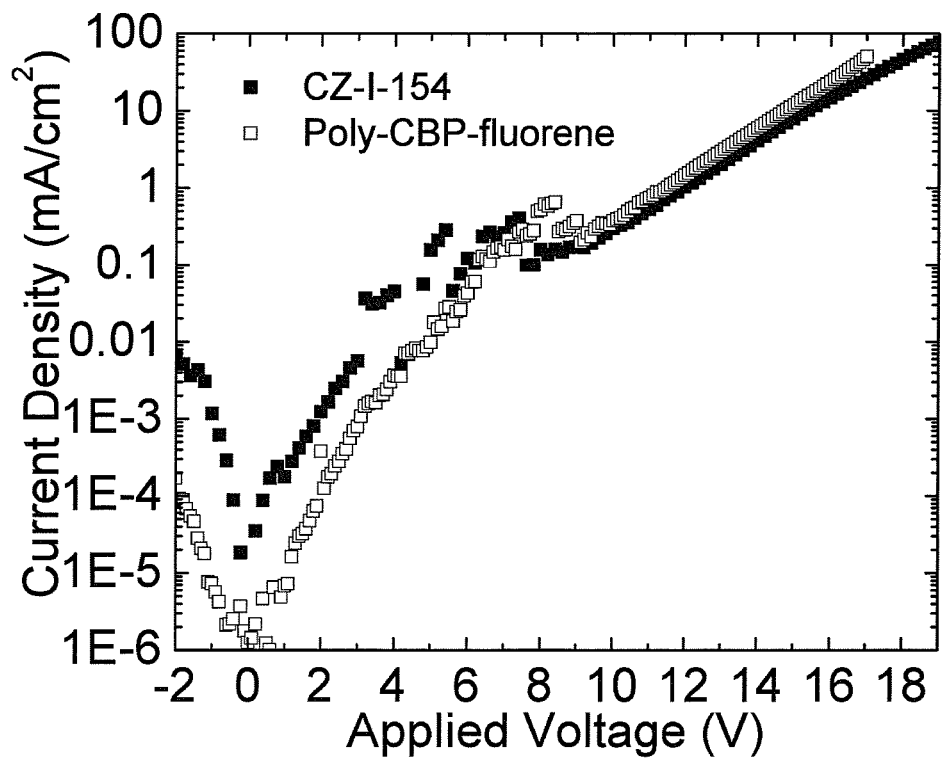
FIG. 10. Current density-Voltage (J-V) for the green OLEDs using poly-CBP (CZ-I-154) and poly-CBP-fluorene hosts (See example 26).
Figure 11:
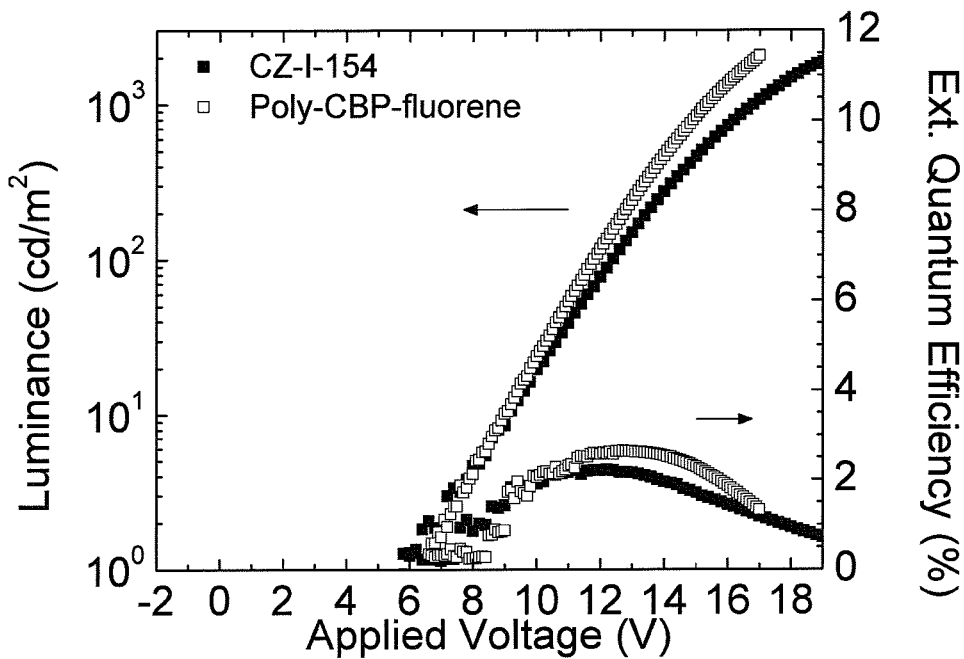
FIG. 11. The luminance-external quantum efficiency (EQE) curves for the OLEDs using poly-CBP (CZ-I-154) and poly-CBP-fluorene polymer hosts (See example 26).

FIG. 10 shows the current density-voltage (J-V) characteristics of the OLEDs utilizing either the polymer host CZ-I-154 or poly-CBP-fluorene. The respective luminance and the external quantum efficiency (EQE) curves are shown in FIG. 11. Similar efficiencies were observed for CZ-I-154 and poly-CBP-fluorene host. The observed EQEs were 2.1±0.1% (efficacy of 7±1 cd/A) and 2.2±0.3% (efficacy of 7±1 cd/A), poly—CBP-fluorene and CZ 4-154 based OLEDs, respectively.

It was discovered that the CZ-I-154 devices could benefit by incorporating a small molecule electron transport material. Therefore, a PBD small molecule was mixed into the emissive layer, here PBD is:

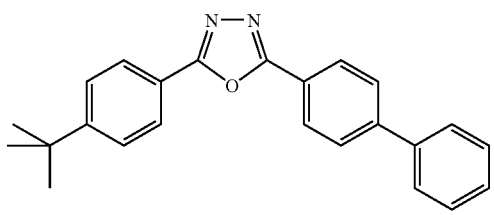 [SMILES: CC(C)(C)c1ccc(-c2nnc(-c3ccc(-c4ccccc4)cc3)o2)cc1]

The performance was compared to that of control devices without PBD. Therefore, the emissive layer was spin coated from a mixture of CZ-I-154:PBD:Ir(ppy)$_3$ in the ratio of 7:2.4:0.6 mg/ml (10 mg/ml total).

Figure 12:
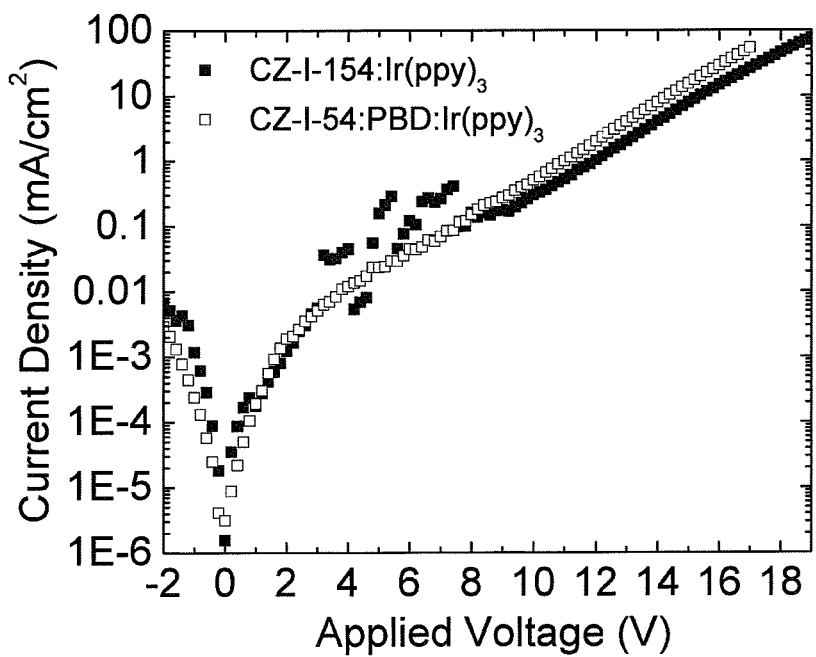
FIG. 12. Comparison of the current density (J-V) characteristics of OLEDs based on poly-CBP host with and without the electron transport PBD in the emissive layer (See example 26).
Figure 13:
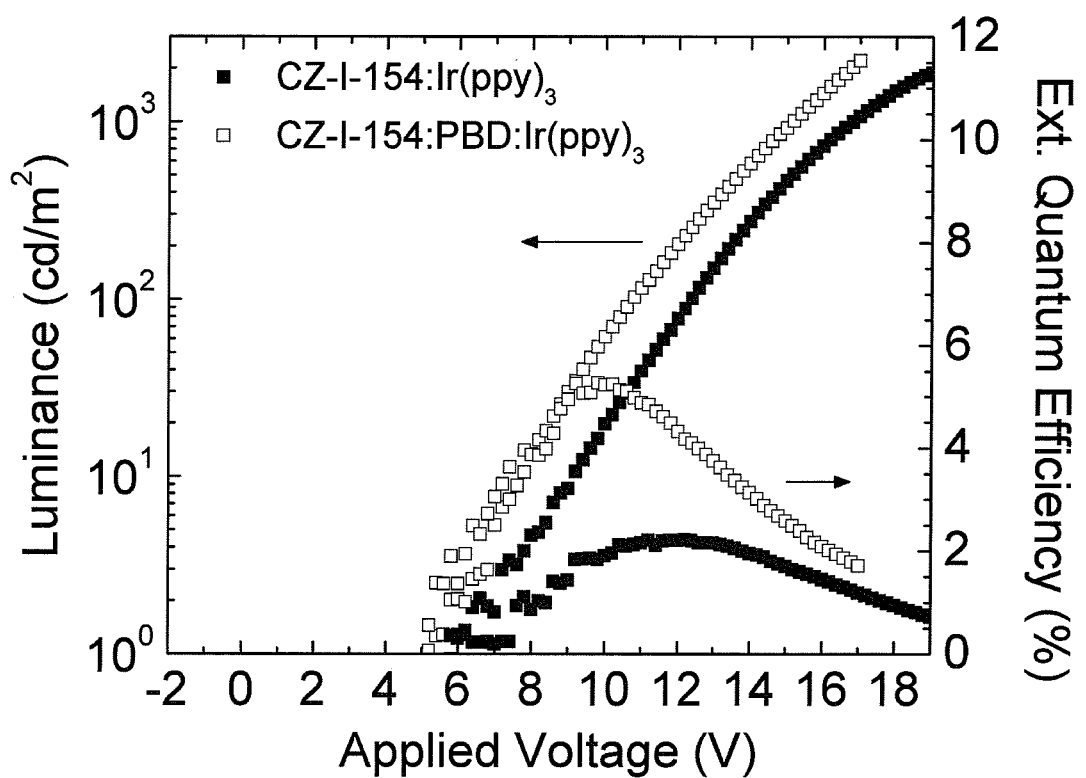
FIG. 13. Comparison of the luminance and EQE curves as a function of applied voltage for the OLEDs based on poly-CBP host with and without the electron transport PBD in the emissive layer (See example 26).

The current density-voltage (J-V) characteristics of the OLED devices using CZ-I-154 host with and without the PBD electron transport molecule are compared in FIG. 12. The luminance and EQE curves as a function of applied voltage are shown in FIG. 13 for the respective devices. It can be seen that in the OLEDs using the CZ-I-154 with the addition of the PBD resulted into a higher luminance and the EQE in comparison to the OLED without the PBD addition. Compared to the control OLED device with only CZ-I-154 (EQE=2.1±0.1% (efficacy of 7±1 cd/A) the EQE was doubled and the efficiency of 4.2±0.8% (efficacy of 14±3 cd/A) was observed.

These results suggest that the luminescence efficiency of emissive layers comprising CZ-I-154 as a hole carrier may be improved by the addition of charge balancing electron carriers.

While this invention has been described in terms of what are presently considered to be the most practical and preferred embodiments, it is to be understood that the invention need not be limited to the enclosed embodiment. To the contrary, it is intended to cover various modifications and similar arrangements included within the spirit and scope of the appended claims which are to be accorded with the broadest interpretation so as to encompass all such modifications and similar structures. Therefore, the above description and illustration should not be taken as limiting the scope of the present invention which is defined by the appended claims.

The invention claimed is:
1. A compound represented by the formulas:

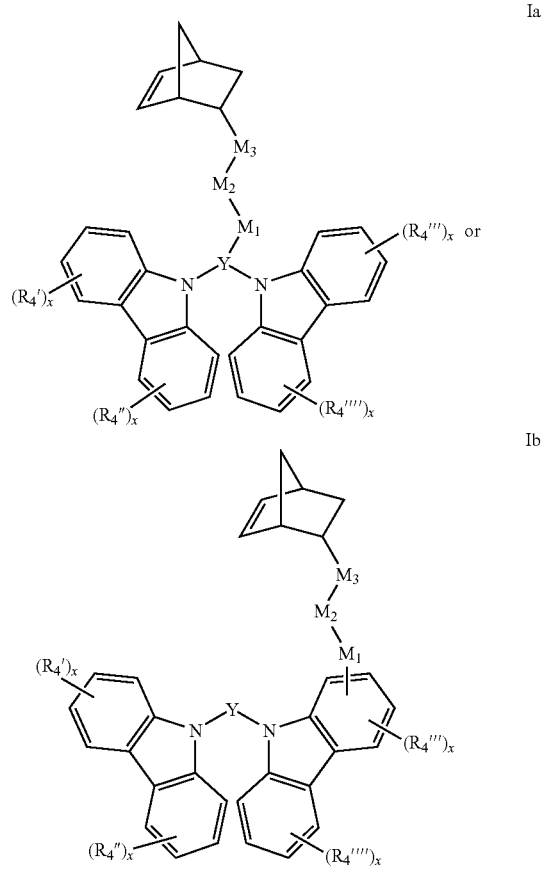

wherein:
each optional R4', R4", R4'", or R4"" group is independently selected from one or more $C_{1-20}$ alkyl, aryl, or alkoxy groups,
each x is an independently selected integer 0, 1, 2, 3 or 4,
Y is selected from the group consisting of carbazole, purine, indole, indoline, carboline, naphthalene, azulene, anthracene, phenanthrene, benzene, phenyl, pyridine, pyrrole, oxazole, thiazole, pyrrole, imidazole, furan, thiophene, triazole, pyrazole, isoxazole, pyrazine, pyridazine, and triazine rings, wherein;

$M_1$ and $M_3$ are optional or independently selected from

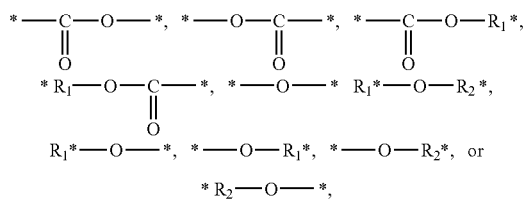

and are bound to the norbornene, Y, or carbazole groups at the positions indicated by *;

$R_1$ and $R_2$ are optional independently selected $C_{1-20}$ alkane diyl, alkene diyl, alkyne diyl, or arene diyl groups;

and optional $M_2$ is a $C_{1-20}$ alkane diyl, alkene diyl, or arene diyl group.

2. The compound of claim 1, having the structure:

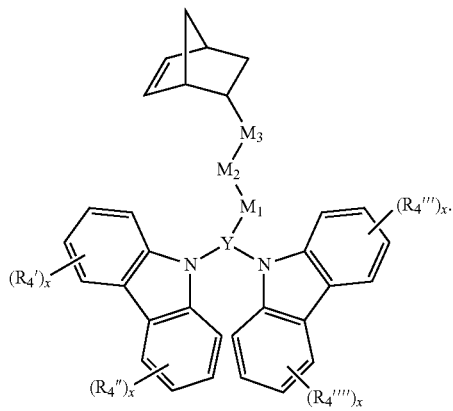

Ia

3. The compound of claim 1, having the structure:

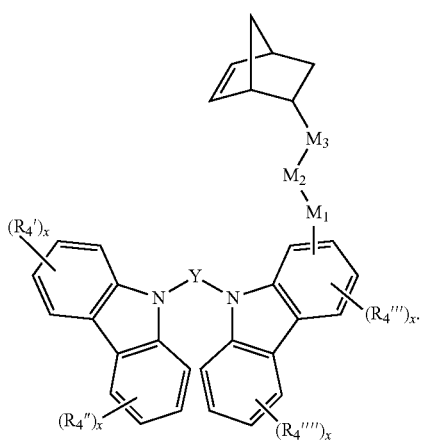

Ib

4. The compound of claim 1 wherein $R_1$ and $R_2$ are $C_{1-11}$ alkane diyls.

5. The compound of claim 1 wherein $M_2$ is absent or is a $C_{1-11}$ alkane diyl.

6. The compound of claim 1 wherein $R_4'$, $R_4''$, $R_4'''$, $R_4''''$ are independently select $C_{1-6}$ alkyl or alkoxy groups.

7. The compound of claim 1 wherein $M_3$-$M_2$-$M_1$ is

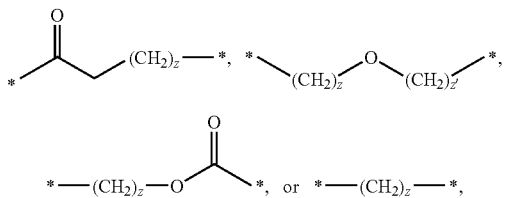

where z and z' are independently selected integers 0, 1, 2, 3, 4, 5, 6, 7, 8, 9, 10, 11, or 12.

8. The compound of claim 1, wherein Y comprises a ring selected from the group consisting of carbazole, purine, indole, indoline, and carboline rings.

9. A process for preparing a polymer or copolymer comprising a) mixing at least one monomeric compound of claim 1 with a ring opening metathesis catalyst, and b) polymerizing the mixture to form a polymer comprising at least some polynobornenyl repeat units having the structure:

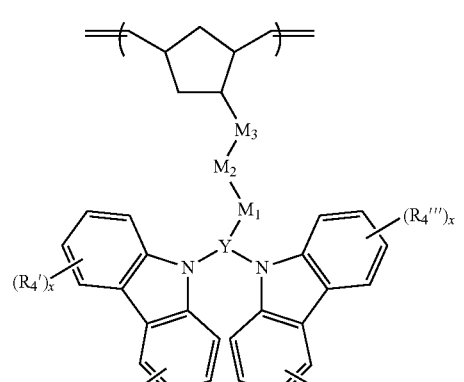

III

IV

10. A polymer represented by the formulas:

[Structure III: norbornene-based polymer with M₃-M₂-M₁-Y linker to bis-carbazole system with (R4')ₓ, (R4''')ₓ, (R4'')ₓ, (R4'''')ₓ substituents]

[Structure IV: similar norbornene-based polymer variant]

wherein:
each optional R4', R4", R4''', or R4'''' group is independently selected from one or more $C_{1-20}$ alkyl, aryl, or alkoxy groups,
each x is an independently selected integer 0, 1, 2, 3 or 4,
n is an integer from 1 to 2000,
Y is selected from the group consisting of carbazole, purine, indole, indoline, carboline, naphthalene, azulene, anthracene, phenanthrene, benzene, phenyl, pyridine, pyrrole, oxazole, thiazole, pyrrole, imidazole, furan, thiophene, triazole, pyrazole, isoxazole, pyrazine, pyridazine, and triazine rings;
wherein;
$M_1$ and $M_3$ are optional or independently selected from

[linker group structures: *—C(=O)—O—*, *—O—C(=O)—*, *—C(=O)—O—R₁*, *R₁—O—C(=O)—*, *—O—* R₁*—O—R₂*, R₁*—O—*, *—O—R₁*, *—O—R₂*, or *R₂—O—*]

and are bound to the norbornene, Y, or carbazole groups at the positions indicated by *,
$R_1$ and $R_2$ are optional independently selected $C_{1-20}$ from the group consisting of alkane diyl, alkene diyl, alkyne diyl, or arene diyl groups; and optional $M_2$ is a $C_{1-20}$ alkane diyl, alkene diyl, alkyne diyl, or arene diyl group.

11. The polymer of claim 10 having the structure:

[Structure IIa]

12. The polymer of claim 10 having the structure:

[Structure IIb]

13. The polymer of claim 10, wherein $R_1$ and $R_2$ are $C_{1-11}$ alkane diyls.

14. The polymer of claim 10, wherein $M_2$ is absent or is a $C_{1-11}$ alkane diyl.

15. The polymer of claim 10, wherein $R_4'$, $R_4''$, $R_4'''$, $R_4''''$ are independently selected $C_{1-6}$ alkyl or alkoxy groups.

16. The polymer of claim 10, wherein $M_3$-$M_2$-$M_1$ is

[structures: *—C(=O)—(CH₂)_z—*, *—(CH₂)_z—O—(CH₂)_{z'}—*, *—(CH₂)_z—O—C(=O)—*, or *—(CH₂)_z—*,]

where z and z' are independently selected integers 0, 1, 2, 3, 4, 5, 6, 7, 8, 9, 10, 11 or 12.

17. The polymer of claim 10, wherein Y comprises a ring selected from the group consisting of carbazole, purine, indole, indoline, and carboline rings.

18. An organic electroluminescent device comprising the polymer of claim 10.

19. The compound according to claim 1, being represented by the formulas selected from the group consisting of:
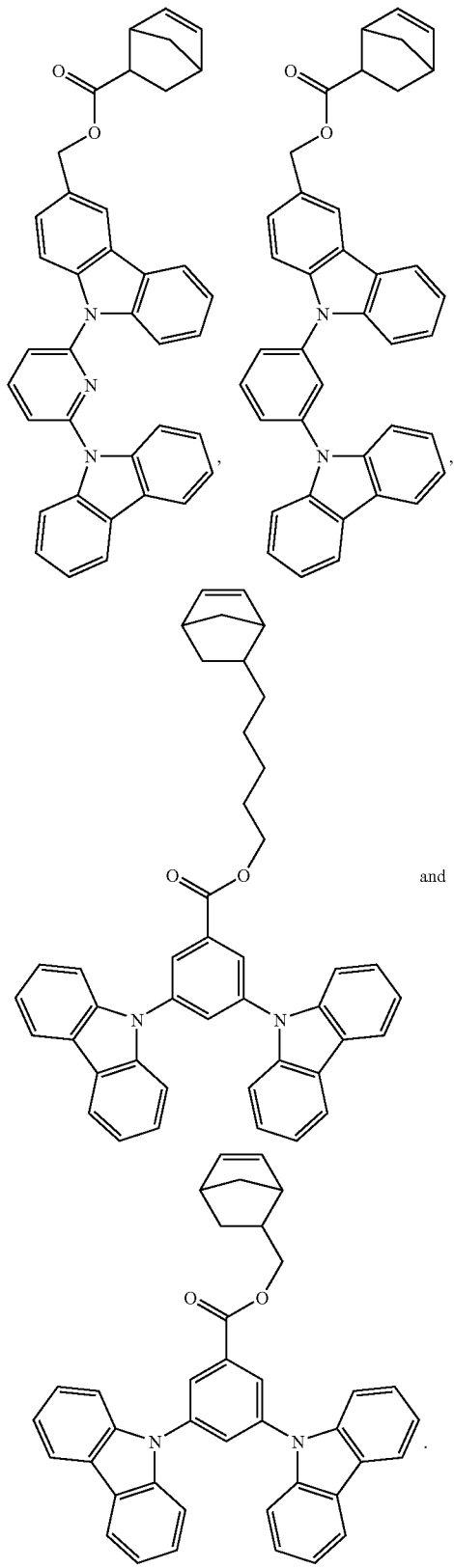
20. The polymer according to claim 10, being represented by the formulas selected from the group consisting of:
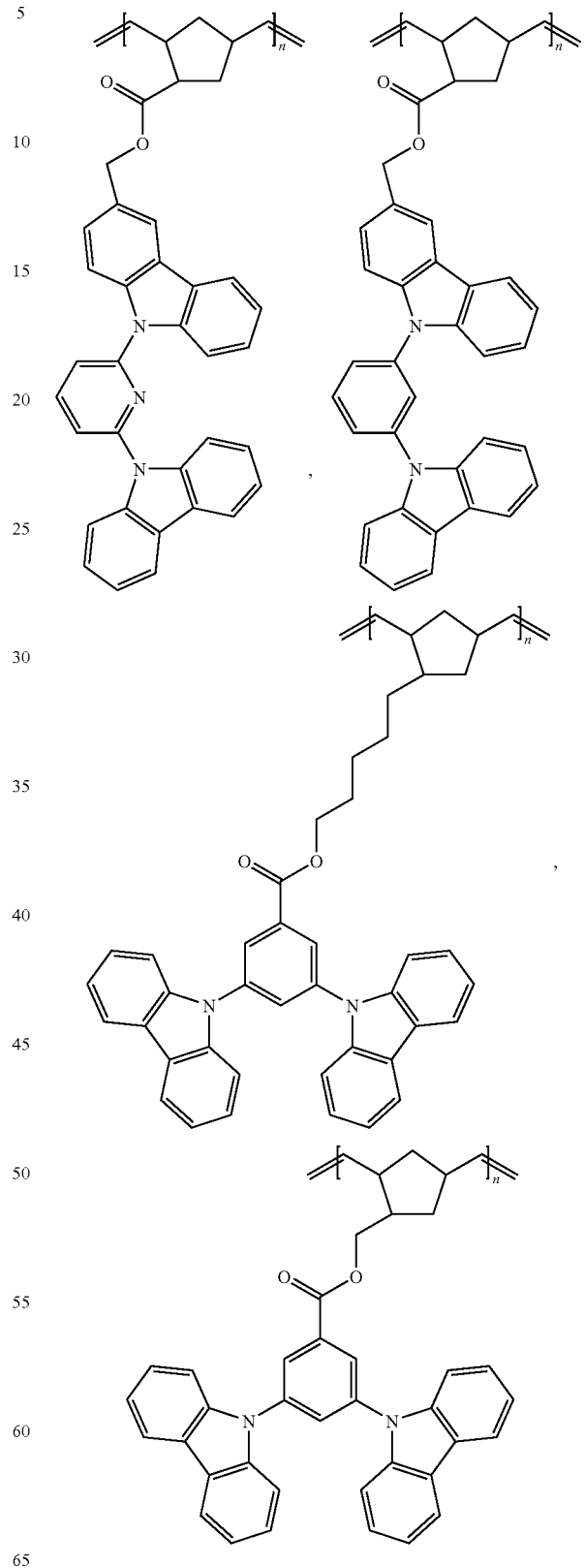
and mixtures thereof.

21. A compound represented by:
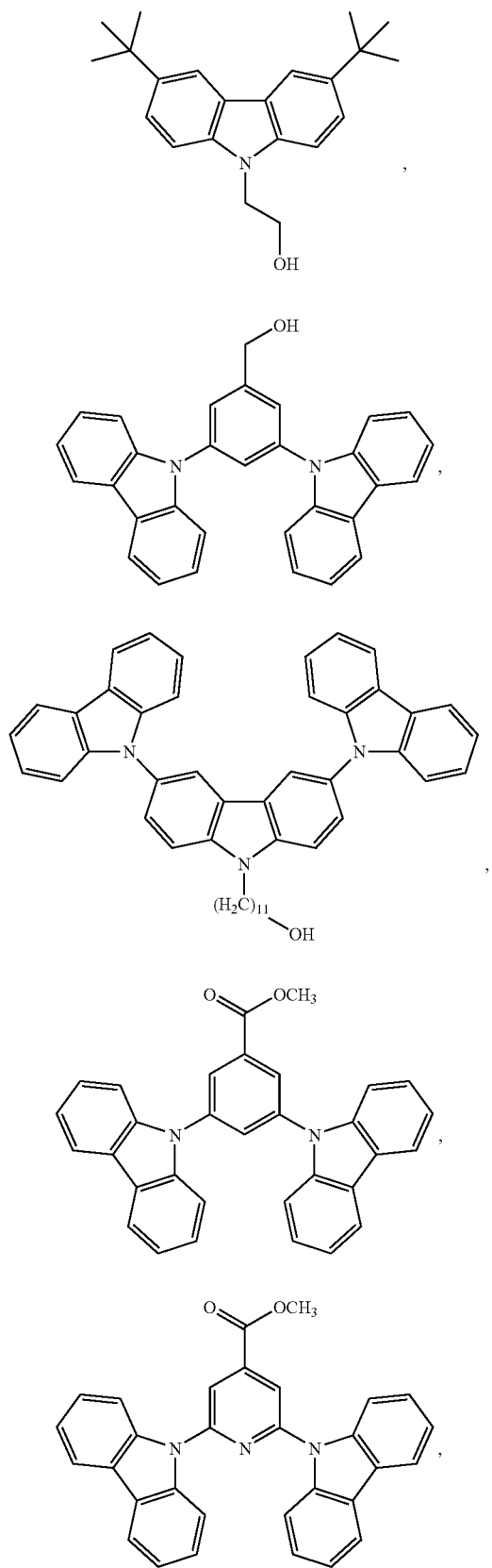
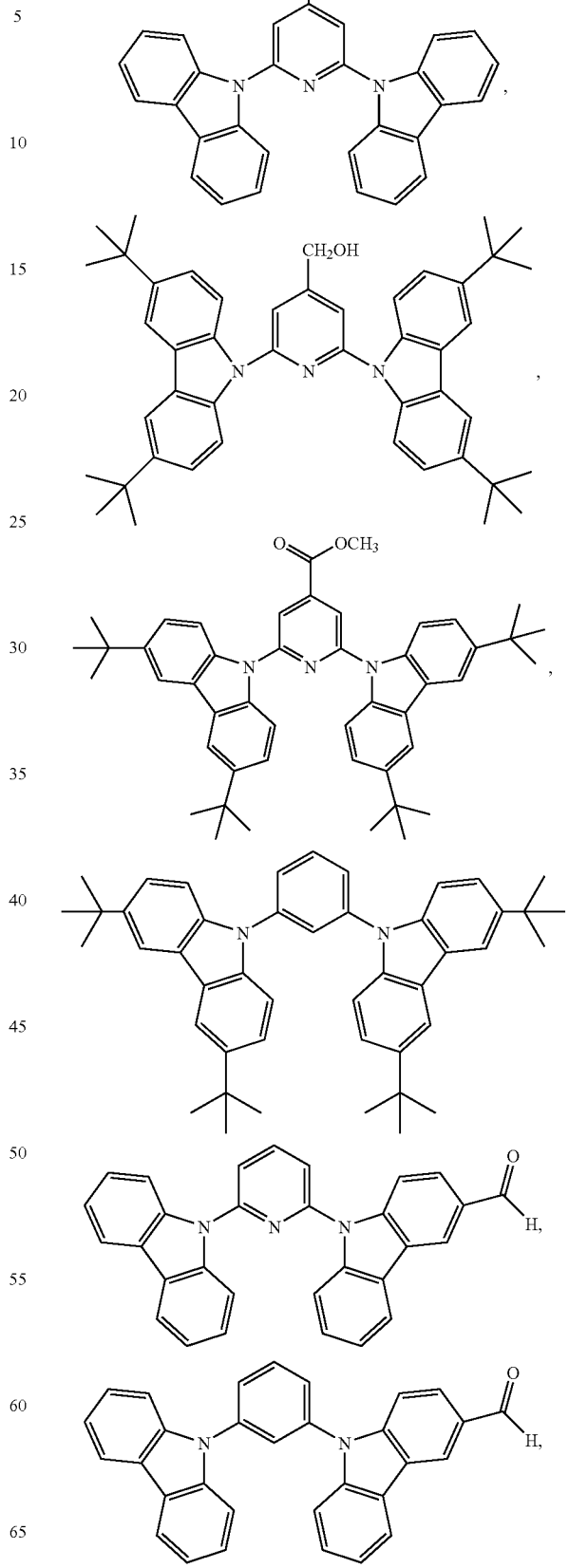

-continued

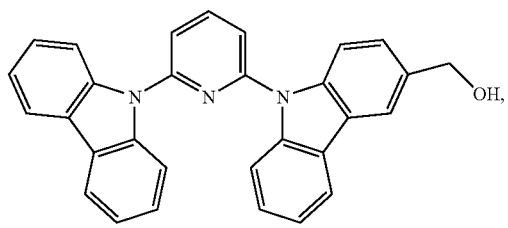

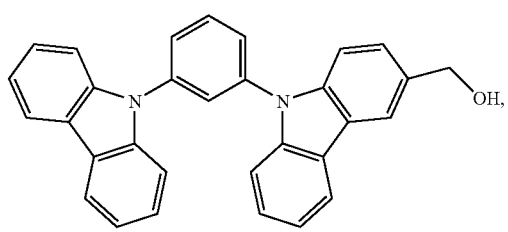

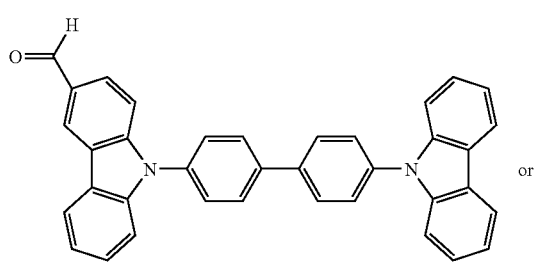

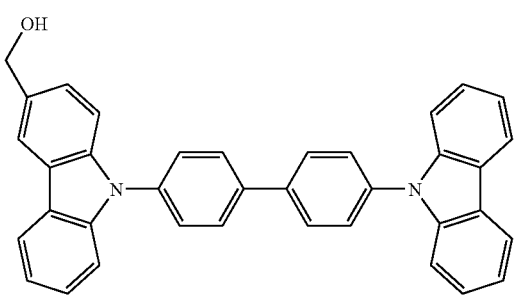

or

22. A compound represented by the following formula:

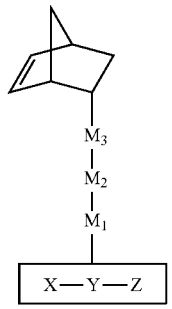

wherein:
X and Z each are carbazole group and are unsubstituted or substituted with one or more straight chain or branched alkyl groups;
Y is a conjugated cyclic or polycyclic heteroaromatic;
the X-Y-Z unit taken together is linked to the norbornene monomer by a linkage, $M_1$-$M_2$-$M_3$, wherein the linkage is attached to Y or one of X or Z;
$M_1$ and $M_3$ are independently absent or represent:
or

and is attached to the X-Y-Z unit through the carbon or oxygen atom on the ester, or through the ether oxygen atom, and $M_2$ is $R_3$;
$R_1$ and $R_2$ are independently absent or selected from the group consisting of alkane diyl, alkene diyl, alkyne diyl, and arene diyl, each of which are straight chain, branched chain or cyclic, having a carbon chain length of from 1 to 20 carbon atoms;
$R_3$ is absent or represents alkane diyl, alkene diyl, alkyne diyl, or arene diyl, each of which are straight chain, branched chain or cyclic, having a carbon chain length of $C_{1-20}$.

23. A polymer obtained by polymerizing a composition comprising the compound of claim 22.

24. The compound of claim 22, wherein Y is a carbazole.

* * * * *